United States Patent
McGowan et al.

(10) Patent No.: US 11,179,389 B2
(45) Date of Patent: Nov. 23, 2021

(54) PURINE INHIBITORS OF HUMAN PHOSPHATIDYLINOSITOL 3-KINASE DELTA

(71) Applicant: Merck Sharp & Dohme Corp., Rahway, NJ (US)

(72) Inventors: Meredeth A. McGowan, Boston, MA (US); Jason D. Katz, Newton Highlands, MA (US); Hua Zhou, Acton, MA (US); David James Witter, Norfolk, MA (US); Chaomin Li, Boston, MA (US); Kathryn A. Lipford, Boston, MA (US); Joey L. Methot, Westwood, MA (US); Abdelghani A. Achab, Melrose, MA (US); Xavier Fradera, Boston, MA (US); Shimin Xu, Beijing (CN); Jianmin Fu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/764,107

(22) PCT Filed: Dec. 12, 2018

(86) PCT No.: PCT/US2018/065061
§ 371 (c)(1),
(2) Date: May 14, 2020

(87) PCT Pub. No.: WO2019/125839
PCT Pub. Date: Jun. 27, 2019

(65) Prior Publication Data
US 2020/0390760 A1    Dec. 17, 2020

(30) Foreign Application Priority Data
Dec. 18, 2017    (WO) ................ PCT/CN2017/116918

(51) Int. Cl.
| A61K 31/497 | (2006.01) |
| C07D 471/10 | (2006.01) |
| C07D 498/10 | (2006.01) |
| C07D 403/14 | (2006.01) |
| C07D 401/14 | (2006.01) |
| C07D 413/14 | (2006.01) |
| A61K 31/5386 | (2006.01) |
| A61K 31/5377 | (2006.01) |
| C07D 491/107 | (2006.01) |

(52) U.S. Cl.
CPC ........ *A61K 31/497* (2013.01); *A61K 31/5377* (2013.01); *A61K 31/5386* (2013.01); *C07D 401/14* (2013.01); *C07D 403/14* (2013.01); *C07D 413/14* (2013.01); *C07D 471/10* (2013.01); *C07D 491/107* (2013.01); *C07D 498/10* (2013.01)

(58) Field of Classification Search
CPC .............. A61K 31/497; A61K 31/5377; A61K 31/5386; C07D 401/14; C07D 403/14; C07D 413/14; C07D 471/10; C07D 491/107; C07D 498/10
See application file for complete search history.

(56) References Cited

U.S. PATENT DOCUMENTS

| 8,791,267 B2* | 7/2014 | Singh | A61K 31/426 546/297 |
| 2012/0165331 A1 | 6/2012 | Badiger et al. | |
| 2017/0233380 A1 | 8/2017 | Das et al. | |

FOREIGN PATENT DOCUMENTS

| CH | WO2015/162461 | * 10/2015 |
| WO | 2006/071548 A2 | 7/2006 |
| WO | 2008/005368 A2 | 1/2008 |
| WO | 2011/047481 A1 | 4/2011 |
| WO | 2015106012 A1 | 7/2015 |
| WO | 2015/162461 A1 | 10/2015 |
| WO | 2017/172507 A1 | 10/2017 |

OTHER PUBLICATIONS

Substance Record for SID 172623106, Available Date: Feb. 28, 2014 [retrieved on Mar. 18, 2019]. Retrieved from the Internet: URL: https://pubchem.ncbl.nlm.nih.gov/substance/172623106 entire document.

International Search Report and Written Opinion for PCT/CN2017/116918, dated Sep. 18, 2018, 15 pages.

* cited by examiner

*Primary Examiner* — Dennis Heyer
(74) *Attorney, Agent, or Firm* — Patricia A. Shatynski; John C. Todaro

(57) ABSTRACT

The instant invention provides compounds of formula I which are PI3K-delta inhibitors, and as such are useful for the treatment of PI3K-delta-mediated diseases such as inflammation, asthma, COPD and cancer.

13 Claims, No Drawings

PURINE INHIBITORS OF HUMAN PHOSPHATIDYLINOSITOL 3-KINASE DELTA

CROSS-REFERENCE TO RELATED APPLICATIONS

This application is a U.S. National Phase application under 35 U.S.C. § 371 of PCT Application No. PCT/US2018/065061, filed on Dec. 12, 2018, which claims foreign priority of PCT Application No. PCT/CN2017/116918, filed on Dec. 18, 2017.

BACKGROUND OF THE INVENTION

Compounds are provided that inhibit phosphatidylinositol 3-kinase delta isoform (PI3K-delta) activity, including compounds that selectively inhibit PI3K-delta activity. The invention provides methods of using PI3K-delta inhibitory compounds to inhibit PI3K-delta mediated processes in vitro and in vivo.

Methods of inhibiting PI3K-delta activity, and methods of treating diseases, such as disorders of immunity and inflammation, in which PI3K-delta plays a role in leukocyte function are disclosed. Methods of using PI3K-delta inhibitory compounds to inhibit cancer cell growth or proliferation are also provided. Preferably, the methods employ active agents that selectively inhibit PI3K-delta, while not significantly inhibiting activity of other PI3K isoforms.

SUMMARY OF THE INVENTION

The present invention provides novel compounds which are inhibitors of phosphoinosititde 3-kinases delta (PI3K-delta). The invention also provides a method for the treatment and prevention of PI3K-delta-mediated diseases and disorders using the novel compounds, as well as pharmaceutical compositions containing the compounds.

DETAILED DESCRIPTION OF THE INVENTION

The present invention provides compounds of Formula (I):

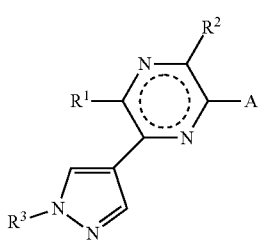

or a pharmaceutically acceptable salt thereof, wherein A is selected from:

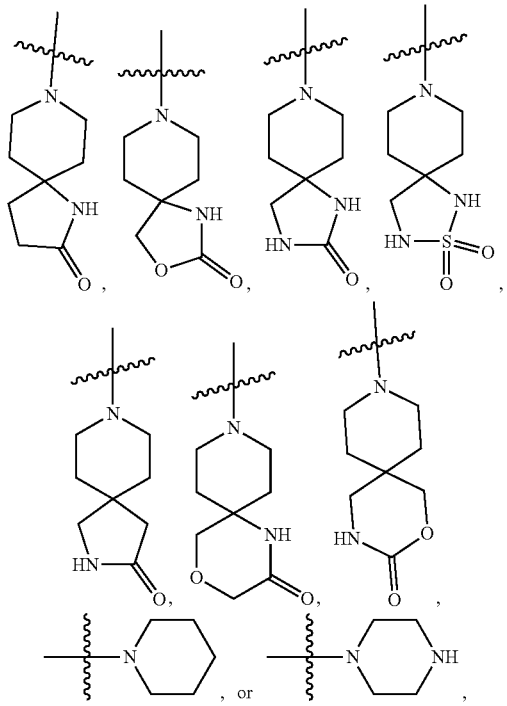

wherein A is substituted with 0, 1, 2, or 3 $R^4$, each independently selected from $C_1$-$C_{10}$ alkyl, $C_{1-10}$ haloalkyl, $C_{3-12}$ heterocycloalkyl$C_{0-6}$ alkyl, $C_{3-12}$ cycloalkyl($C_{0-6}$ alkyl), amino, $C_{3-12}$ cycloalkyl($C_{0-6}$ alkyl)aminocarbonyl, $C_{1-6}$ alkylamino($C_{0-6}$ alkyl), $C_{3-12}$ heterocycloalkylcarbonyl($C_{0-6}$ alkyl), $C_{1-10}$ alkylcarbonyl($C_{0-6}$ alkyl), $C_{3-12}$ cycloalkylcarbonyl($C_{0-6}$ alkyl), $C_{1-10}$ alkylcarboxy, or $C_{1-10}$ alkyloxy($C_{0-6}$ alkyl), wherein each $R^4$ is independently substituted by 0, 1, 2, or 3 $R^5$ independently selected from halogen, hydroxy, $C_1$-6 alkyl, $C_{1-4}$ alkoxy, or $C_{1-6}$ haloalkyl;

each $R^1$ and $R^2$ is independently selected from: hydrogen, or cyano provided that only one of $R^1$ or $R^2$ is cyano and the other is hydrogen; and $R^3$ is hydrogen, $C_{1-6}$ haloalkyl, or $C_{1-6}$ alkyl.

Representative compounds of the instant invention include, but are not limited to, the following compounds and their pharmaceutically acceptable salts thereof:

5-[1-(cyclopropylmethyl)-2-oxo-1,8-diazaspiro[4.5]dec-8-yl]-3-(1-methyl-1H-pyrazol-4-yl)pyrazine-2-carbonitrile;

5-{1-[(3-methyloxetan-3-yl)methyl]-2-oxo-3-oxa-1,8-diazaspiro[4.5]dec-8-yl}-3-(1-methyl-1H-pyrazol-4-yl)pyrazine-2-carbonitrile;

5-[1-(cyclopropylmethyl)-2-oxo-1,3,8-triazaspiro[4.5]dec-8-yl]-3-(1-methyl-1H-pyrazol-4-yl)pyrazine-2-carbonitrile;

5-{1-(cyclopropylmethyl)-3-[2-(dimethylamino)ethyl]-2-oxo-1,3,8-triazaspiro[4.5]dec-8-yl}-3-(1-methyl-1H-pyrazol-4-yl)pyrazine-2-carbonitrile:

5-{3-[2-(dimethylamino)ethyl]-2-oxo-1-(2,2,2-trifluoro-1-methylethyl)-1,3,8-triazaspiro[4.5]dec-8-yl}-3-(1-methyl-1H-pyrazol-4-yl)pyrazine-2-carbonitrile;

5-[1-(cyclopropylmethyl)-2,2-dioxido-2-thia-1,3,8-triazaspiro[4.5]dec-8-yl]-3-(1-methyl-1H-pyrazol-4-yl)pyrazine-2-carbonitrile;

5-[4-(cyclopropylmethyl)-2-oxo-3-oxa-1,8-diazaspiro[4.5]
dec-8-yl]-3-(1-methyl-1H-pyrazol-4-yl)pyrazine-2-carbonitrile;
5-(4-ethyl-3-oxo-2,8-diazaspiro[4.5]dec-8-yl)-3-(1-methyl-1H-pyrazol-4-yl)pyrazine-2-carbonitrile;
5-[1-(cyclopropylmethyl)-3-(2-methoxyethyl)-2-oxo-1,3,8-triazaspiro[4.5]dec-8-yl]-3-(1-methyl-1H-pyrazol-4-yl)pyrazine-2-carbonitrile;
5-[1-(2-methylpropyl)-3-oxo-2-oxa-4,9-diazaspiro[5.5]undec-9-yl]-3-(1-methyl-1H-pyrazol-4-yl)pyrazine-2-carbonitrile;
3-(1-methyl-1H-pyrazol-4-yl)-5-[2-oxo-1-(2,2,2-trifluoroethyl)-1,3,8-triazaspiro[4.5]dec-8-yl]pyrazine-2-carbonitrile;
5-[1-(cyclopropylmethyl)-2-oxo-3-oxa-1,8-diazaspiro[4.5]dec-8-yl]-3-[1-(difluoromethyl)-1H-pyrazol-4-yl]pyrazine-2-carbonitrile;
3-[(3R)-4-(cyclopropylcarbonyl)-3-methylpiperazin-1-yl]-5-(1-methyl-1H-pyrazol-4-yl)pyrazine-2-carbonitrile;
5-[(3R)-3-methyl-4-{[(1R,2R)-2-methylcyclopropyl]carbonyl}piperazin-1-yl]-3-(1-methyl-1H-pyrazol-4-yl)pyrazine-2-carbonitrile;
5-[(3R)-4-(cyclopropylcarbonyl)-3-methylpiperazin-1-yl]-3-(1-methyl-1H-pyrazol-4-yl)pyrazine-2-carbonitrile;
(2R)-4-[5-cyano-6-(1-methyl-1H-pyrazol-4-yl)pyrazin-2-yl]-N-cyclopropyl-2-methylpiperazine-1-carboxamide;
3-[1-(difluoromethyl)-1H-pyrazol-4-yl]-5-[(3R)-3-methyl-4-{[(1R,2R)-2-methylcyclopropyl]carbonyl}piperazin-1-yl]pyrazine-2-carbonitrile;
5-[(3R)-4-(cyclopropylcarbonyl)-3-methylpiperazin-1-yl]-3-[1-(~2~H_3_)methyl-1H-pyrazol-4-yl]pyrazine-2-carbonitrile;
5-[(3R)-4-(cyclopropylcarbonyl)-3-(2-methylpropyl)piperazin-1-yl]-3-(1-methyl-1H-pyrazol-4-yl)pyrazine-2-carbonitrile;
5-{1-[(3,3-difluorocyclobutyl)methyl]-2-oxo-1,8-diazaspiro[4.5]dec-8-yl}-3-(1-methyl-1H-pyrazol-4-yl)pyrazine-2-carbonitrile;
3-(1-methyl-1H-pyrazol-4-yl)-5-[2-oxo-1-(2,2,2-trifluoroethyl)-1,8-diazaspiro[4.5]dec-8-yl]pyrazine-2-carbonitrile;
3-(1-methyl-1H-pyrazol-4-yl)-5-(2-oxo-1-propyl-3-oxa-1,8-diazaspiro[4.5]dec-8-yl)pyrazine-2-carbonitrile;
5-[1-(cyclobutylmethyl)-2-oxo-3-oxa-1,8-diazaspiro[4.5]dec-8-yl]-3-(1-methyl-1H-pyrazol-4-yl)pyrazine-2-carbonitrile;
5-[1-(cyclopropylmethyl)-2-oxo-4-oxa-1,9-diazaspiro[5.5]undec-9-yl]-3-(1-methyl-1H-pyrazol-4-yl)pyrazine-2-carbonitrile;
5-(4-methyl-4-morpholin-4-ylpiperidin-1-yl)-3-(1-methyl-1H-pyrazol-4-yl)pyrazine-2-carbonitrile;
5-(4'-methyl-1,4'-bipiperidin-1'-yl)-3-(1-methyl-1H-pyrazol-4-yl)pyrazine-2-carbonitrile:
5-{(3R)-4-[(cis-3-methoxycyclobutyl)carbonyl]-3-methylpiperazin-1-yl}-3-(1-methyl-1H-pyrazol-4-yl)pyrazine-2-carbonitrile;
5-{(3R)-4-[(3,3-difluorocyclobutyl)carbonyl]-3-methylpiperazin-1-yl}-3-(1-methyl-1H-pyrazol-4-yl)pyrazine-2-carbonitrile;
5-[(3R)-4-{[(1S,2S)-2-fluorocyclopropyl]carbonyl}-3-methylpiperazin-1-yl]-3-(1-methyl-1H-pyrazol-4-yl)pyrazine-2-carbonitrile;
5-[(3R)-3-methyl-4-propanoylpiperazin-1-yl]-3-(1-methyl-1H-pyrazol-4-yl)pyrazine-2-carbonitrile;
5-{(3R)-3-methyl-4-[(1-methylcyclopropyl)carbonyl]piperazin-1-yl}-3-(1-methyl-1H-pyrazol-4-yl)pyrazine-2-carbonitrile;
3-(1-methyl-1H-pyrazol-4-yl)-5-[(3R)-3-methyl-4-(pyrrolidin-1-ylcarbonyl)piperazin-1-yl]pyrazine-2-carbonitrile;
5-[(3R)-3-methyl-4-(2-oxa-6-azaspiro[3.3]hept-6-ylcarbonyl)piperazin-1-yl]-3-(1-methyl-1H-pyrazol-4-yl)pyrazine-2-carbonitrile;
(2R)-4-[5-cyano-6-(1-methyl-1H-pyrazol-4-yl)pyrazin-2-yl]-N-(cyclopropylmethyl)-2-methylpiperazine-1-carboxamide;
5-[(3R)-4-{[(3S)-3-methoxypyrrolidin-1-yl]carbonyl}-3-methylpiperazin-1-yl]-3-(I-methyl-1H-pyrazol-4-yl)pyrazine-2-carbonitrile;
5-{(3R)-4-[(3-methoxyazetidin-1-yl)carbonyl]-3-methylpiperazin-1-yl}-3-(1-methyl-1H-pyrazol-4-yl)pyrazine-2-carbonitrile;
5-[(3R)-4-(azetidin-1-ylcarbonyl)-3-methylpiperazin-1-yl]-3-(1-methyl-1H-pyrazol-4-yl)pyrazine-2-carbonitrile;
methyl(2R)-4-[5-cyano-6-(1-methyl-1H-pyrazol-4-yl)pyrazin-2-yl]-2-methylpiperazine-1-carboxylate; or
5-[(3R)-3-methyl-4-{1[(1R,2R)-2-methylcyclopropyl]carbonyl}piperazin-1-yl]-3-(1H-pyrazol-4-yl)pyrazine-2-carbonitrile.

In a first embodiment of the invention, A is selected from:

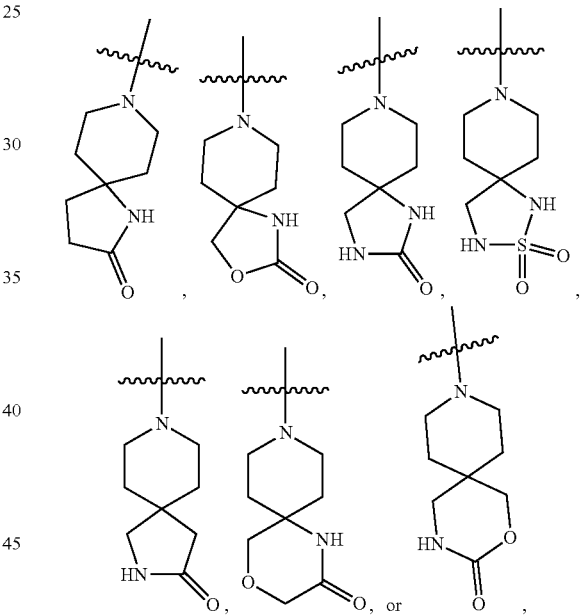

and the other groups are provided in the general formula I.

In a second embodiment of the invention, A is selected from

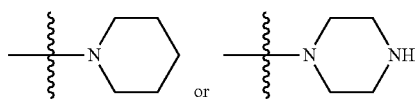

and the other groups are provided in the general formula I above or as in the first embodiment.

In a third embodiment of the invention. $R^4$ is each independently selected from $C_1$-$C_{10}$ alkyl, $C_{1-10}$ haloalkyl, $C_{3-12}$ heterocycloalkyl$C_{0-6}$ alkyl having 1, 2 or 3 heteroatoms selected from nitrogen or oxygen, $C_{3-12}$ cycloalkyl ($C_{0-6}$ alkyl), amino, $C_{3-12}$ cycloalkyl($C_{0-6}$ alkyl)aminocarbonyl, $C_{1-6}$ alkylamino($C_{0-6}$ alkyl), $C_{3-12}$ heterocycloalkylcarbonyl($C_{0-6}$ alkyl) having 1, 2 or 3 heteroatoms selected from nitrogen or oxygen, $C_{1-10}$ alkylcarbonyl($C_{0-6}$ alkyl), $C_{3-12}$ cycloalkylcarbonyl($C_{0-6}$ alkyl), $C_{1-10}$ alkylcarboxy, or $C_{1-10}$ alkyloxy($C_{0-6}$ alkyl), and the other groups are provided in the general formula 1 above or as in the first through second embodiments.

In a third embodiment of the invention, each $R^4$ is independently selected from $C_1$-$C_{10}$ alkyl, $C_{1-10}$ haloalkyl, $C_{3-12}$ heterocycloalkyl$C_{0-6}$ alkyl having 1, 2 or 3 heteroatoms selected from nitrogen or oxygen, $C_{3-12}$ cycloalkyl ($C_{0-6}$ alkyl), amino, $C_{3-12}$ cycloalkyl($C_{0-6}$ alkyl)aminocarbonyl, $C_{1-6}$ alkylamino($C_{0-6}$ alkyl), $C_{3-12}$ heterocycloalkylcarbonyl($C_{0-6}$ alkyl) having 1, 2 or 3 heteroatoms selected from nitrogen or oxygen, $C_{1-10}$ alkylcarbonyl($C_{0-6}$ alkyl), $C_{3-12}$ cycloalkylcarbonyl($C_{0-6}$ alkyl), $C_{1-10}$ alkylcarboxy, or $C_{1-10}$ alkyloxy($C_{0-6}$ alkyl), and the other groups are provided in the general formula I above or as in the first through second embodiments.

In a fourth embodiment, each R is independently selected from $C_1$-$C_{10}$ alkyl, $C_{1-10}$ haloalkyl having 1, 2, 3 or 4 halogen atoms selected from fluoro or chloro, $C_{3-8}$ heterocycloalkyl$C_{0-6}$ alkyl having 1, 2 or 3 heteroatoms selected from nitrogen or oxygen, $C_{3-8}$ cycloalkyl($C_{0-6}$ alkyl), amino, $C_{3-8}$ cycloalkyl($C_{0-6}$ alkyl)aminocarbonyl, $C_{1-6}$ alkylamino ($C_{0-6}$ alkyl), $C_{3-12}$ heterocycloalkylcarbonyl($C_{0-6}$ alkyl) having 1, 2 or 3 heteroatoms selected from nitrogen or oxygen, $C_{1-10}$ alkylcarbonyl($C_{0-6}$ alkyl), $C_{3-8}$ cycloalkylcarbonyl ($C_{0-6}$ alkyl), $C_{1-10}$ alkylcarboxy, or $C_{1-10}$ alkyloxy($C_{0-6}$ alkyl), and the other groups are provided in the general formula I above or as in the first through third embodiments.

In a fifth embodiment, each $R^4$ is independently selected from cyclopropylmethyl, cyclobutylmethyl, 2,2,2-trifluoroethyl, propyl, oxetanylmethyl, 2,2,2-trifluoro-1-methylethyl, methylaminoethyl, methoxyethyl, cyclopropylaminocarbonyl, ethylcarbonyl, ethyl, isobutyl, methyl, morpholinyl, cyclopropylcarbonyl, cyclobutylcarbonyl, piperidinyl, pyrrolidinylcarbonyl, 2-oxa-6-azaspiro[3.3]heptylcarbonyl, (cyclopropylmethyl)aminocarbonyl, azetidinylcarbonyl, and methylcarboxy, and the other groups are provided in the general formula I above or as in the first through fourth embodiments.

In a sixth embodiment of the invention, each $R^5$ is independently selected from halogen, hydroxy, $C_{1-6}$ alkyl, $C_{1-4}$ alkoxy, or $C_{1-6}$ haloalkyl having 1, 2 or 3 halogen selected from chloro or fluoro, and the other groups are provided in the general formula I above or as in the first through fifth embodiments.

In a seventh embodiment of the invention, each $R^5$ is independently selected from halogen, $C_{1-6}$ alkyl, or $C_{1-4}$ alkoxy, and the other groups are provided in the general formula I above or as in the first through sixth embodiments.

In a eighth embodiment, each $R_5$ is independently selected from fluoro, $C_{1-3}$ alkyl, ethoxy, or methoxy, and the other groups are provided in the general formula I above or as in the first through seventh embodiments.

In a ninth embodiment, each $R^5$ is independently selected from fluoro, methyl, or methoxy, and the other groups are provided in the general formula I above or as in the first through eighth embodiments.

In a tenth embodiment of the invention, $R^3$ is selected from methyl, ethyl, propyl, butyl, pentyl, difluoromethyl, trifluoromethyl, trifluoroethyl or hydrogen, and the other groups are provided in the general formula I above or as in the first through ninth embodiments.

In a eleventh embodiment. $R^3$ is selected from methyl, difluoromethyl, or hydrogen, and the other groups are provided in the general formula I above or as in the first through tenth embodiments.

In the twelfth embodiment, $R^1$ is hydrogen and $R^2$ is cyano, and the other groups are provided in formula I above or as in the first through eleventh embodiments.

In the thirteenth embodiment, $R^1$ is cyano and $R^2$ is hydrogen, and the other groups are provided in formula I above or as in the first through twelfth embodiments.

The invention also encompasses pharmaceutical compositions containing a compound of formula I, and methods for treatment or prevention of PI3K-delta mediated diseases using compounds of formula I.

One aspect of the present invention is to provide compounds that can inhibit the biological activity of human PI3K-delta. Another aspect of the invention is to provide methods of selectively modulating human PI3K-delta activity and thereby promoting medical treatment of diseases mediated by PI3K-delta dysfunction.

In one embodiment of the invention, the compounds of formula I inhibit PI3K-delta activity in biochemical and cell-based assays and exhibit therapeutic activity in medical conditions in which PI3K-delta activity is excessive or undesirable.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "-O-alkyl," etc. The invention is described using the following definitions unless otherwise indicated.

When any variable (e.g. aryl, heteroaryl, $R^1$, $R^5$, etc.) occurs more than one time in any constituent, its definition on each occurrence is independent at every other occurrence. Also, combinations of substituents/or variables are permissible only if such combinations result in stable compounds.

The wavy line ∿∿∿, as used herein, indicates a point of attachment to the rest of the compound.

The term "$C_{1-6}$" includes alkyls containing 6, 5, 4, 3, 2, or 1 carbon atoms.

The term "$C_0$" as employed in expressions such as "$C_{0-6}$alkyl" means a direct covalent bond; or when the term appears at the terminus of a substituent $C_{0-6}$alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

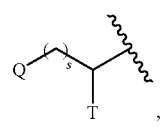

wherein s is an integer equal to zero, 1 or 2, the structure is

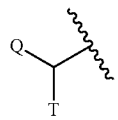

when s is zero.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

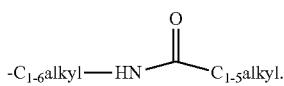

Lines drawn into the ring systems, such as, for example:

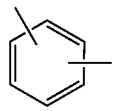

indicate that the indicated line (bond) may be attached to any of the substitutable ring carbon atoms.

The term "alkyl," as used herein, refers to an aliphatic hydrocarbon group having one of its hydrogen atoms replaced with a bond. An alkyl group may be straight or branched and contain from about 1 to about 10 carbon atoms. In different embodiments, an alkyl group contains from 1 to 6 carbon atoms ($C_{1-6}$ alkyl) or from about 1 to about 3 carbon atoms ($C_{1-3}$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkanoyl" has the general formulas of RC=O, where R may be aliphatic alicyclic or aromatic.

The term "alkoxy" represents a linear or branched alkyl group of indicated number of carbon atoms attached through an oxygen bridge.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "aryl," as used herein, refers to an aromatic monocyclic or multicyclic ring system comprising from about 6 to about 14 carbon atoms. In one embodiment, an aryl group contains from about 6 to about 10 carbon atoms. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

"Carboxy" refers to the functional group —C(O)OR, for example: ethylcarboxy is

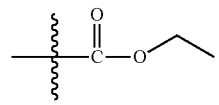

phenylcarboxy is

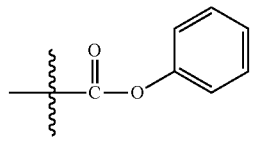

and cyclopropycarboxy is

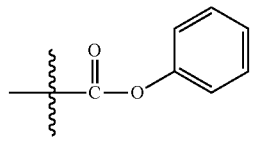

"Celite®" (Fluka) diatomite is diatomaceous earth, and can be referred to as "celite".

"Cycloalkyl" means a carbocyclic ring system having 3 to 12 ring carbon atoms; said ring system may be (a) a monocyclic saturated carbocycle or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.4]heptane, spiro[2.2]pentane), or are bridged groups (e.g., norbomane). Additional examples within the above meaning include, but are not limited to, cyclopropane, cyclobutane, cyclopentane, cyclohexane, cyclooctyl, decalin, spiro[4.5]decane, spiro[2.5]oxtyl, bicyclo[2,2,2]octane, and the like.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "heteroaryl", as used herein, refers to an aromatic monocyclic or multicyclic ring system having at least one aromatic ring comprising about 5 to about 14 ring atoms, wherein from 1 to 4 of the ring atoms is independently O, N or S and the remaining ring atoms are carbon atoms.

The term "heterocycloalkyl," as used herein, refers to a non-aromatic saturated monocyclic or multicyclic ring system comprising 3 to about 11 ring atoms, wherein from 1 to 4 of the ring atoms are independently O, S, or N, and the remainder of the ring atoms are carbon atoms. A heterocycloalkyl group can be joined via a ring carbon, or ring nitrogen atom. Said ring system may be (a) a saturated monocyclic ring or a partially unsaturated ring, or (b) a bicyclic saturated carbocycle. For a bicyclic system, within either (a) or (b), the rings are fused across two adjacent ring carbon atoms (e.g., decahydroisoquinoline), at one ring carbon atom (e.g., spiro[2.4]heptyl, spiro[2.2]pentane), or are bridged groups (e.g., 2.5-diazabicyclo[2.2.1]heptyl).

In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Sulfanyl" refers to mercapto radical, —SH. For example, methylsulfanyl is —$SCH_3$.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is substituted with 0, 1, 2, 3, or 4 substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "CH3", e.g. "—CH3" or using a straight line representing the presence of the methyl group, e.g. "-", i.e.,

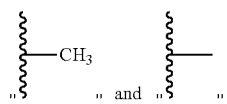

have equivalent meanings.

For variable definitions containing terms having repeated terms, e.g., $(CRiRj)_r$, where r is the integer 2, $R_i$ is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then $(CRiRj)_2$ can be

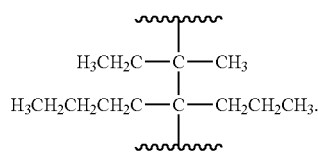

"Patient" for the purposes of the present invention includes humans and other animals, particularly mammals and other organisms. Thus the methods are applicable to both human therapy and veterinary applications.

A "subject" is a human or non-human mammal. In one embodiment, a subject is a human. In one embodiment the subject is a cat or dog. In another embodiment, a subject is a primate. In another embodiment, a subject is a monkey. In another embodiment, a subject is a chimpanzee. In still another embodiment, a subject is a rhesus monkey.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means "unsubstituted or substituted." and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —(CR³R³)₂—, each occurrence of the two R³ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Optical Isomers—Diastereomers—Geometric Isomers—Tautomers

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. (For example, if a compound of formula I incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, (R and S)-3-(1-methyl-1H-pyrazol-4-yl)-5-(3-methylpiperazin-1-yl)pyrazine-2-carbonitrile hydrochloride, the "and" indicates a racemic mixture of the enantiomers. That is, the individual enantiomers were not individually isolated.

When the stereomeric nomenclature includes "or", for example, (R or S)-3-(1-methyl-1H-pyrazol-4-yl)-5-(3-methylpiperazin-1-yl)pyrazine-2-carbonitrile, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

Diastereomeric mixtures can be separated into their individual diastereomers on the basis of their physical chemical differences by methods well known to those skilled in the art, such as, for example, by chromatography (e.g. chiral HPLC column) and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention.

Prodrugs and Solvates

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of formula I or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy) ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$) alkyl, ($C_3$-$C_7$) cycloalkyl, benzyl, or R-carbonyl is a natural α-aminoacyl or natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —C(Y$^4$)Y$^5$ wherein Y$^4$ is H or methyl and Y$^5$ is mono-N- or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3) 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R spectroscopy, show the presence of the solvent (or water) in the crystals as a solvate (or hydrate).

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and examples herein using appropriate isotopically-enriched reagents and/or intermediates.

Utilities

Compounds of the Invention have activity for PI3K-delta. Compounds of this invention have been tested using the those skilled in the art or by processes analogous to those described in the Schemes and Examples herein using appropriate isotopically-enriched reagents and/or intermediates.

Assays described in the Biological Examples and have been determined to be inhibitors of PI3K-delta. Suitable in vitro assays for measuring PI3K-delta activity and the inhibition thereof by compounds are known in the art. For further details of an in vitro assay for measuring PI3K-delta, see the Biological Examples herein. Cell-based assays for measurement of in vitro efficacy in treatment of cancer are known in the art. In addition, assays are described in the Biological Examples provided herein.

Suitable in vivo models for cancer are known to those of ordinary skill in the art. See for example, international patent application published as WO 2012/037226 for further details of in vivo models for prostate adenocarcinoma, glioblastoma, lung carcinoma, and melanoma. Following the examples disclosed herein, as well as that disclosed in the art, a person of ordinary skill in the art can determine the activity of a compound of this invention.

Compounds of Formula I may be useful for treating diseases, including autoimmune disorders, inflammatory diseases, and cancers, which are listed below.

Cancers: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adeno-carcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors. SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma, fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplasia syndrome), Hodgkin's disease, non-Hodgkin's lymphoma [malignant lymphoma]; Skin: malignant melanoma, basal cell carcinoma, squamous cell carcinoma. Karposi's sarcoma, moles dysplastic nevi, lipoma, angioma, dermatofibroma, keloids, psoriasis; and Adrenal glands: neuroblastoma.

Autoimmune diseases: Hashimoto's thyroiditis, systemic lupus erythematosus (SLE), Goodpasture's syndrome, pemphigus, receptor autoimmune diseases, Basedow's disease (Graves' disease), myasthernia gravis, insulin resistant diseases, autoimmune hemolytic anemia, autoimmune thrombocytopenic purpura, autoimmune encephalomyelitis, rheumatism, rheumatoid arthritis, scleroderma, mixed connective tissue disease, polymyositis, pernicious anemia, idiopathic Addison's disease, some types of infertility, glomerulonephritis, bullous pemphigus, Sjogren's syndrome, some types of diabetes, adrenergic agent resistance, chronic active hepatitis, primary biliary cirrhosis, endocrine failure, vitiligo, angiitis, post-cardiac surgery syndrome, urticaria, atopic dermatiti and multiple sclerosis, autoimmune polyglandular disease (also known as autoimmune polyglandular syndrome), autoimmune alopecia; pernicious anemia; vitiligo; autoimmune hypopituatarism, and Guillain-Barre syndrome.

Inflammatory Diseases: Asthma, allergic rhinitis, psoriasis, inflammatory arthritis, rheumatoid arthritis, psoriatic arthritis or osteoarthritis, irritable bowel syndrome, ulcerative colitis, Crohn's disease, respiratory allergies (asthma, hay fever, allergic rhinitis) or skin allergies, scleraciema, mycosis fungoides, acute inflammatory responses (such as acute respiratory distress syndrome and ishchemia/reperfusion injury), dermatomyositis, alopecia greata, chronic actinic dermatitis, eczema, Behcet's disease, Pustulosis palmoplanteris, Pyoderma gangrenum, Sezary's syndrome, atopic dermatitis, systemic sclerosis, and morphea.

Central Nervous System Disorders: multiple sclerosis, schizophrenia.

Thus, in one embodiment, the invention provides a method of inhibiting PI3K-delta comprising contacting the PI3K-delta with an effective amount of a compound as disclosed herein.

In another embodiment, the invention provides a method of treating a PI3K-delta modulated disease comprising administering to a mammal in need of such treatment a therapeutically effective amount of a compound as disclosed herein.

In another embodiment, the invention provides a method of treating cancer disease mediated by PI3K-delta comprising administering to a mammal in need of such treatment a therapeutically effective amount of a compound as disclosed herein.

Compounds of the invention are also useful as inhibitors of PI3K-delta in vivo for studying the in vivo role of PI3K-delta in biological processes, including the diseases described herein. Accordingly, the invention also comprises a method of inhibiting PI3K-delta in vivo comprising administering a compound or composition of the invention to a mammal.

Accordingly, another aspect of the present invention provides a method for the treatment or prevention of a PI3K-delta mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a PI3K-delta mediated diseases or disorders.

Dose Ranges

The magnitude of prophylactic or therapeutic dose of a compound of formula I or Ib will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 milligram of active agent per kilogram body weight of a mammal (mg/kg) to about 100 mg/kg, typically, between 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.01 mg to 10 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, 400 mg, or 500 mg.

The final dosage regimen will be determined by the attending physician in view of good medical practice, considering various factors that modify the action of drugs, e.g., the agent's specific activity, the identity and severity of the disease state, the responsiveness of the patient, the age, condition, body weight, sex, and diet of the patient, and the severity of the disease state. Additional factors that can be taken into account include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages can be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, can be preferred for continuous infusion.

Pharmaceutical Compositions

Another aspect of the present invention provides pharmaceutical compositions comprising a compound of formula I with a pharmaceutically acceptable carrier. For the treatment of any of the prostanoid mediated diseases compounds of Formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion, the oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

In certain embodiments, a compound of Formula I is combined in a pharmaceutical combination formulation, or dosing regimen as combination therapy, with one or more other therapeutic agents that has anti-inflammatory or anti-hyperproliferative properties or that is useful for treating an inflammation, immune-response disorder, or hyperproliferative disorder (e.g., cancer). The other therapeutic agent of the pharmaceutical combination formulation or dosing regimen preferably has complementary activities to the compound of Formula I such that they do not adversely affect each other. Such agents are suitably present in combination in amounts that are effective for the purpose intended.

In one embodiment of the invention, the compound of Formula I, or a stereoisomer, tautomer, or pharmaceutically acceptable salt or prodrug thereof, may be co-administered with one or more other therapeutic agents for the treatment and prevention of PI3Kdelta mediated diseases. Thus in another aspect the present invention provides pharmaceutical compositions for treating PI3Kdelta mediated diseases comprising a therapeutically effective amount of a compound of formula I and one or more other therapeutic agents.

In one embodiment for example, for the treatment of the inflammatory diseases rheumatoid arthritis, psoriasis, inflammatory bowel disease, COPD, asthma and allergic rhinitis a compound of Formula I may be combined with other therapeutic agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-I) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

In another embodiment of the invention, the compounds of Formula I, or a stereoisomer, tautomer, or pharmaceutically acceptable salt or prodrug thereof, may be employed alone or in combination with other therapeutic agents for the treatment of hyperproliferative disorders (e.g., cancer) including standard chemotherapy regimens, and anti-CD20 monoclonal antibodies, rituximab, bendamustine, ofatumumab, fludarabine, lenalidomide, and/or bortezomib.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active therapeutic agents simultaneously exert their biological activities.

Kits

In one aspect, the present invention provides a kit comprising a therapeutically effective amount of at least one compounds of Formula I, or a pharmaceutically acceptable salt or prodrug of said compound and a pharmaceutically acceptable carrier, vehicle or diluent.

In another aspect the present invention provides a kit comprising an amount of at least one compounds of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more compounds of Formula I and the one or more additional therapeutic agents are provided in the same container. In one embodiment, the one or more compounds of Formula I and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

SCHEMES AND EXAMPLES

The abbreviations used herein have the following tabulated meanings. Abbreviations not tabulated below have their meanings as commonly used unless specifically stated otherwise.

Abbreviations Used in the Description of Compound Preparation

| | |
|---|---|
| Ac | acetyl |
| Boc | tert-butoxycarbamate |
| dba | dibenzylideneacetone |
| CDI | carbonyldiimidazole |
| DCC | N,N'-Dicyclohexylcarbodiimide |
| DCM | dichloromethane |
| DEA | diethylamine |
| DIEA | N,N-diisopropylethylamine |
| DMAP | dimethylaminopyridine |
| DME | 1,2 dimethoxyethane |
| DMF | dimethylformamide |
| DMSO | dimethyl sulfoxide |
| dppf | 1,1'-bis(diphenylphosphino)ferrocene |
| EDC | N-(3-dimethylaminopropyl)-N'-ethylcarbodiimide hydrochloride |
| EI | electron ionization |
| ESI | electrospray ionization |
| EtOH | ethanol |
| EtOAc | ethyl acetate |
| GST | Glutathione S-transferase |
| h, hr, H, Hr. | hour |
| HATU | 1-[bis(dimethylamino)methylene]-1H-1,2,3-triazolo[4,5-b]pyridinium 3-oxid-hexafluorophosphate |
| HOBT | 1-hydroxybenzotriazole hydrate |
| HPLC | high performance liquid chromatography |
| HTRF | Homogeneous Time Resolved Fluorescence |
| i-Pr$_2$NEt | N,N'-diisopropylethylamine |
| IPA | 2-propanol |
| LC/MS | liquid chromatography coupled to mass spectrometer |
| min | minute(s) |
| MeCN, ACN | acetonitrile |
| MeOH | methanol |
| MS | mass spectrum (data) |
| NH$_4$HCO$_3$ | Ammonium bicarbonate |
| NMP | N-methylpyrrolidone; 1-methyl-2-pyrrolidinone |
| NMR | nuclear magnetic resonance (data) |
| Pd(dppf) | [1,1'-bis(diphenylphosphino)ferrocene]dichloropalladium(II) |
| PdCl$_2$(dppf)-CH$_2$Cl$_2$ | tris(dibenzylideneacetone)palladium-methylene chloride |
| Pd(OH)$_2$/C | Palladium hydroxide on activated charcoal, Pearlman's catalyst |
| PMB | 4-methoxybenzyl |
| Pr | propyl |
| RT, rt. | room temperature |
| SFC | supercritical fluidic chromatography |
| tBu | tert-butyl |
| t-BuOH | tert-butanol |
| TEA | triethylamine |
| TBACl | tetrabutylammonium chloride |
| TFA | trifluoroacetic acid |
| THF | tetrahydrofuran |

General Synthetic Schemes

The compounds of the generic formula may be prepared from known or readily prepared starting materials, following methods known to one skilled in the art of organic synthesis. Methods useful for making the compounds are set forth in the Examples below and are generalized in Schemes 1 through 8 presented below. Alternative synthetic pathways and analogous structures will be apparent to those skilled in the art of organic synthesis.

In cases where mixtures or gradients of solvents or solution reagents are described, the mixtures are on a volume basis unless otherwise indicated.

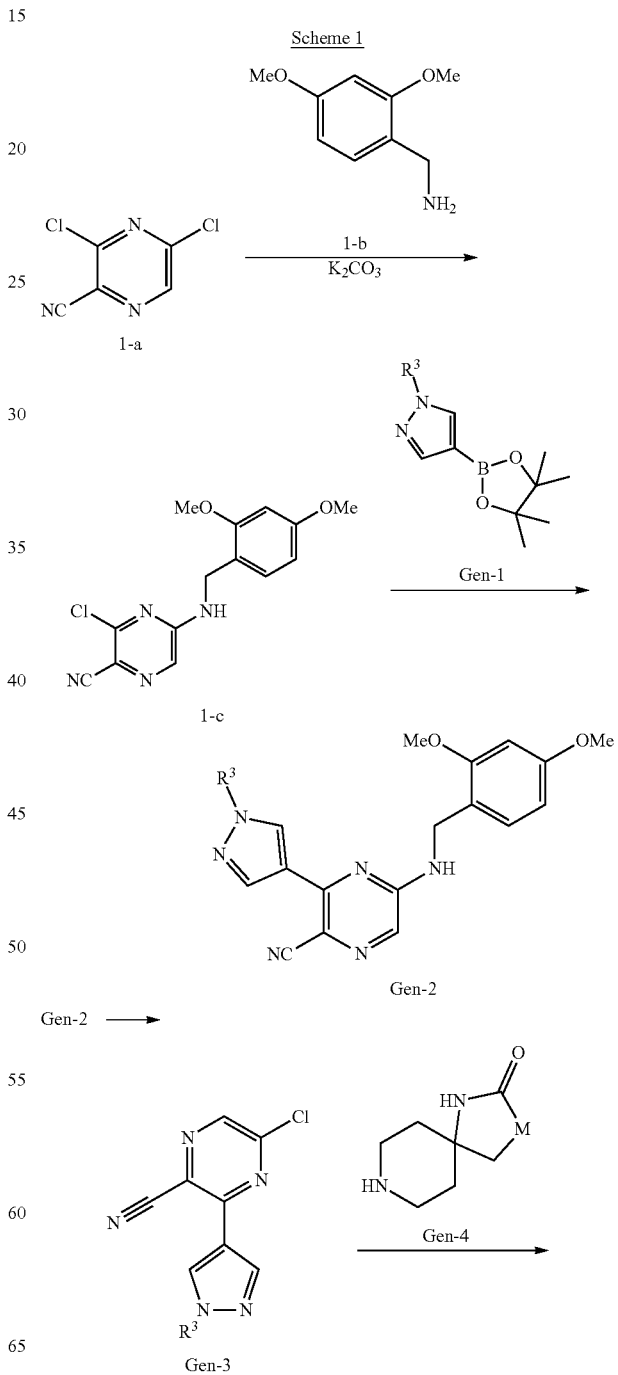

Scheme 1

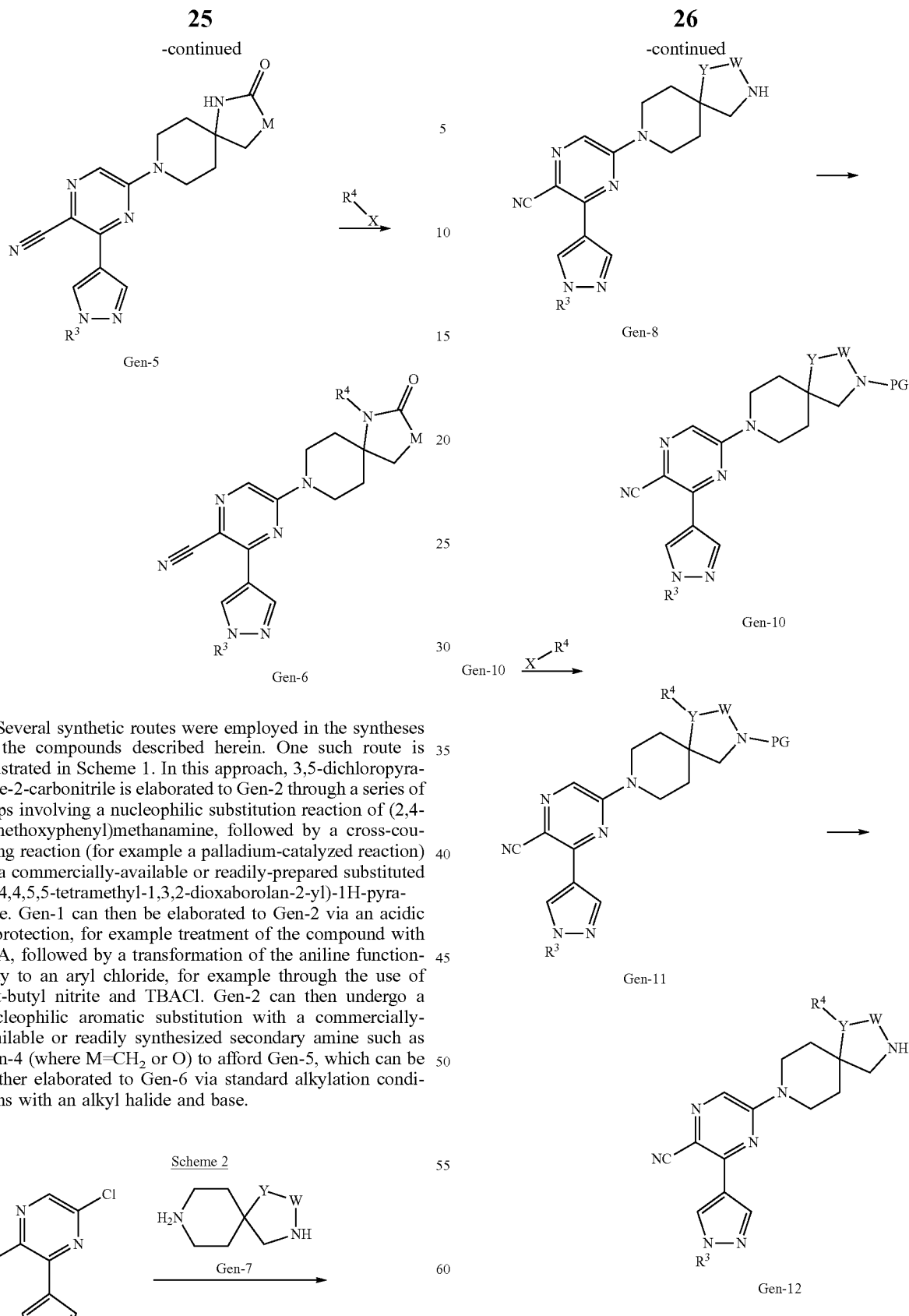

Several synthetic routes were employed in the syntheses of the compounds described herein. One such route is illustrated in Scheme 1. In this approach, 3,5-dichloropyrazine-2-carbonitrile is elaborated to Gen-2 through a series of steps involving a nucleophilic substitution reaction of (2,4-dimethoxyphenyl)methanamine, followed by a cross-coupling reaction (for example a palladium-catalyzed reaction) of a commercially-available or readily-prepared substituted 4-(4,4,5,5-tetramethyl-1,3,2-dioxaborolan-2-yl)-1H-pyrazole. Gen-1 can then be elaborated to Gen-2 via an acidic deprotection, for example treatment of the compound with TFA, followed by a transformation of the aniline functionality to an aryl chloride, for example through the use of tert-butyl nitrite and TBACl. Gen-2 can then undergo a nucleophilic aromatic substitution with a commercially-available or readily synthesized secondary amine such as Gen-4 (where M=CH$_2$ or O) to afford Gen-5, which can be further elaborated to Gen-6 via standard alkylation conditions with an alkyl halide and base.

In some cases, Gen-3 can be elaborated to Gen-8 via a SnAr reaction (Nucleophilic Aromatic Substitution reaction) with a commercially-available or readily synthesized secondary amine Gen-7, where W=CO, or SO$_2$ and Y=NH or CH₂. In these cases a free NH can be protected with a protecting group under standard conditions (for example with Boc₂O to provide the tert-butyl carbamate) and the remaining nitrogen can be functionalized, for example by an alkylation with an alkyl halide and base (for example LDA, lithium diisopropylamide, in the case of Y=CH₂), to provide Gen-11. Gen-11 can then be elaborated to Gen-12 via a standard deprotection (for example removal of a Boc group under acidic conditions).

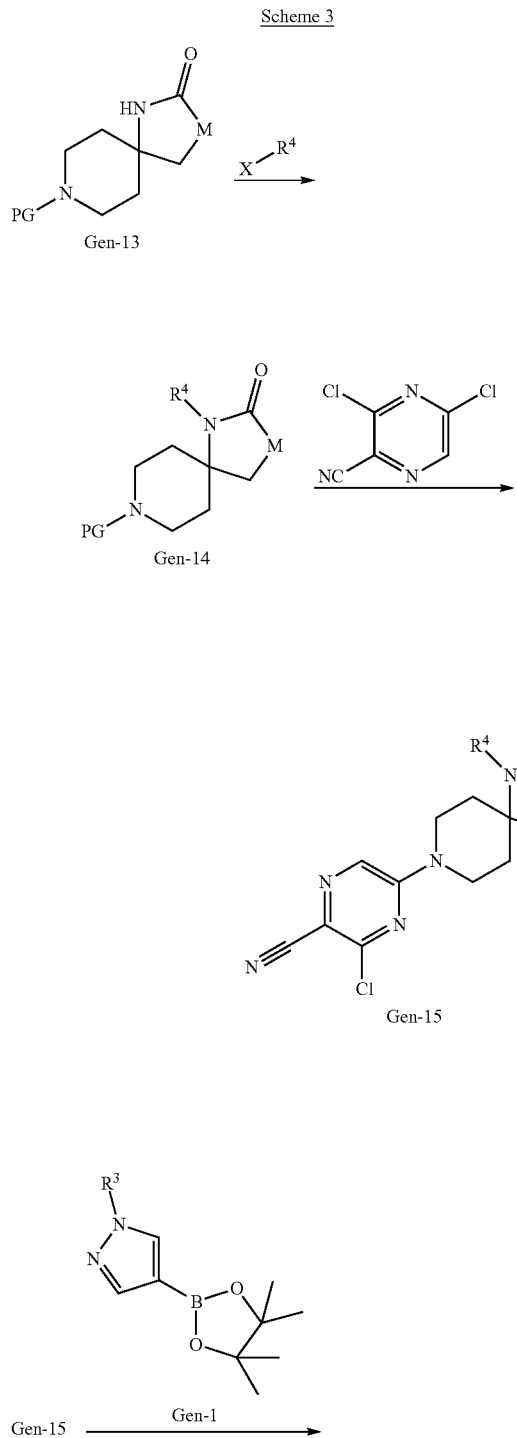

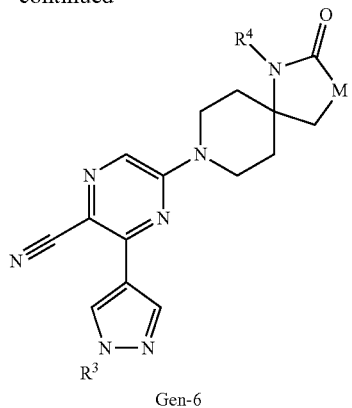

In an alternative approach, a commercially-available or readily synthesized secondary amine bearing a protecting group (Gen-13) was alkylated with an appropriate alkyl halide and base to form Gen-14. Gen-14 can then be de-protected under standard conditions (for example, a Boc group was removed under acidic conditions) and the secondary amine can then be added via a nucleophilic substitution reaction into 3,5-dichloropyrazine-2-carbonitrile to provide Gen-15. Gen-15 could then engage in a cross-coupling reaction with a commercially-available or readily-prepared substituted 4-(4,4,5,5-tetramethyl-1,3,2-dioxa-borolan-2-yl)-1H-pyrazole (for example via a palladium-catalyzed Suzuki coupling) to provide Gen-6.

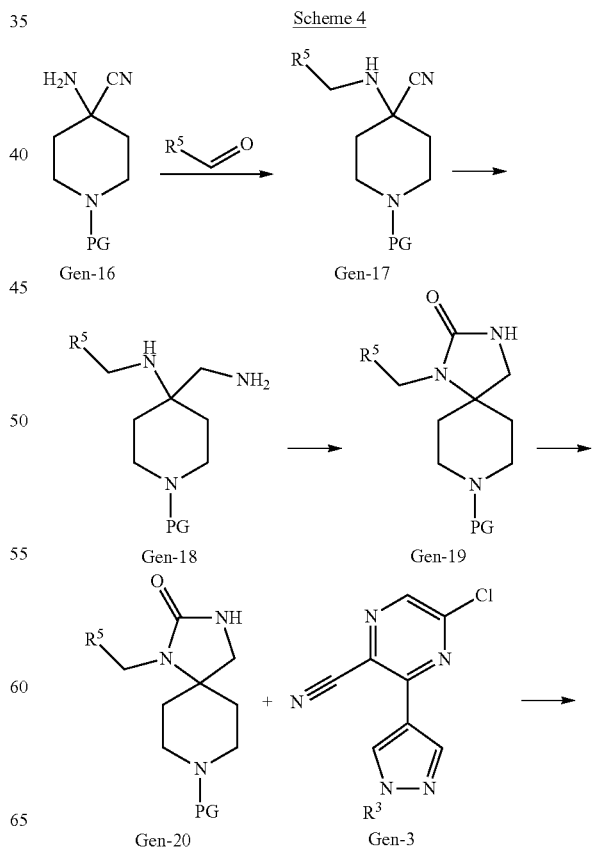

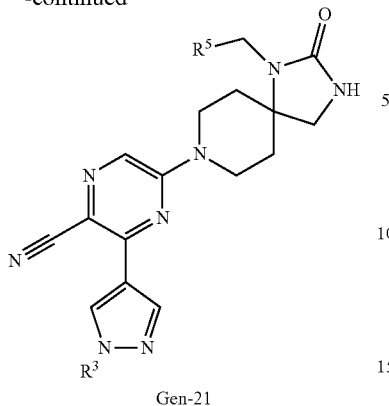

Gen-21

In some cases, an amino-nitrile such as Gen-16 engaged in a reductive amination reaction with an aldehyde to form Gen-17 (for example, using sodium triacetoxyborohydride and cyclopropanecarboxaldehyde) to provide Gen-17. The nitrile could then be reduced using standard conditions (for example lithium aluminum hydride) to the corresponding primary amine Gen-18, which can then engage in a cyclization reaction to form the urea Gen-19 using a reagent such as triphosgene. Gen-19 could then be used in an analogous manner to Gen-14 above or could be deprotected using standard conditions (for example acidic conditions to remove a Boc group) to provide Gen-20. Gen-20 could then engage in a nucleophilic aromatic substitution reaction with Gen-3 to provide Gen-21.

Scheme 4

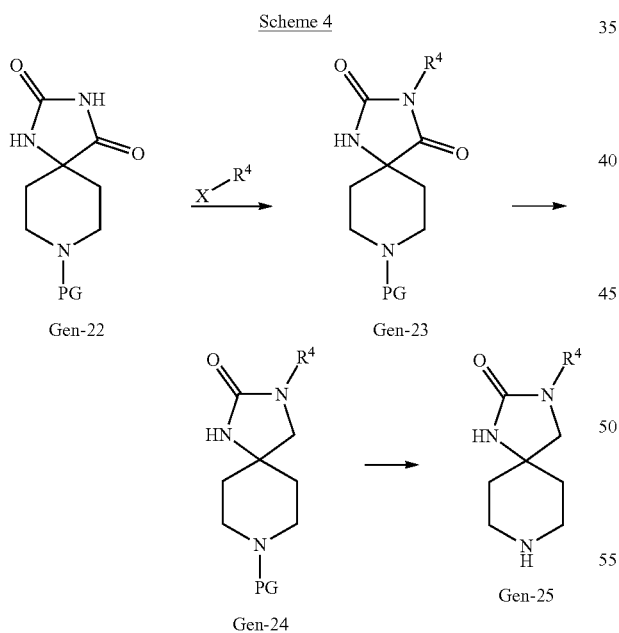

In a related approach, a commercially-available or easily synthesized protected hydantoin Gen-22 could be alkylated using standard conditions with an alkyl halide to afford Gen-23. Gen-23 could then be partially reduced (for example using lithium aluminum hydride) to provide using urea Gen-24, which could be used in an analogous manner to Gen-14. Gen-24 could also be deprotected (for example, a benzyl group could be removed under hydrogenation conditions) to afford Gen-25, which could then be used in an analogous manner to Gen-20 in the example above.

Scheme 5

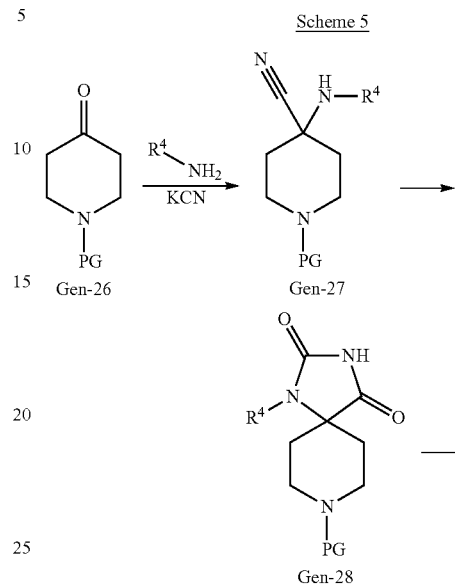

In another approach, a protected commercially-available piperidone Gen-26 was engaged in a Strecker reaction (a known synthesis of synthesize of an amino acid from an aldehyde (or ketone)), with a primary amine and potassium cyanide to form Gen-27. Amino-nitrile Gen-27 could then be cyclized to form the hydantoin, for example through the use of sulfurisocyanatidic chloride, to form hydantoin Gen-28. Gen-28 could then be partially-reduced (for example using lithium aluminum hydride) to provide Gen-29, which could engage in the transformations outlined above for Gen-24.

Scheme 6

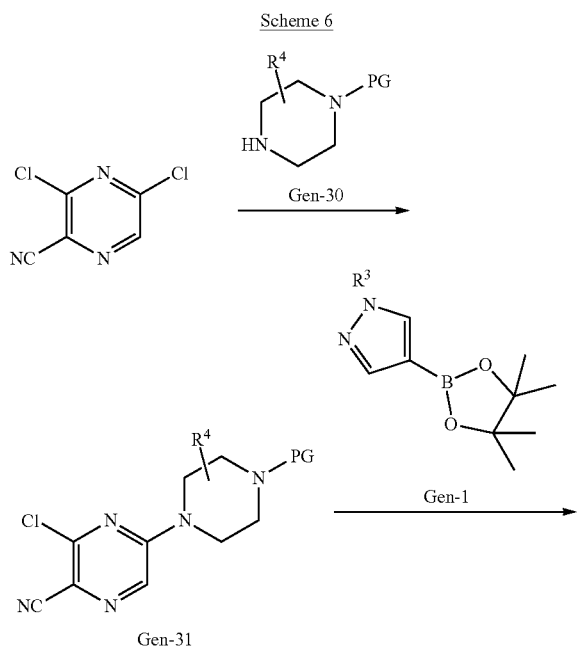

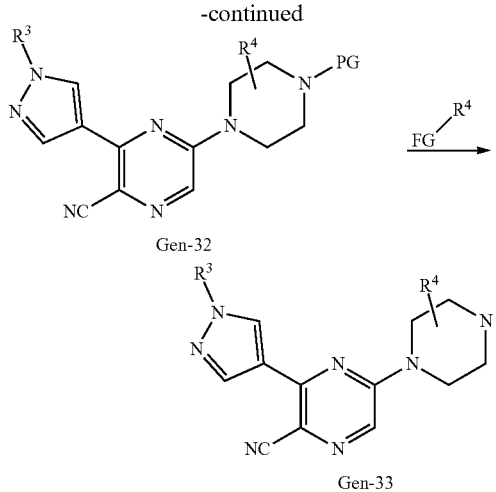

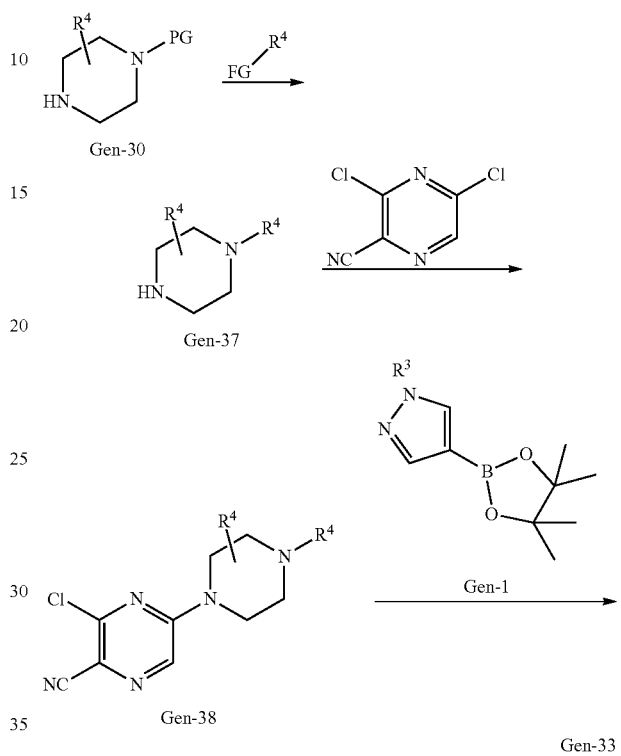

tion of iodomethane (CH₃I) to provide activated intermediate Gen-34, which could then engage with a nucleophile Gen-35 (where L=O or NH) to provide the corresponding ureas or carbamates Gen-36.

In another approach, a commercially-available protected substituted diamine Gen-30 can be engaged in a nucleophilic aromatic substitution reaction with 3,5-dichloropyrazine-2-carbonitrile to provide Gen-31. Gen-31 could then engage in a cross-coupling reaction (for example a palladium-catalyzed reaction) with Gen-1 to provide Gen-32. Gen-32 could be deprotected using standard conditions (for example, if PG=Boc, then the compound can be deprotected using acidic conditions such as TFA), and the resulting free secondary amine could be functionalized with an appropriately-substituted R⁴ to provide Gen-33. For example, in some cases, the amine can be engaged in an amide coupling reaction with a carboxylic acid to provide the corresponding amide.

In an alternative approach, a commercially-available protected substituted diamine Gen-30 could be deprotected (for example a Boc group could be removed under acidic conditions) and functionalized with an appropriately-substituted R⁴ (for example an amide coupling under standard conditions) to provide Gen-37. Gen-37 could then undergo a nucleophilic aromatic substitution reaction with 3,5-dichloropyrazine-2-carbonitrile to provide Gen-38. Gen-38 could then engage with Gen-1 as described above to provide Gen-33.

Example 1

5-[1-(cyclopropylmethyl)-2-oxo-1,8-diazaspiro[4.5]dec-8-yl]-3-(1-methyl-1H-pyrazol-4-yl)pyrazine-2-carbonitrile (1-1)

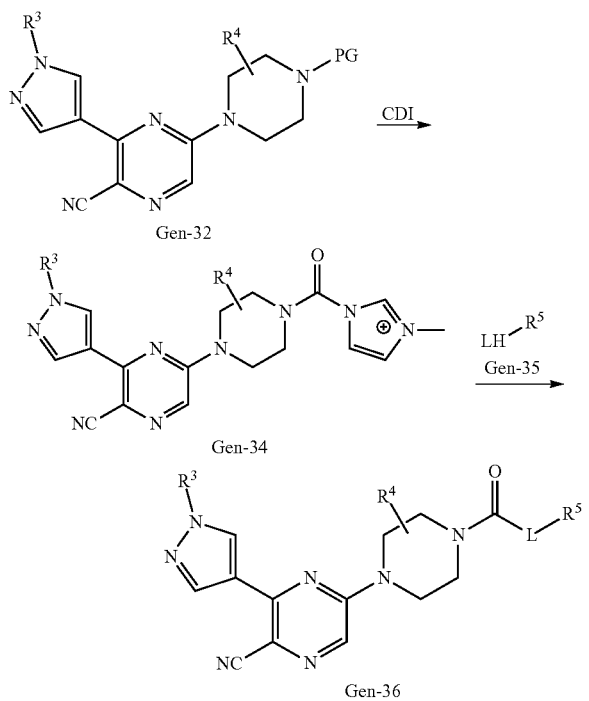

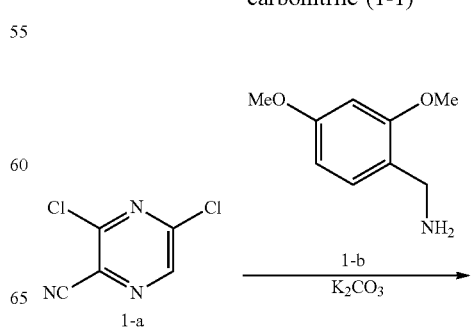

In a related approach, Gen-32 could be deprotected and then reacted with CDI and further methylated by the addi- -continued

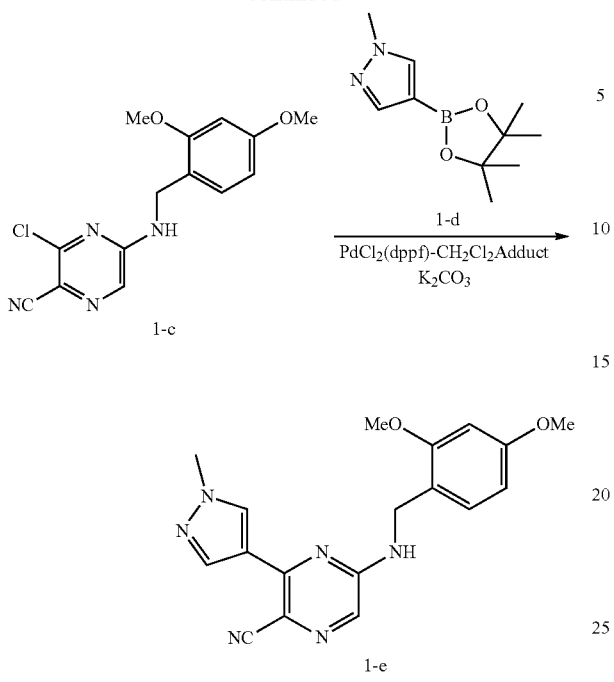

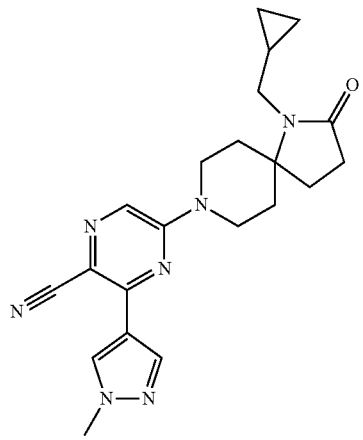

Step 1 3-chloro-5-((2,4-dimethoxybenzyl)amino) pyrazine-2-carbonitrile (1-c)

3,5-dichloropyrazine-2-carbonitrile (commercially available from Ark Pharm, Inc., Arlington Heights, Ill., USA) (1-a)(5.0 g, 29 mmol) and potassium carbonate ($K_2CO_3$) (7.9 g, 58 mmol) in DMF (31 mL) was cooled to 0° C., and to the mixture was added (2,4-dimethoxyphenyl)methanamine (commercially available from Oakwood Chemical, Estill, S.C., USA)(1-b) (4.3 mL, 29 mmol). The reaction was allowed to stir for 30 min, after which the reaction mixture was diluted with water (200 mL), and the aqueous layer was extracted with EtOAc (2×70 mL). The combined organic layers were dried over sodium sulfate and concentrated in vacuo to afford an oil. The crude oil was purified by column chromatography (silica gel, eluting with EtOAc/hexanes (0-60%/to afford 3-chloro-5-((2,4-dimethoxybenzyl)amino) pyrazine-2-carbonitrile (1-c). MS (ESI) Calc'd for ($C_{14}H_{14}ClN_4O_2$) [M+H]$^+$, 305; found, 305.

Step 2 5-((2,4-dimethoxybenzyl)amino)-3-(1-methyl-1H-pyrazol-4-yl)pyrazine-2-carbonitrile (1-e)

To 3-chloro-5-((2,4-dimethoxybenzyl)amino)pyrazine-2-carbonitrile (1-c) (7.0 g, 23 mmol), 1-methyl-4-(4,4,5,5-tetramethyl-1,3,2-dioxaborolan-2-yl)-1H-pyrazole (commercially available from TCI America. Portland, Oreg., USA) (1-d) (6.2 g, 30 mmol), potassium carbonate (6.35 g, 45.9 mmol) and PdCl$_2$(dppf)-CH$_2$Cl$_2$ (2.4 g, 3.0 mmol) in a flask was added dioxane (75 mL) and water (15 mL). The resulting mixture was degassed with nitrogen for 5 min, after which the reaction was then heated to 90° C. for 6 h. The reaction was then cooled to RT and diluted with water (200 mL). The aqueous layer extracted with EtOAc (2×70 mL), and the combined organic layers were dried over sodium sulfate and concentrated in vacuo. The crude residue was purified by column chromatography (silica gel, eluting with EtOAc/hexanes (30-100% by volume) to afford 5-((2,4-dimethoxybenzyl)amino)-3-(1-methyl-1H-pyrazol-4-yl) pyrazine-2-carbonitrile (1-e). MS (ESI) Calc'd for ($C_{18}H_{19}N_6O_2$) [M+H]$^+$, 351; found, 351.

Steps 3 and 4 5-chloro-3-(1-methyl-1H-pyrazol-4-yl)pyrazine-2-carbonitrile (1-IA)

To 5-((2,4-dimethoxybenzyl)amino)-3-(1-methyl-1H-pyrazol-4-yl)pyrazine-2-carbonitrile (1-e) (7.0 g, 20 mmol) in DCM (100 mL) was added TFA (7.7 mL, 100 mmol). The reaction was stirred at RT for 40 min, after which the solvent was removed in vacuo. To the residue was added 0.5 M of NaOH to (adjust to pH=12) and then the mixture was diluted with water to total volume to 300 mL with stirring. The formed precipitate was collected by filtration and washed with water. The cake was further dried under vacuum (nitrogen flow) overnight to give 5-amino-3-(1-methyl-1H-pyrazol-4-yl)pyrazine-2-carbonitrile which was used directly for next step without further purification.

To 5-amino-3-(1-methyl-1H-pyrazol-4-yl)pyrazine-2-carbonitrile (3.37 g, 16.8 mmol) and TBACl (14 g, 50.5 mmol) in DCM (84 mL) was added tert-butyl nitrite (tBuONO) (12.0 mL, 101 mmol). The mixture was stirred at RT for 6 h, after which saturated, aqueous NaHCO$_3$ was added and the resulting mixture was extracted with DCM (5×70 mL). The combined organic layers were dried over sodium sulfate and concentrated in vacuo. The residue was purified by column chromatography (silica gel, eluting with EtOAc/hexanes (0-60%)) to afford 1 5-chloro-3-(1-methyl-1H-pyrazol-4-yl)pyrazine-2-carbonitrile (1-IA). MS (ESI) Calc'd for (C$_9$H$_7$ClN$_5$) [M+H]$^+$, 220; found, 220.

Step 5: 3-(1-Methyl-1H-pyrazol-4-yl)-5-(2-oxo-1,8-diazaspiro[4.5]decan-8-yl)pyrazine-2-carbonitrile (1-IB)

A suspension of 1-IA (317 mg, 1.44 mmol), 1,8-diazaspiro[4.5]decan-2-one-2HCl (commercially available from Sigma-Aldrich, St. Louis, Mo., USA) (1-f) (400 mg, 1.76 mmol) in dioxane (10 mL) was treated with TEA (0.20 ml, 1.4 mmol) and stirred overnight at 50° C. The mixture was cooled to RT, diluted with 3:1 DCM/MeOH and washed with water. Organic layer was dried (Na$_2$SO$_4$) and concentrated. The residue was suspended in MeCN and filtered to collect the desired product (1-IB). MS (ESI) Calc'd for (C$_{17}$H$_{20}$N$_7$O) [M+H]$^+$, 338; found, 338.

Step 6 5-[1-(cyclopropylmethyl)-2-oxo-1,8-diazaspiro[4.5]dec-8-yl]-3-(1-methyl-1H-pyrazol-4-yl)pyrazine-2-carbonitrile (1-1)

A solution of Intermediate (1-IB) (30 mg, 0.089 mmol) in NMP (1 mL) was treated with a 60% suspension of sodium hydride (NaH) in mineral oil (8 mg, 0.2 mmol) and stirred for 20 min. Next, (bromomethyl)cyclopropane (1-g). (40 mg, 0.30 mmol) was added and the reaction mixture stirred for 6 hours. The reaction mixture was filtered and the filtrate purified by reverse phase chromatography (gradient of MeCN/water with 0.1% TFA) to provide compound 1-1 as a TFA salt. $^1$H NMR (600 MHz, DMSO-d$_6$) δ 8.44 (s, 1H), 8.28 (s, 1H), 8.10 (s, 1H), 4.13 (br, 2H), 3.89 (s, 3H), 3.09 (m, 2H), 2.90 (m, 2H), 2.27 (m, 2H), 2.02 (m, 2H), 1.85 (m, 2H), 1.52 (m, 2H), 0.86 (m, 1H), 0.33 (m, 2H), 0.16 (m, 2H). MS (ESI) Calc'd for (C$_{21}$H$_{26}$N$_7$O) [M+H]$^+$, 392; found, 392.

Example 2

5-{1-[(3-methyloxetan-3-yl)methyl]-2-oxo-3-oxa-1,8-diazaspiro[4.5]dec-8-yl}-3-(1-methyl-1H-pyrazol-4-yl)pyrazine-2-carbonitrile (1-2)

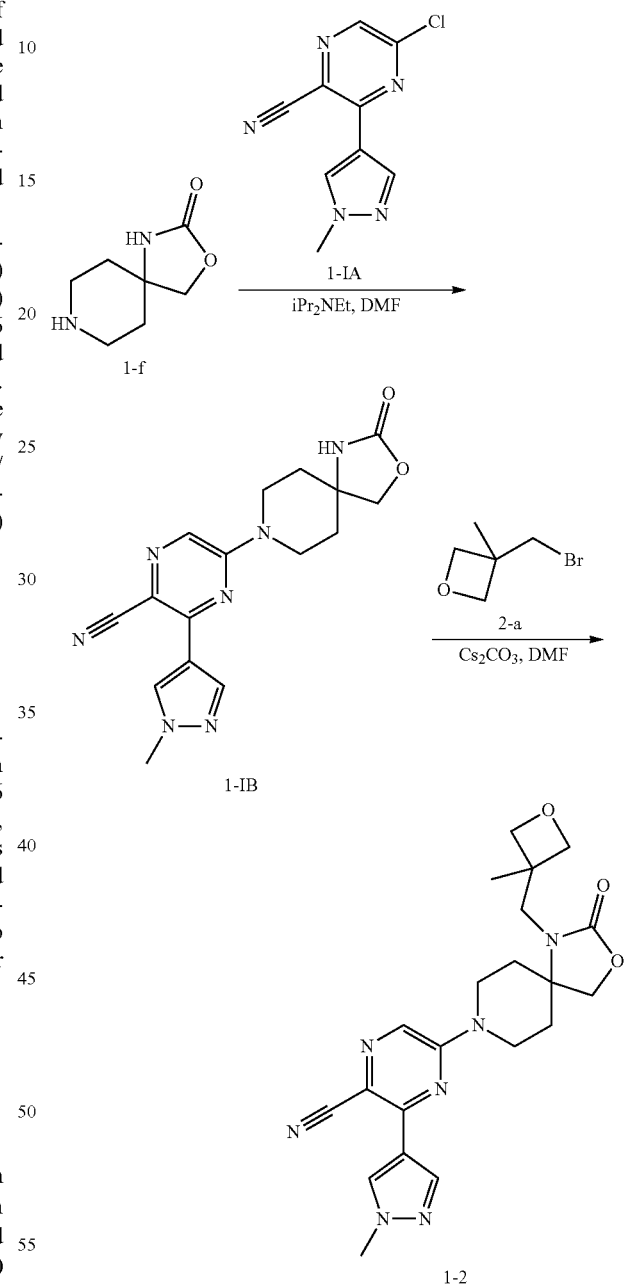

Step 1 3-(1-Methyl-1H-pyrazol-4-yl)-5-(2-oxo-3-oxa-1,8-diazaspiro[4.5]decan-8-yl)pyrazine-2-carbonitrile (1-IB)

A mixture of compound 1-IA (1.53 g, 6.97 mmol), 3-oxa-1,8-diazaspiro[4.5]decan-2-one (1-f) (1.4 g, 9.0 mmol), and i-Pr$_2$NEt (4.0 mL, 23 mmol) in DMF (60 mL) was stirred for 2 h. The mixture was then concentrated, then suspended in DCM, MeOH and water, and finally filtered to collect the desired product (1-IB). MS (ESI) Calc'd for ($C_{16}H_{18}N_7O_2$) [M+H]$^+$, 340; found, 340.

Step 2 5-{1-[(3-methyloxetan-3-yl)methyl]-2-oxo-3-oxa-1,8-diazaspiro[4,5]dec-8-yl}-3-(1-methyl-1H-pyrazol-4-yl)pyrazine-2-carbonitrile (1-2)

A solution of 3-(1-methyl-1H-pyrazol-4-yl)-5-(2-oxo-3-oxa-1,8-diazaspiro[4.5]decan-8-yl)pyrazine-2-carbonitrile (1-IB) (35 mg, 0.10 mmol) in DMF (1 mL) was treated with cesium carbonate ($Cs_2CO_3$) (100 mg, 0.31 mmol) and 3-(bromomethyl)-3-methyloxetane (2-a) (50 mg, 0.30 mmol). The mixture was stirred overnight at 6° C. The mixture was then cooled to RT, filtered, then purified by mass-directed reverse phase chromatography (gradient of MeCN/water with 0.1% $NH_4OH$) to provide compound 1-6. $^1$H NMR (600 MHz, DMSO-d$_6$) δ 8.42 (s, 1H), 8.28 (s, 1H), 8.10 (s, 1H), 4.62 (m, 2H), 4.45 (m, 2H), 4.34 (m, 2H), 4.00 (m, 2H), 3.90 (s, 3H), 3.16 (m, 2H), 3.00 (m, 2H), 1.79 (m, 2H), 1.65 (m, 2H), 1.20 (s, 3H). MS (ESI) Calc'd for ($C_{21}H_{26}N_7O_3$) [M+H]$^+$, 424; found, 424.

Example 3

5-[1-(cyclopropylmethyl)-2-oxo-1,3,8-triazaspiro[4.5]dec-8-yl]-3-(1-methyl-1H-pyrazol-4-yl)pyrazine-2-carbonitrile (1-3)

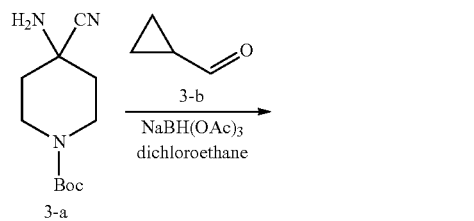

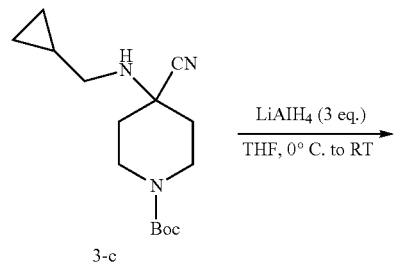

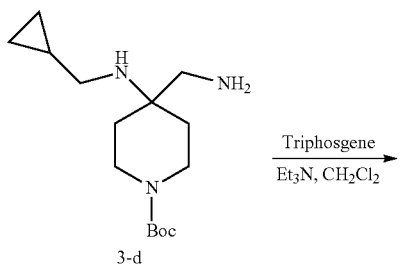

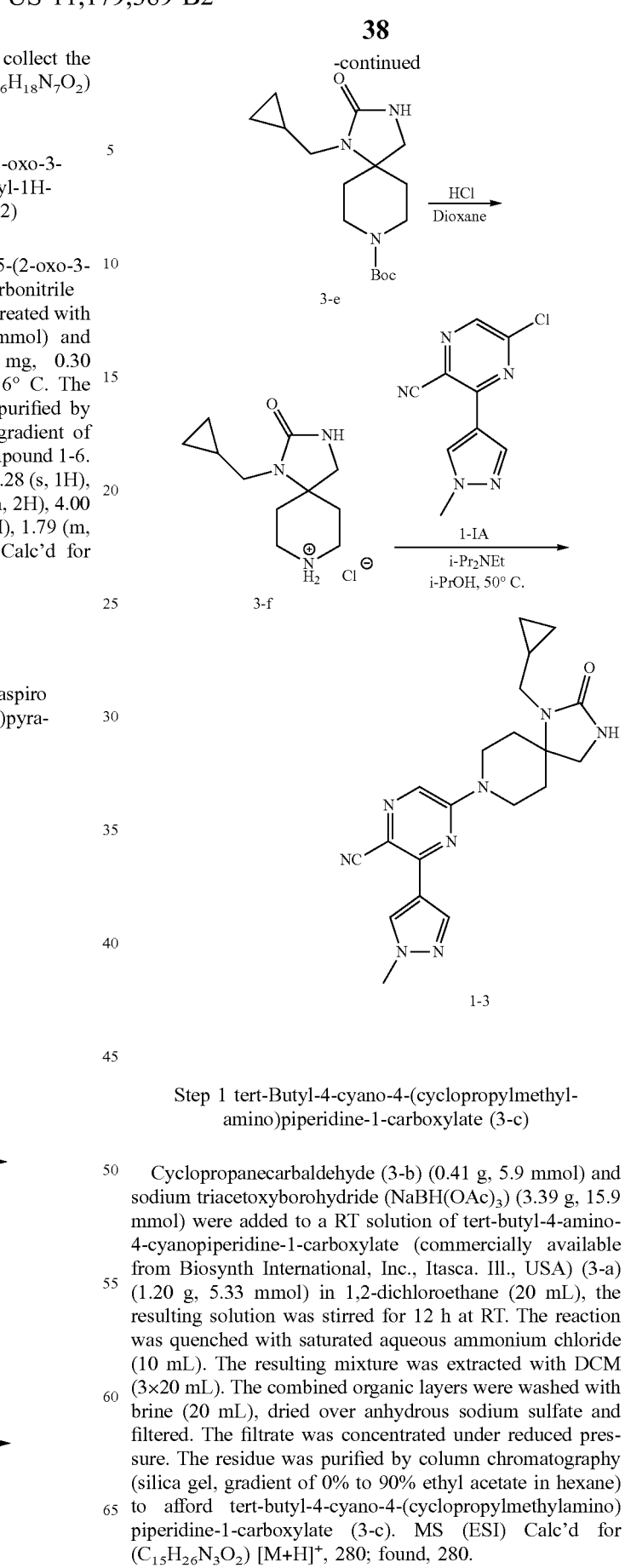

Step 1 tert-Butyl-4-cyano-4-(cyclopropylmethylamino)piperidine-1-carboxylate (3-c)

Cyclopropanecarbaldehyde (3-b) (0.41 g, 5.9 mmol) and sodium triacetoxyborohydride (NaBH(OAc)$_3$) (3.39 g, 15.9 mmol) were added to a RT solution of tert-butyl-4-amino-4-cyanopiperidine-1-carboxylate (commercially available from Biosynth International, Inc., Itasca. Ill., USA) (3-a) (1.20 g, 5.33 mmol) in 1,2-dichloroethane (20 mL), the resulting solution was stirred for 12 h at RT. The reaction was quenched with saturated aqueous ammonium chloride (10 mL). The resulting mixture was extracted with DCM (3×20 mL). The combined organic layers were washed with brine (20 mL), dried over anhydrous sodium sulfate and filtered. The filtrate was concentrated under reduced pressure. The residue was purified by column chromatography (silica gel, gradient of 0% to 90% ethyl acetate in hexane) to afford tert-butyl-4-cyano-4-(cyclopropylmethylamino)piperidine-1-carboxylate (3-c). MS (ESI) Calc'd for ($C_{15}H_{26}N_3O_2$) [M+H]$^+$, 280; found, 280.

Step 2 tert-Butyl-4-(aminomethyl)-4-(cyclopropylmethylamino)piperidine-1-carboxylate (3-d)

To a solution of tert-butyl-4-cyano-4-((cyclopropylmethyl)amino)piperidine-1-carboxylate (3-c) (1.10 g, 3.94 mmol) in tetrahydrofuran (10 mL) was added lithium aluminium hydride (LiAlH$_4$)(0.45 g, 11.8 mmol) at 0° C. The resulting mixture was stirred for 2 h at 0° C. The reaction mixture was quenched with sodium sulphate decahydrate (5 g) and stirred for another 30 min at RT. The resulting mixture was filtered through Celite™ and the filter cake was washed with DCM (10 mL). The filtrate was concentrated under reduced pressure to afford tert-butyl-4-(aminomethyl)-4-((cyclopropylmethyl)amino)piperidine-1-carboxylate (3-d) which was and used in the next step directly without further purification. MS (ESI) Calc'd for (C$_{15}$H$_{30}$N$_3$O$_2$) [M+H]$^+$, 284; found, 284.

Step 3 tert-butyl-1-(cyclopropylmethyl)-2-oxo-1,3,8-triazaspiro[4.5]decane-8-carboxylate (3-e)

To a 0° C. solution of tert-butyl-4-(aminomethyl)-4-((cyclopropylmethyl)amino) piperidine-1-carboxylate (3-c) (50 mg, 0.12 mmol) in DCM (3 mL) was added triphosgene (14.7 mg, 0.05 mmol) and trimethylamine (Et$_3$N) (0.09 mL, 0.62 mmol). The resulting mixture was stirred for 0.5 h at RT. The reaction mixture was then quenched with saturated aqueous ammonium chloride (10 mL). The resulting solution was extracted with DCM (3×10 mL). The combined organic layers were washed with brine (10 mL), dried over anhydrous sodium sulfate and filtered. The filtrate was concentrated under reduced pressure to afford tert-butyl-1-(cyclopropylmethyl)-2-oxo-1,3,8-triazaspiro[4.5]decane-8-carboxylate (3-e), which was used to next step directly without further purification. MS (ESI) Calc'd for (C$_{16}$H$_{28}$N$_3$O$_3$) [M+H]$^+$, 310; found, 310.

Step 4 1-(Cyclopropylmethyl)-1,3,8-triazaspiro[4.5]decan-2-one hydrochloride (3-f)

To a solution HCl/dioxane (4 M, 5 mL) was added tert-butyl-1-(cyclopropylmethyl)-2-oxo-1,3,8-triazaspiro[4.5]decane-8-carboxylate (3-e) (130 mg, 0.29 mmol). The reaction was stirred for 1 h at RT. The resulting was concentrated under reduced pressure to afford 1-(cyclopropylmethyl)-1,3,8-triazaspiro[4.5]decan-2-one (3-f), which was used in the next step directly without further purification. MS (ESI) calc'd for (C$_{11}$H$_{20}$N$_3$O) [M+H]$^+$, 210; found, 210.

Step 5 5-[1-(cyclopropylmethyl)-2-oxo-1,3,8-triazaspiro[4.5]dec-8-yl]-3-(1-methyl-1H-pyrazol-4-yl)pyrazine-2-carbonitrile (1-3)

To a RT solution of 1-(cyclopropylmethyl)-1,3,8-triazaspiro[4.5]decan-2-one hydrochloride (3-f) (50 mg, 0.14 mmol) in 2-propanol (3 mL) were added N,N-diisopropylethylamine (i-Pr$_2$NEt) (0.12 mL, 0.71 mmol) and compound 1-IA (31.3 mg, 0.142 mmol). The resulting solution was stirred for 3 h at 50° C. After cooling to RT, the reaction solution was concentrated under reduced pressure. The residue was purified by C18 column (Column: XBridge™ Prep C18 OBD Column 19*250 mm 10 μm (Waters Corporation, Milford, Mass., USA); Mobile Phase A: water (10 mmol/L NH$_4$HCO$_3$), Mobile Phase B: ACN; Flow rate: 25 mL/min; Gradient: 20% B to 60% B in 8 min) to afford compound 1-3. $^1$H NMR (300 MHz, DMSO-d6): δ: 8.46 (s, 1H), 8.31 (s, 1H), 8.14 (s, 1H), 6.36 (s, 1H), 4.64-4.63 (m, 2H), 3.94 (s, 3H), 3.32 (s, 2H), 3.07-3.03 (m, 2H), 2.84-2.82 (m, 2H), 1.90-1.83 (m, 2H), 1.64-1.60 (m, 2H), 0.91-0.86 (m, 1H), 0.38-0.34 (m, 2H), 0.15-0.10 (m, 2H). MS (ESI) calc'd for (C$_{20}$H$_{25}$N$_8$O) [M+H]$^+$, 392; found, 393.

Example 4

5-{1-(cyclopropylmethyl)-3-[2-(dimethylamino)ethyl]-2-oxo-1,3,8-triazaspiro[4.5]dec-8-yl}-3-(1-methyl-1H-pyrazol-4-yl)pyrazine-2-carbonitrile (1-4)

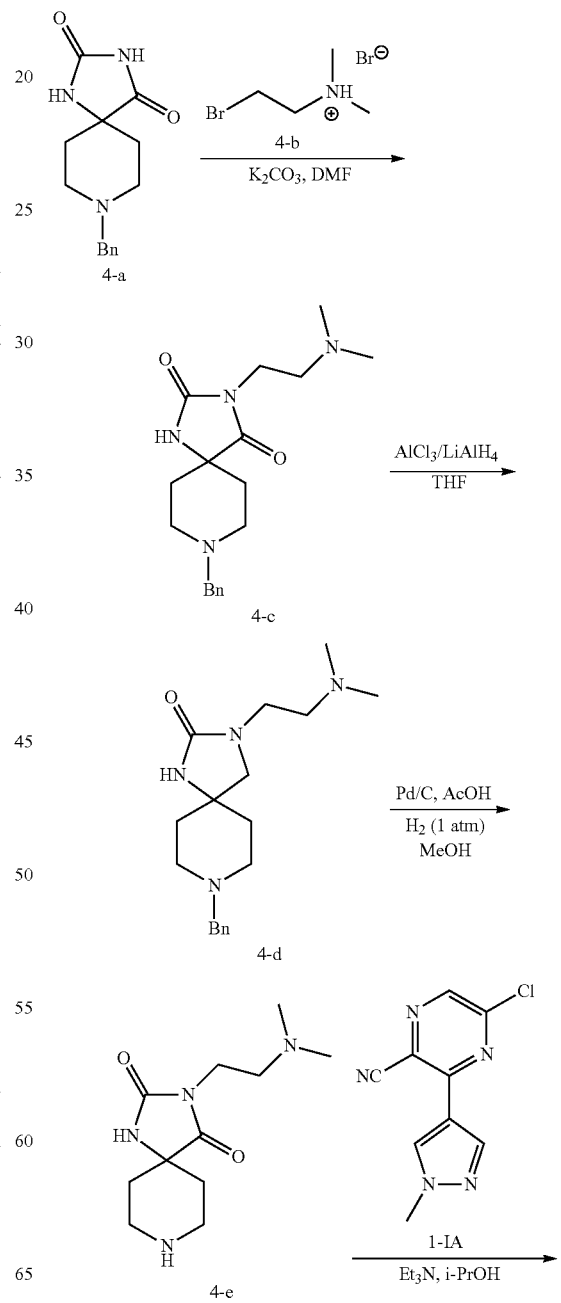

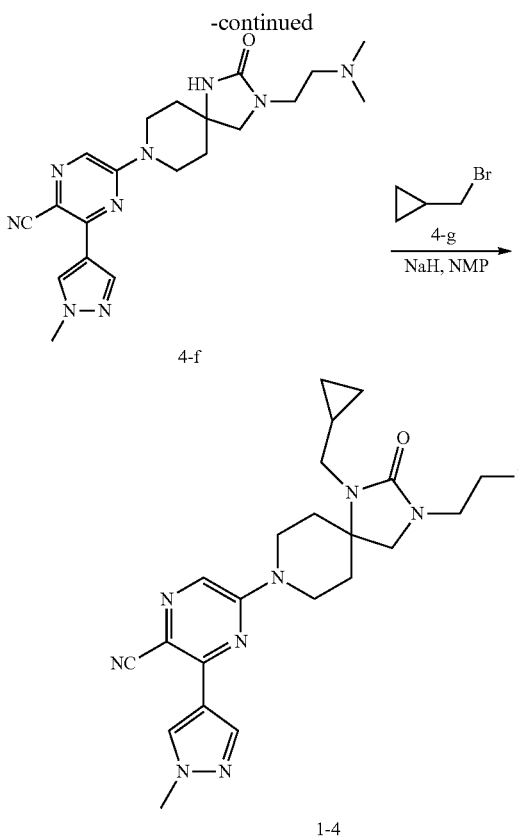

Step 1 8-Benzyl-3-(2-(dimethylamino)ethy)-1,3,8-triazaspiro[4.5]decane-2,4-dione (4-c)

To a RT solution of 8-benzyl-1,3,8-triazaspiro[4.5]decane-2,4-dione (4-a) (1.00 g, 3.86 mmol) (prepared according to the same procedure as described in the *Journal of Medicinal Chemistry* 2002, 45, 3972) in N,N-dimethylformamide (15 mL) were added 2-bromo-N,N-dimethylethanamine hydrobromide (4-b) (1.35 g, 5.78 mmol) and potassium carbonate (2.13 g, 15.4 mmol). The reaction mixture was stirred for 12 h 40° C. and then heated at 70° C. for another 2 h. After cooling to RT, the reaction mixture was filtered. The solids were washed with N N-dimethylformamide (15 mL). The combined filtrate was concentrated under reduced pressure. The residue was purified by Prep-HPLC (Column: XBridge™ C18 OBD Prep Column, 100 Å, 5 μm, 19 mm×250 mm (Waters Corporation, Milford, Mass., USA); Mobile Phase A: water (10 mmol/L $NH_4HCO_3$), Mobile Phase B: ACN; Flow rate: 20 mL/min; Gradient: 20% B to 60% B in 8 min to afford 8-benzyl-3-(2-(dimethylamino)ethyl)-1,3,8-triazaspiro[4.5]decane-2,4-dione (4-c). MS (ESI) Calc'd for $(C_{18}H_{27}N_4O_2)$ $[M+H]^+$, 331; found, 331.

Step 2 8-Benzyl-3-(2-(dimethylamino)ethyl)-1,3,8-triazaspiro[4.5]decan-2-one (4-d)

To a 0° C. solution of 8-benzyl-3-(2-(dimethylamino)ethyl)-1,3,8-triazaspiro[4.5]decane-2,4-dione (4-c) (0.500 g, 1.51 mmol) in THF (10 mL) was added aluminum chloride ($AiCl_3$) (0.81 g, 6.1 mmol) and the mixture was stirred for 10 min at 0° C. Lithium aluminium hydride ($LiAlH_4$) (172 mg, 4.54 mmol) was added to the above mixture at 0° C. The resulting mixture was stirred for 3 h at RT. The reaction mixture was quenched with methanol (5 mL), filtered, and the solids washed with methanol (20 mL). The filtrate was concentrated under reduced pressure. The residue was purified by column chromatography (silica gel; gradient of 0% to 10% methanol in dichloromethane as eluent) to afford 8-benzyl-3-(2-(dimethylamino)ethyl)-1,3,8-triazaspiro[4.5]decan-2-one (4-d) which was used in the next step directly without further purification. MS (ESI) Calc'd for $(C_{18}H_{29}N_4O)$ $[M+H]^+$, 371; found, 371.

Step 3 3-(2-(Dimethylamino)ethyl)-1,3,8-triazaspiro[4.5]decan-2-one (4-e)

To a RT solution of 8-benzyl-3-(2-(dimethylamino)ethyl)-1,3,8-triazaspiro[4.5]decan-2-one (4-d) (100 mg, 0.32 mmol) in methanol (5 mL) were added Pd/C (palladium on carbon)(34 mg, 0.03 mmol, 10% wt/wt) and acetic acid (1.8 μl, 0.03 mmol). The resulting mixture was stirred for 3 h at RT under an atmosphere of hydrogen (balloon). The mixture was filtered through Celite™ and washed with methanol (MeOH) (5 mL). The filtrate was concentrated under reduced pressure to afford 3-(2-(dimethylamino)ethyl)-1,3,8-triazaspiro[4.5]decan-2-one (4-e) which was used in next step directly without further purification. MS (ESI) Calc'd for $(C_{11}H_{23}N_4O)$ $[M+H]^+$, 227; found, 227.

Step 4 5-(3-(2-(Dimethylamino)ethyl)-2-oxo-1,3,8-triazaspiro[4.5]decan-8-yl)-3-(1-methyl-1H-pyrazol-4-yl)pyrazine-2-carbonitrile (4-f)

To a RT solution of 3-(2-(dimethylamino)ethyl)-1,3,8-triazaspiro[4.5]decan-2-one (4-d) (100 mg, 0.44 mmol) (purity: 50%) in isopropanol (2 mL) was added 1-IA (78 mg, 0.35 mmol) and trimethylamine ($Et_3N$) (0.19 mL, 1.3 mmol). The resulting solution was stirred for 12 h at RT. The mixture was concentrated under reduced pressure. The residue was purified by a column chromatography (silica gel, using gradient of 0% to 10% methanol in DCM as eluent) to afford 5-(3-(2-(dimethylamino)ethyl)-2-oxo-1,3,8-triazaspiro[4.5]decan-8-yl)-3-(1-methyl-1H-pyrazol-4-yl)pyrazine-2-carbonitrile (4-f). MS (ESI) Calc'd for $(C_{20}H_{28}N_9O)$ $[M+H]^+$, 410; found, 410.

Step 5 5-{1-(cyclopropylmethyl)-3-[2-(dimethylamino)ethyl]-2-oxo-1,3,8-triazaspiro [4.5]dec-8-yl}-3-(1-methyl-1H-pyrazol-4-yl)pyrazine-2-carbonitrile (1-4)

To a 0° C. solution of 5-(3-(2-(dimethylamino)ethyl)-2-oxo-1,3,8-triazaspiro[4.5]decan-8-yl)-3-(1-methyl-1H-pyrazol-4-yl)pyrazine-2-carbonitrile (4-) (0.20 g, 0.49 mmol) in N-methylpyrrolidone (NMP) (3 mL) was added sodium hydride (NaH) (39.1 mg, 0.98 mmol, 60% wt/wt). The resulting mixture was stirred for 10 min at 0° C. Then bromomethylcyclopropane (4-g) (165 mg, 1.22 mmol) was added to the above mixture and stirred for 1 h at RT. The reaction mixture was quenched with water (15 mL) then extracted with dichloromethane (3×10 mL). The combined organic layers were washed with brine (10 mL), dried over anhydrous sodium sulfate and filtered. The filtrate was concentrated under reduced pressure. The residue was purified by Prep-HPLC (Column: XBridge™ Prep Shield RP18 OBD Column 19*150 mm, 5 um, 13 nm (Waters Corporation, Milford, Mass., USA); Mobile Phase A: water (10 mmol/L $NH_4HCO_3$) Mobile Phase B: ACN; Flow rate: 20 mL/min; Gradient: 25% B to 40% B in 8 min) to afford compound 1-4. $^1$H NMR (300 MHz, DMSO-$d_6$): δ 8.46 (s, 1H), 8.32 (s, 1H), 8.15 (s, 1H), 4.65 (s, 2H), 3.94 (s, 3H), 3.39 (s, 2H), 3.21-3.19 (m, 2H), 3.12-3.04 (m, 2H), 2.85 (d, J=6.9 Hz, 2H), 2.36 (t, J=6.9 Hz, 2H), 2.17 (s, 6H), 1.91-1.84 (m, 2H), 1.60-1.56 (m, 2H), 0.93-0.89 (m, 1H), 0.38-0.36 (m, 2H), 0.16-0.12 (m, 2H). MS (ESI) Calc'd for ($C_{24}H_{34}N_9O$) [M+H]$^+$, 464; found, 464.
Example 5
5-{3-[2-(dimethylamino)ethyl]-2-oxo-1-(2,2,2-trifluoro-1-methylethyl)-1,3,8-triazaspiro[4.5]dec-8-yl}-3-(1-methyl-1H-pyrazol-4-yl)pyrazine-2-carbonitrile (1-5)
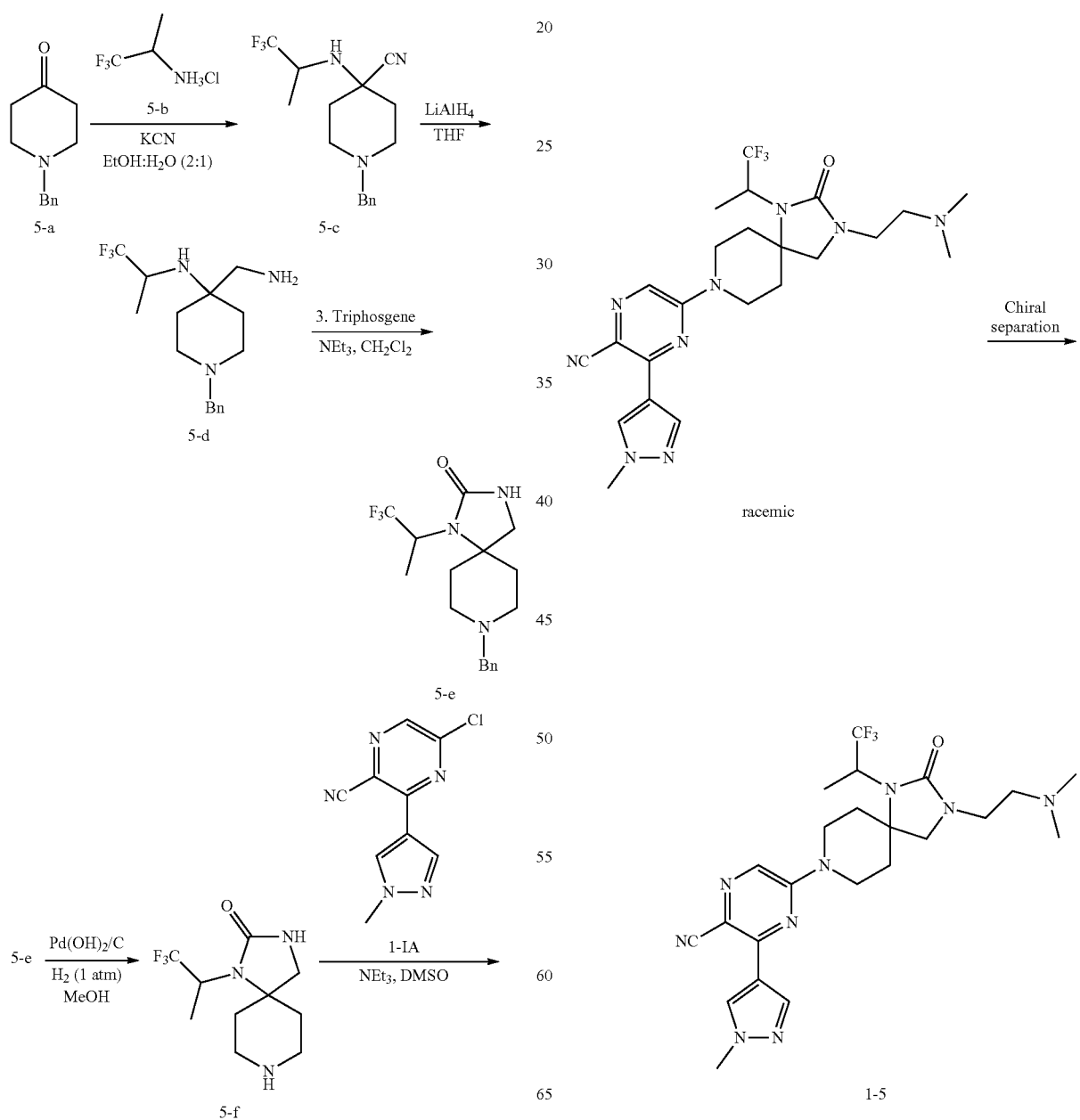

Step 1 1-Benzyl-4-(1,1,1-trifluoropropan-2-ylamino) piperidine-4-carbonitrile (5-c)

To a RT solution of 1-benzylpiperidin-4-one (commercially available from Sigma Aldrich, St. Louis, Mo., USA) (5-a) (3.00 g, 15.9 mmol) in ethanol (20 ml)/water (10 mL) was added 1,1,1-trifluoropropan-2-amine hydrochloride (commercially available from Sigma Aldrich, St. Louis, Mo. USA) (5-b) (3.56 g, 23.8 mml) and potassium cyanide (KCN) (1.55 g 23.8 mmol). The resulting solution was stirred for 24 h at 30° C. The reaction was quenched with saturated aqueous ferrous sulfate (20 mL). The resulting mixture was extracted with ethyl acetate (3×20 mL). The combined organic layers were washed with brine (50 mL) dried over anhydrous sodium sulfate and filtered. The filtrate was concentrated under reduced pressure. The residue was purified by flash column chromatography (silica gel) using gradient of 0% to 5% methanol in dichloromethane as an eluent to afford 1-benzyl-4-((1,1,1-trifluoropropan-2-yl) amino) piperidine-4-carbonitrile (5-c). MS (ESI) Calc'd for $(C_{16}H_{21}F_3N_3)$ [M+H]$^+$, 312; found, 312.

Step 2 4-(Aminomethyl)-1-benzyl-N-(1,1,1-trifluoropropan-2-yl)piperidin-4-amine (5-d)

To a 0° C. solution of 1-benzyl-4-((1,1,1-trifluoropropan-2-yl)amino)piperidine-4-carbonitrile (5-c) (2.00 g, 6.42 mmol) in tetrahydrofuran (THF) (20 mL) was added lithium aluminium hydride (LiAlH$_4$) (0.370 g, 9.64 mmol). The resulting mixture was stirred for 1 h at RT. The mixture was quenched via the addition of sodium sulphate decahydrate (5 g). The resulting mixture was filtered through Celite™ and the filter cake was washed with tetrahydrofuran (10 mL). The filtrate was concentrated under reduced pressure. The residue was purified by flash column chromatography (silica gel) using a gradient of 0% to 40% methanol in dichloromethane as the eluent to afford 4-(aminomethyl)-1-benzyl-N-(1,1,1-trifluoropropan-2-yl)piperidin-4-amine (5-d). MS (ESI) Calc'd for $(C_{16}H_{25}F_3N_3)$ [M+H]$^+$, 316; found, 316.

Step 3 8-Benzyl-1-(1,1,1-trifluoropropan-2-yl)-1,3,8-triazaspiro[4.5]decan-2-one (5-e)

To a 0° C. solution of 4-(aminomethyl)-1-benzyl-N-(1,1,1-trifluoropropan-2-yl)piperidin-4-amine (5-d) (0.70 g, 2.22 mmol) in dichloromethane (10 mL) were added triphosgene (0.26 g, 0.89 mmol) and trimethylamine (NEt) (0.93 mL, 6.66 mmol). The resulting mixture was stirred for 1 h at RT. The reaction was quenched with water (20 mL) then extracted with dichloromethane (3×20 mL). The combined organic layers were washed with brine (20 mL), dried over anhydrous sodium sulfate and filtered. The filtrate was concentrated under reduced pressure. The residue was purified by flash column chromatography (silica gel) using a gradient of 0% to 5% methanol in dichloromethane as eluent to afford 8-benzyl-1-(1,1,1-trifluoropropan-2-yl)-1,3,8-triazaspiro[4.5]decan-2-one (5-e). MS (ESI) Calc'd for $(C_{17}H_{23}F_3N_3O)$ [M+H]$^+$, 342; found, 342.

Step 4 1-(1,1,1-Trifluoropropan-2-yl)-1,3,8-triazaspiro[4.5]decan-2-one (5-f)

To a solution of 8-benzyl-1-(1,1,1-trifluoropropan-2-yl)-1,3,8-triazaspiro[4.5]decan-2-one (5-e) (100 mg, 0.29 mmol) in methanol (10 mL) was added Pd(OH)$_2$/C (20.6 mg, 0.03 mmol). The resulting mixture was placed under an atmosphere of hydrogen (balloon) and stirred for 1 h at RT. The resulting mixture was filtered through Celite™ and the filter cake was washed with methanol (5 mL). The filtrate was concentrated under reduced pressure to afford 1-(1,1,1-trifluoropropan-2-yl)-1,3,8-triazaspiro[4.5]decan-2-one, which was used directly without further purification (5-f). MS (ESI) Calc'd for $(C_{10}H_{17}F_3N_3O)$ [M+H]$^+$, 252; found, 252.

Step 5 3-(1-Methyl-1H-pyrazol-4-yl)-5-(2-oxo-1-(1,1,1-trifluoropropan-2-yl)-1,3,8-triazaspiro[4.5]decan-8-yl)pyrazine-2-carbonitrile (5-g)

To a solution of 1-(1,1,1-trifluoropropan-2-yl)-1,3,8-triazaspiro[4.5]decan-2-one (5-f) (60 mg, 0.24 mmol) in dimethylsulfoxide (DMSO) (2 mL) were added trimethylamine (NEt$_3$) (0.05 mL, 0.36 mmol) and intermediate 1-A (57.7 mg, 0.263 mmol). The resulting solution was heated to 80° C. and stirred for 2 h. After cooling to RT, water (10 mL) was added to the reaction mixture. The resulting mixture was extracted with ethyl acetate (3×5 mL). The combined organic layers were washed with brine (5 mL), dried over anhydrous sodium sulfate and filtered. The filtrate was concentrated under reduced pressure. The residue was purified by flash column chromatography (silica gel, using a gradient of 0% to 5% methanol in DCM as the eluent) to afford 3-(1-methyl-1H-pyrazol-4-yl)-5-(2-oxo-1-(1,1,1-trifluoropropan-2-yl)-1,3,8-triazaspiro[4.5]decan-8-yl) pyrazine-2-carbonitrile (5-g). MS (ESI) Calc'd for $(C_{19}H_{22}F_3N_8O)$ [M+H]$^+$, 435; found, 435.0.

Step 6 5-{3-[2-(dimethylamino)ethyl]-2-oxo-1-(2,2,2-trifluoro-1-methylethyl)-1,3,8-triazaspiro[4.5]dec-8-yl}-3-(1-methyl-1H-pyrazol-4-yl)pyrazine-2-carbonitrile (1-5)

To a 0° C. solution of 3-(1-methyl-1H-pyrazol-4-yl)-5-(2-oxo-1-(1,1,1-trifluoropropan-2-yl)-1,3,8-triazaspiro[4.5] decan-8-yl)pyrazine-2-carbonitrile (5-g) (80 mg, 0.18 mmol) in DMF (3 mL) was added sodium hydride (NaH) (22.1 mg, 0.550 mmol, 60% wt/wt). The resulting mixture was stirred for 15 min. Then 2-bromo-N,N-dimethylethanamine hydrobromide (5-h) (64.3 mg, 0.280 mmol) was added to the above mixture. The resulting mixture was stirred for 2 h at RT. The reaction was quenched with water (10 mL) and the resulting solution was extracted with ethyl acetate (3×5 mL). The combined organic layers were washed with brine (5 mL), dried over anhydrous sodium sulfate and filtered. The filtrate was concentrated under reduced pressure. The residue was purified by flash column chromatography (silica gel, eluting with a gradient of 0% to 15% MeOH in DCM) to afford racemic 5-(3-(2-(dimethylamino)ethyl)-2-oxo-1-(1,1,1-trifluoropropan-2-yl)-1,3,8-triazaspiro[4.5]decan-8-yl)-3-(1-methyl-1H-pyrazol-4-yl) pyrazine-2-carbonitrile (racemic). The solid was purified by Prep-Chiral-HPLC (Column: Chiralpak® IA, 2*25 cm, 5 um (Chiral Technologies Inc, Daicel Group, West Chester, Pa. USA); Mobile Phase A:MTBE (0.1% DEA)-HPLC, Mobile Phase B: MeOH-HPLC; Flow rate: 20 mL/min; Gradient: 8% B isocratic) to give compound 1-5 (faster eluting isomer, 11 min). $^1$H NMR (300 MHz, CDCl$_3$): δ: 8.30 (s, 1H), 8.21 (s, 1H), 8.01 (s, 1H), 4.66-4.62 (m, 2H), 3.99 (s, 3H), 3.71-3.50 (m, 3H), 3.37-2.93 (m, 4H), 2.61-2.56 (m, 2H), 2.35 (s, 6H), 1.96-1.88 (m, 3H), 1.80-1.70 (m, 1H), 1.60 (d, J=6.9 Hz, 3H). MS (ESI) Calc'd for $(C_{23}H_{31}F_3N_9O)$ [M+H]$^+$, 506.3; found, 506.0.

Example 6

5-[1-(cyclopropylmethyl)-2,2-dioxido-2-thia-1,3,8-triazaspiro[4.5]dec-8-yl]-3-(1-methyl-1H-pyrazol-4-yl)pyrazine-2-carbonitrile (1-6)

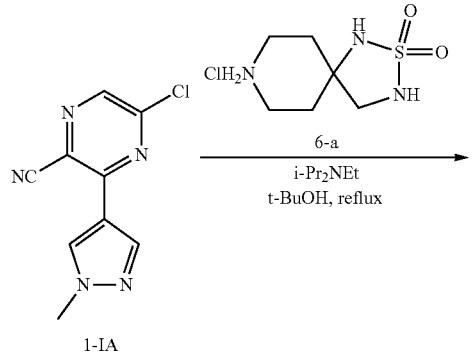

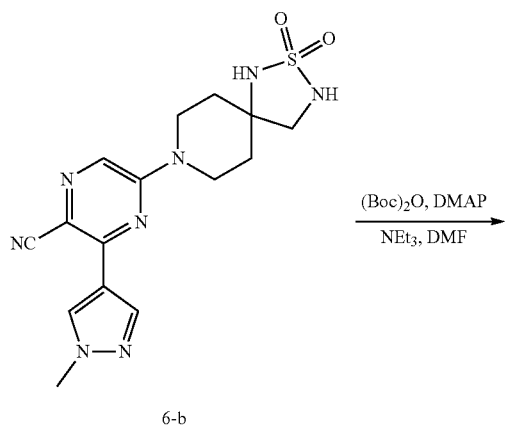

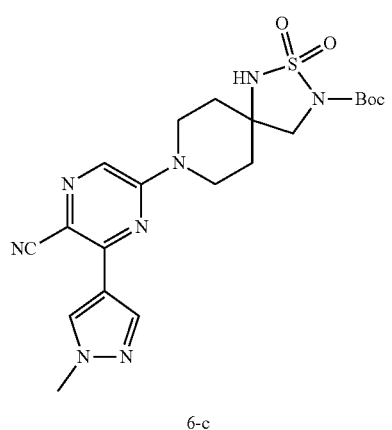

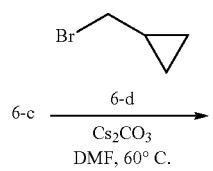

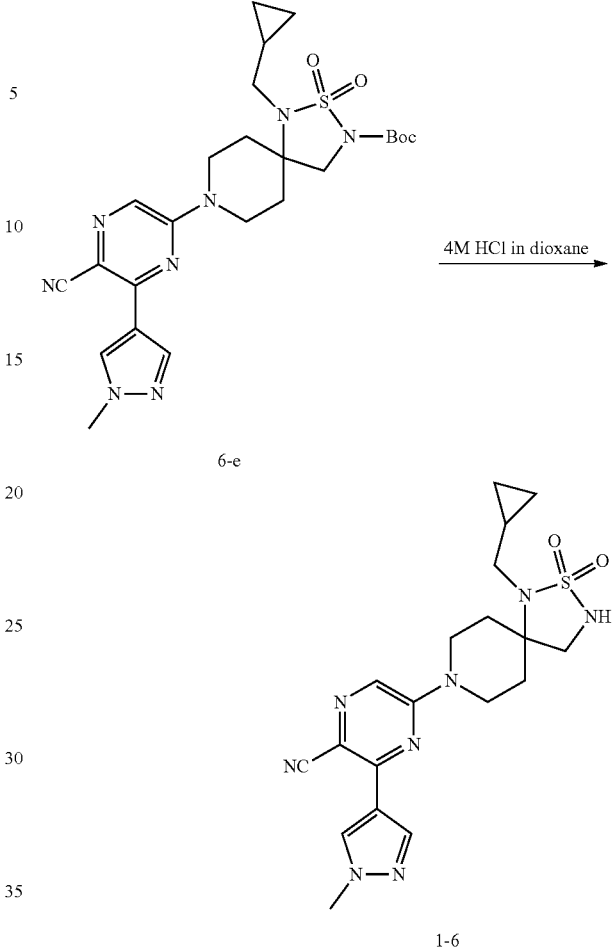

Step 1 5-(2,2-Dioxido-2-thia-1,3,8-triazaspiro[4.5]decan-8-yl)-3-(1-methyl-1H-pyrazol-4-yl)pyrazine-2-carbonitrile (6-b)

To a solution of 2-thia-1,3,8-triazaspiro[4.5]decane-2,2-dioxide hydrochloride (the free-base of which is commerically-available from Aurora Fine Chemicals LLC, 7929 Silverton Ave., Suite 609, San Diego, Calif., 92126, United States) (0.230 g, 1.00 mmol) in tert-butanol (t-BuOH) (5 mL) were added diisopropylethylamine (i-Pr$_2$NEt) (0.88 mL, 5.0 mmol) and intermediate 1-IA (0.220 g, 1.00 mmol). The resulting mixture was stirred for 16 h at 80° C. After cooling to RT, the reaction mixture was concentrated under reduced pressure. The residue was triturated with ethyl acetate (30 mL). The resulting solids were collected and dried to afford 5-(2,2-dioxido-2-thia-1,3,8-triazaspiro[4.5]decan-8-yl)-3-(1-methyl-1H-pyrazol-4-yl)pyrazine-2-carbonitrile (6-b), which was used directly in the next step without further purification. MS (ESI) Calc'd for (C$_{15}$H$_{19}$N$_8$O$_2$S) [M+H]$^+$, 375; found, 375.

Step 2 tert-Butyl-8-(5-cyano-6-(1-methyl-1H-pyrazol-4-yl)pyrazin-2-yl)-2-thia-1,3,8-triazaspiro[4.5]decane-3-carboxylate-2,2-dioxide (6-c)

To a solution of 5-(2,2-dioxido-2-thia-1,3,8-triazaspiro[4.5]decan-8-yl)-3-(1-methyl-1H-pyrazol-4-yl)pyrazine-2- carbonitrile (6-b) (0.24 mg, 0.64 mmol) in dichloromethane (15 mL) was added triethylamine (0.18 mL, 1.3 mmol), N,N-dimethylpyridin-4-amine (DMAP) (78 mg, 0.64 mmol) and di-tert-butyl dicarbonate ((Boc)$_2$O) (0.15 mL, 0.64 mmol). The resulting solution was stirred for 1 h at RT. The reaction was concentrated under reduced pressure. The residue was purified by preparative thin layer chromatography, eluting with petroleum ether: ethyl acetate (1.5:1) to afford tert-butyl-8-(5-cyano-6-(1-methyl-1H-pyrazol-4-yl)pyrazin-2-yl)-2-thia-1,3,8-triazaspiro[4.5]decane-3-carboxylate-2,2-dioxide (6-c). MS (ESI) Calc'd for (C$_{20}$H$_{27}$N$_8$O$_4$S) [M+H]$^+$, 475; found, 475.

Step 3 tert-Butyl-8-(5-cyano-6-(1-methyl-1H-pyrazol-4-yl)pyrazin-2-yl)-1-(cyclopropylmethyl)-2-thia-1,3,8-triazaspiro[4.5]decane-3-carboxylate-2,2-dioxide (6-e)

To a RT solution of tert-butyl-8-(5-cyano-6-(1-methyl-1H-pyrazol-4-yl)pyrazin-2-yl)-2-thia-1,3,8-triazaspiro[4.5]decane-3-carboxylate-2,2-dioxide (6-c) (100 mg, 0.210 mmol) in N,N-dimethylformamide (4 mL) was added cesium carbonate (Cs$_2$CO$_3$)(137 mg, 0.42 mmol) and (bromomethyl)-cyclopropane (6-d) (56.9 mg, 0.420 mmol). The resulting mixture was stirred for 4 h at 60° C. After cooling to RT, the reaction mixture was diluted with water (10 mL) and extracted with ethyl acetate (3×15 mL). The combined organic layers were washed with brine (2×10 mL), dried over anhydrous sodium sulfate and filtered. The filtrate was concentrated under reduced pressure. The residue was purified by preparative thin layer chromatography, eluting with petroleum ether:ethyl acetate (2:1) to afford tert-butyl-8-(5-cyano-6-(1-methyl-1H-pyrazol-4-yl) pyrazin-2-yl)-1-(cyclopropylmethyl)-2-thia-1,38-triazaspiro[4.5]decane-3-carboxylate-2,2-dioxide (6-e). MS (ESI) Calc'd for (C$_{24}$H$_{33}$N$_8$O$_4$S) [M+H]$^+$, 529; found, 529.

Step 4 5-[1-(cyclopropylmethyl)-2,2-dioxido-2-thia-1,3,8-triazaspiro[4.5]dec-8-yl]-3-(1-methyl-1H-pyrazol-4-yl)pyrazine-2-carbonitrile (1-6)

tert-Butyl-8-(5-cyano-6-(1-methyl-1H-pyrazol-4-yl) pyrazin-2-yl)-1-(cyclopropylmethyl)-2-thia-1,3,8-triazaspiro[4.5]decane-3-carboxylate-2,2-dioxide (6-e) (100 mg, 0.19 mmol) was added to a solution of hydrochloric acid in 1,4-dioxane (10 mL, 4 M). The reaction mixture was stirred for 16 h at RT then concentrated under reduced pressure. The resulting residue was diluted with ethyl acetate (5 mL) and the pH was adjusted to pH=8 with saturated sodium bicarbonate (10 mL). The mixture was extracted with ethyl acetate (3×10 mL). The combined organic layers were washed with brine (2×10 mL), dried over anhydrous sodium sulfate and filtered. The filtrate was concentrated under reduced pressure. The residue was purified by preparative thin layer chromatography, eluting with petroleum ether: ethyl acetate (1:1) to afford compound 1-6. $^1$H NMR (300 MHz, CDCl$_3$) δ 8.31 (s, 1H), 8.21 (s, 1H), 8.01 (s, 1H), 4.62 (d, J=13.8 Hz, 2H), 4.37-4.35 (m, 1H), 4.00 (s, 3H), 3.58 (d, J=6.8 Hz, 2H), 3.11-3.03 (m, 2H), 2.95-2.92 (m, 2H), 2.00-1.97 (m, 4H), 1.12-1.08 (m, 1H), 0.61-0.57 (m, 2H), 0.27-0.25 (m, 2H). MS (ESI) Calc'd for (C$_9$H$_{25}$N$_8$O$_2$S) [M+H]$^+$, 429; found, 429.

Example 7

5-[4-(cyclopropylmethyl)-2-oxo-3-oxa-1,8-diazaspiro[4.5]dec-8-yl]-3-(1-methyl-1H-pyrazol-4-yl)pyrazine-2-carbonitrile (1-7)

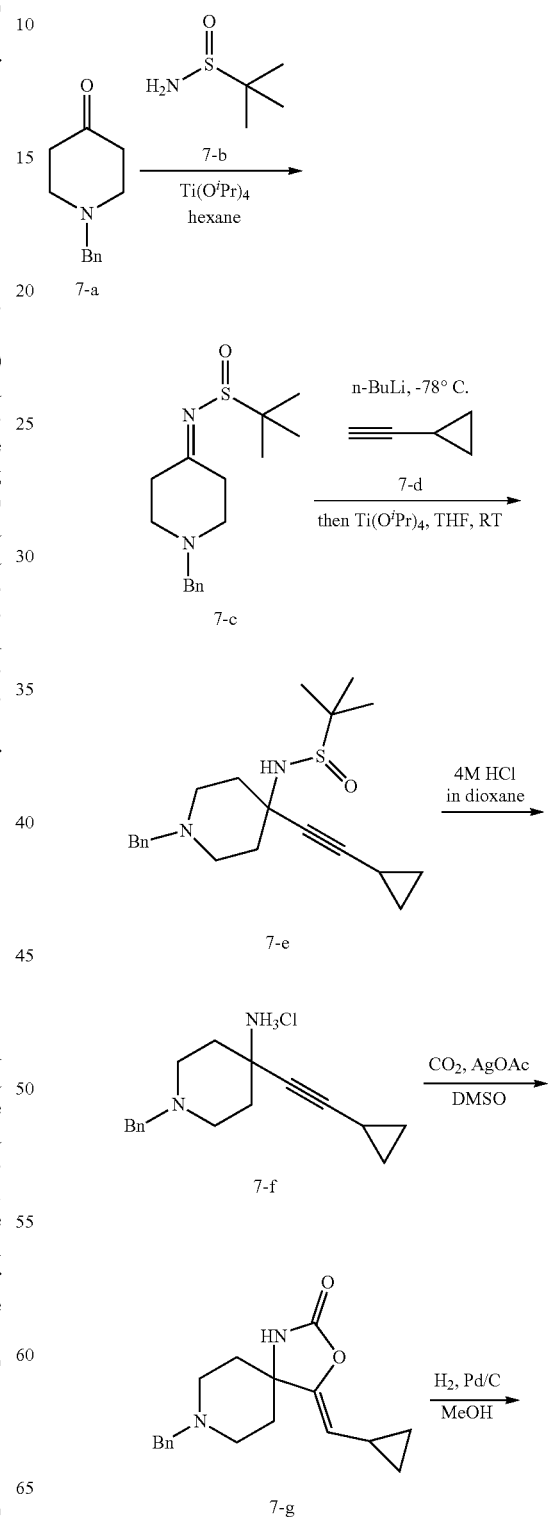

51
-continued

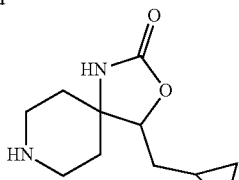

7-h

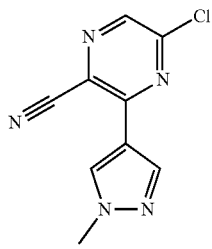

7-h →[1-IA][i-Pr₂NEt][t-BuOH, 80° C.]

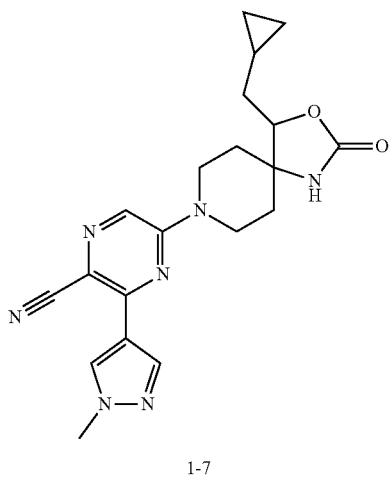

1-7

Step 1 N-(1-Benzylpiperidin-4-ylidene)-2-methylpropane-2-sulfinamide (7-c)

To a solution of 1-benzylpiperidin-4-one (commercially available from Sigma-Aldrich, St. Louis, Mo., USA) (7-a) (5.00 g, 26.4 mmol) in hexane (100 mL) was added 2-methylpropane-2-sulfinamide (7-b) (6.40 g, 52.8 mmol) and tetraisopropoxtitanium (Ti(O$^i$Pr)$_4$) (11.3 g, 39.6 mmol). The resulting mixture was stirred for 6 h at RT. The reaction as quenched with water (50 mL). The resulting mixture was filtered through Celite™ and the filter cake was washed with dichloromethane (10 mL). The organic layer was separated and the aqueous phase was extracted with dichloromethane (3×50 mL). The combined organic layers were washed with brine (30 mL), dried over anhydrous sodium sulfate and filtered. The filtrate was concentrated under reduced pressure and the resulting residue was purified via silica gel flash column chromatography, eluting with a gradient of 0% to 10% methanol in dichloromethane to afford N-(1-benzylpiperidin-4-ylidene)-2-methylpropane-2-sulfinamide (7-c) which used in the next step directly without further purification. MS (ESI) Calc'd for (C$_{16}$H$_{25}$N$_2$OS) [M+H]$^+$, 293; found, 293.

Step 2 N-(1-Benzyl-4-(cyclopropylethynyl)piperidin-4-yl)-2-methylpropane-2-sulfinamide (7-e)

To a −78° C. solution of ethynylcyclopropane (7-d) (0.85 g, 12.8 mmol) in tetrahydrofuran (10 ml) was added n-BuLi (n-butyllitium) (5.13 mL, 12.8 mmol, 2.5 M in hexane). The resulting solution was stirred for 1 h at −78° C. Then a solution of N-(1-benzylpiperidin-4-ylidene)-2-methylpropane-2-sulfinamide (7-c) (1.50 g, 5.13 mmol) and tetraisopropoxytitanium (Ti(O$^i$Pr)$_4$ (0.73 g, 2.56 mmol) in tetrahydrofuran (15 mL) was slowly added via syringe to the reaction mixture. The resulting solution was allowed to warm to RT and was stirred for another 1 h. The reaction was quenched with water (20 mL) and then extracted with dichloromethane (3×20 mL). The combined organic layers were washed with brine (20 mL), dried over anhydrous sodium sulfate and filtered. The filtrate was concentrated under reduced pressure. The residue was purified by flash column chromatography (silica gel) eluting with a gradient of 0% to 30% methanol in dichloromethane to afford N-(1-benzyl-4-(cyclopropylethynyl)piperidin-4-yl)-2-methylpropane-2-sulfinamide (7-e). MS (ESI) Calc'd for (C$_{21}$H$_3$N$_2$OS) [M+H]$^+$, 359; found, 359.

Step 3 1-Benzyl-4-(cyclopropylethynyl)piperidin-4-amine Hydrochloride (7-f)

N-(1-benzyl-4-(cyclopropylethynyl) piperidin-4-yl)-2-methylpropane-2-sulfinamide (7-e) (0.450 g, 1.26 mmol) was added to a solution of hydrogen chloride (HCl) in 1,4-dioxane (1.3 mL, 4M). The reaction solution was stirred for 1 h at RT, then concentrated under reduced pressure to afford 1-benzyl-4-(cyclopropylethynyl) piperidin-4-amine hydrochloride (7-f) which was used in the next step directly without further purification. MS (ESI) Calc'd for (C$_{17}$H$_{23}$N$_2$) [M+H]$^+$, 255; found, 255.

Step 4 (Z)-8-Benzyl-4-(cyclopropylmethylene)-3-oxa-1,8-diazaspiro[4.5]decan-2-one (7-g)

Silver(I) acetate (AgOAc) (131 mg, 0.789 mmol) was added to a solution of 1-benzyl-4-(cyclopropylethynyl) piperidin-4-amine hydrochloride (7-) (0.328 g, 0.789 mmol) in dimethylsulfoxide (DMSO) (2.5 mL). The reaction mixture was placed under an atmosphere of carbon dioxide (2 atm) and stirred for 6 h at RT. The resulting mixture was filtered through Celite™ and the filter cake was washed with methanol (2 mL). The filtrate was concentrated under reduced pressure. The residue was purified by Prep-HPLC [Column: X Bridge C18 OBD Prep Column 100 Å, 10 μm, 19 mm×250 mm; Mobile Phase A: water (10 mmol/L NH$_4$HCO$_3$), Mobile Phase B: ACN; Flow rate: 25 mL/min; Gradient: 35% B to 65% B in 8 min] to afford (Z)-8-benzyl-4-(cyclopropylmethylene)-3-oxa-1,8-diazaspiro[4.5]decan-2-one (7-g) (with longer retention time on HPLC). MS (ESI) Calc'd for (C$_{18}$H$_{23}$N$_2$O$_2$) [M+H]$^+$, 299; found, 299.

Step 5 rac-4-(Cyclopropylmethyl)-3-oxa-1,8-diazaspiro[4.5]decan-2-one (7-h)

Palladium on carbon (Pd/C) (35.7 mg, 0.030 mmol, 10% wt/wt) was added to a solution of (Z)-8-benzyl-4-(cyclopropylmethylene)-3-oxa-1,8-diazaspiro[4.5]decan-2-one (7-g) (100 mg, 0.34 mmol) in methanol (2.5 mL). The reaction mixture was placed under an atmosphere of hydrogen and stirred for 5 h at RT. The resulting mixture was filtered through Celite™ and the filter cake was washed with methanol (2 mL). The filtrate was concentrated under reduced pressure to afford (rac)-4-(cyclopropylmethyl)-3-oxa-1,8-diazaspiro[4.5]decan-2-one (7-h) which used directly in the next step without further purification. MS (ESI) Calc'd for ($C_{11}H_{19}N_2O_2$) [M+H]$^+$, 211; found, 211.

Step 6 5-[4-(cyclopropylmethyl)-2-oxo-3-oxa-1,8-diazaspiro[4.5]dec-8-yl]-3-(1-methyl-1H-pyrazol-4-yl)pyrazine-2-carbonitrile (1-7)

N,N-diisopropylethylamine (i-Pr$_2$NEt) (88 mg, 0.68 mmol) and compound 1-IA (50 mg, 0.23 mmol) were added to a RT solution of 4-(cyclopropylmethyl)-3-oxa-1,8-diazaspiro[4.5]decan-2-one (7-h) (23.9 mg, 0.11 mmol) in 2-propanol (1.5 mL). The resulting solution was stirred for 3 h at 80° C., then cooled to RT and concentrated under reduced pressure. The residue was purified by Prep-HPLC [Column: X Bridge® Prep C18 OBD Column 19×150 mm 5 um (Waters Corporation, Milford, Mass., USA); Mobile Phase A: water (10 mmol/L NH$_4$HCO$_3$), Mobile Phase B: ACN; Flow rate: 20 mL/min; Gradient: 40% B to 50% B in 8 min] to afford racemic 5-(4-(cyclopropylmethyl)-2-oxo-3-oxa-1,8-diazaspiro[4.5]decan-8-yl)-3-(1-methyl-1H-pyrazol-4-yl)pyrazine-2-carbonitrile. The enantiomers were separated using Prep-Chiral HPLC (Column: Chiralpak® IC 2*25 cm, 5um (Chiral Technologies Inc, Daicel Group, West Chester, Pa. USA); Mobile Phase A; Mobile Phase B: MeOH-HPLC; Flow rate: 17 mL/min; Gradient: 100% B isocratic in 26 min) to afford compound 1-7 (slower-eluting enantiomer (retention time=23 min). $^1$H NMR (300 MHz, DMSO-d$_6$): δ 8.36 (s, 2H), 8.20 (s, 1H), 8.05 (s, 1H), 4.60-4.20 (m, 2H), 4.10-4.06 (m, 1H), 3.85 (s, 3H), 1.90-1.52 (m, 5H), 1.21-1.12 (m, 2H), 0.79-0.67 (m, 2H), 0.41-0.26 (m, 2H), 0.07-0.01 (m, 2H). MS (ESI) Calc'd for ($C_{20}H_{24}N_7O_2$) [M+H]$^+$, 394; found, 394.

Example 8

5-(4-ethyl-3-oxo-2,8-diazaspiro[4.5]dec-8-yl)-3-(1-methyl-1H-pyrazol-4-yl)pyrazine-2-carbonitrile (1-8)

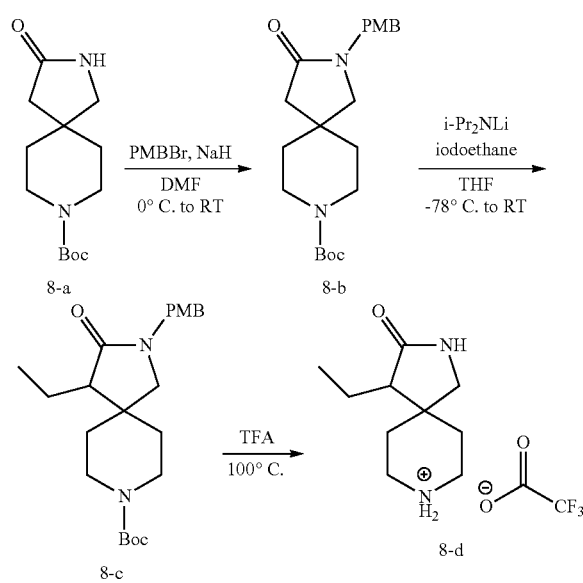

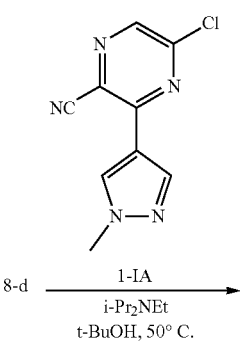

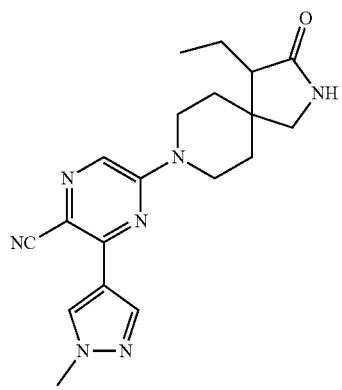

Step 1 tert-Butyl-2-(4-methoxybenzyl)-3-oxo-2,8-diazaspiro[4.5]decane-8-carboxylate (8-b)

Sodium hydride (NaH) (60.5 mg, 1.51 mmol, 60% wt/wt) was added to a 0° C. solution of tert-butyl-3-oxo-2,8-diazaspiro[4.5]decane-8-carboxylate (commercially available from Ark Pharm, Inc., Arlington Heights, Ill., USA) (8-a) (0.350 g, 1.38 mmol) in N,N-dimethylformamide (DMF)(5 mL). The resulting solution was stirred for 0.5 h at 0° C., then 4-methoxybenzyl bromide (PMBBr) (332 mg, 1.65 mmol) was added to the above mixture at 0° C. The resulting mixture was stirred for 2 h at RT. The resulting mixture was quenched with water (20 mL) and the mixture was extracted with ethyl acetate (3×10 mL). The combined organic layers were washed with brine (15 mL), dried over anhydrous sodium sulfate and filtered. The filtrate was concentrated under reduced pressure and the residue was purified by flash column chromatography (silica gel) eluting with a gradient of 30% to 50% ethyl acetate in petroleum ether on a volume basis to afford tert-butyl-2-(4-methoxybenzyl)-3-oxo-2,8-diazaspiro[4.5]decane-8-carboxylate (8-b). MS (ESI) Calc'd for ($C_{21}H_{31}N_2O_4$) [M+H]$^+$, 375; found, 375.

Step 2 tert-Butyl-2-(4-methoxybenzyl)-3-oxo-2,8-diazaspiro[4.5]decane-8-carboxylate (8-c)

n-Butyllithium (0.96 mL, 2.40 mmol, 2.5 M in hexanes) was added to a −78° C. solution of diisopropylamine (0.240 g, 2.40 mmol) in tetrahydrofuran (5 mL). The resulting solution was stirred for 10 min at −78° C., then tert-butyl-2-(4-methoxybenzyl)-3-oxo-2,8-diazaspiro[4.5]decane-8-carboxylate (8-b) (0.600 g, 1.60 mmol) was added to the reaction. The resulting solution was stirred for 15 min at −78° C., afterwhich, iodoethane (0.25 g, 1.60 mmol) was added to the reaction mixture. The resulting solution was allowed to warm to RT and stirred for another 2 h. The reaction was quenched with water (20 mL) and the resulting mixture was extracted with ethyl acetate (3×10 mL). The combined organic layers were washed with brine (15 mL), dried over anhydrous sodium sulfate and filtered. The filtrate was concentrated under reduced pressure. The residue was purified by flash column chromatography (silica gel) eluting with a gradient of 30% to 50% ethyl acetate in petroleum ether to afford tert-butyl-4-ethyl-2-(4-methoxybenzyl)-3-oxo-2,8-diazaspiro[4.5]decane-8-carboxylate (8-c). MS (EST) Calc'd for ($C_{23}H_{35}N_2O_4$) [M+H]$^+$, 403; found, 403.

Step 3 4-Ethyl-2,8-diazaspiro[4.5]decan-3-one 2,2,2-trifluoroacetate (8-d)

A solution of tert-butyl-4-ethyl-2-(4-methoxybenzyl)-3-oxo-2,8-diazaspiro[4.5]decane-8-carboxylate (8-c) (0.20 g, 0.50 mmol) in trifluoroacetic acid (TFA) (3 mL, 40.4 mmol) was stirred for 48 h at 100° C. After cooling to RT, the reaction solution was concentrated under reduced pressure to afford 4-ethyl-2,8-diazaspiro[4.5]decan-3-one 2,2,2-trifluoroacetate (8-d), which was used directly without further purification. MS (ESI) Calc'd for ($C_{10}H_{19}N_2O$) [M+1]$^+$, 183; found, 183.

Step 4 5-(4-ethyl-3-oxo-2,8-diazaspiro[4.5]dec-8-yl)-3-(1-methyl-1H-pyrazol-4-yl)pyrazine-2-carbonitrile (1-8)

The title compound (1-8) was prepared using procedure similar to the described in step 1 in the preparation of compound 1-6, using 4-ethyl-2,8-diazaspiro[4.5] decan-3-one-2,2,2-trifluoroacetate (100 mg, 0.340 mmol). The residue obtained after workup was purified by flash column chromatography (silica gel, using gradient of 50-100% ethyl acetate in petroleum ether as eluent) to afford racemic 5-(4-Ethyl-3-oxo-2,8-diazaspiro[4.5]decan-8-yl)-3-(1-methyl-1H-pyrazol-4-yl)pyrazine-2-carbonitrile. The racemate was separated by Prep-Chiral-HPLC (Column: Chiralpak® IA 2*25 cm, Sum (Chiral Technologies Inc, Daicel Group, West Chester, Pa. USA); Mobile Phase A: MTBE-HPLC, Mobile Phase B: DCM-HPLC; Flow rate: 15 mL/min; Gradient: 10% isocratic) to afford compound 1-8 (slower-eluting enantiomer, retention time=15 min). $^1$H NMR (300 MHz, DMSO-d$_6$): δ 8.44 (s, 1H), 8.28 (s, 1H), 8.13 (s, 1H), 7.56 (s, 1H), 4.31-4.28 (m, 2H), 3.94 (s, 3H), 3.34-3.28 (m, 3H), 3.08-3.04 (m, 1H), 1.90-1.86 (m, 1H), 1.72-1.65 (m, 2H), 1.56-1.38 (m, 4H), 0.98 (t, J=7.2 Hz, 3H). MS (ESI) Calc'd for ($C_{19}H_{24}N_7O$) [M+H]$^+$, 366; found, 366.

Example 9

5-[1-(cyclopropylmethyl)-3-(2-methoxyethyl)-2-oxo-1,3,8-triazaspiro[4.5]dec-8-yl]-3-(1-methyl-1H-pyrazol-4-yl)pyrazine-2-carbonitrile (1-9)

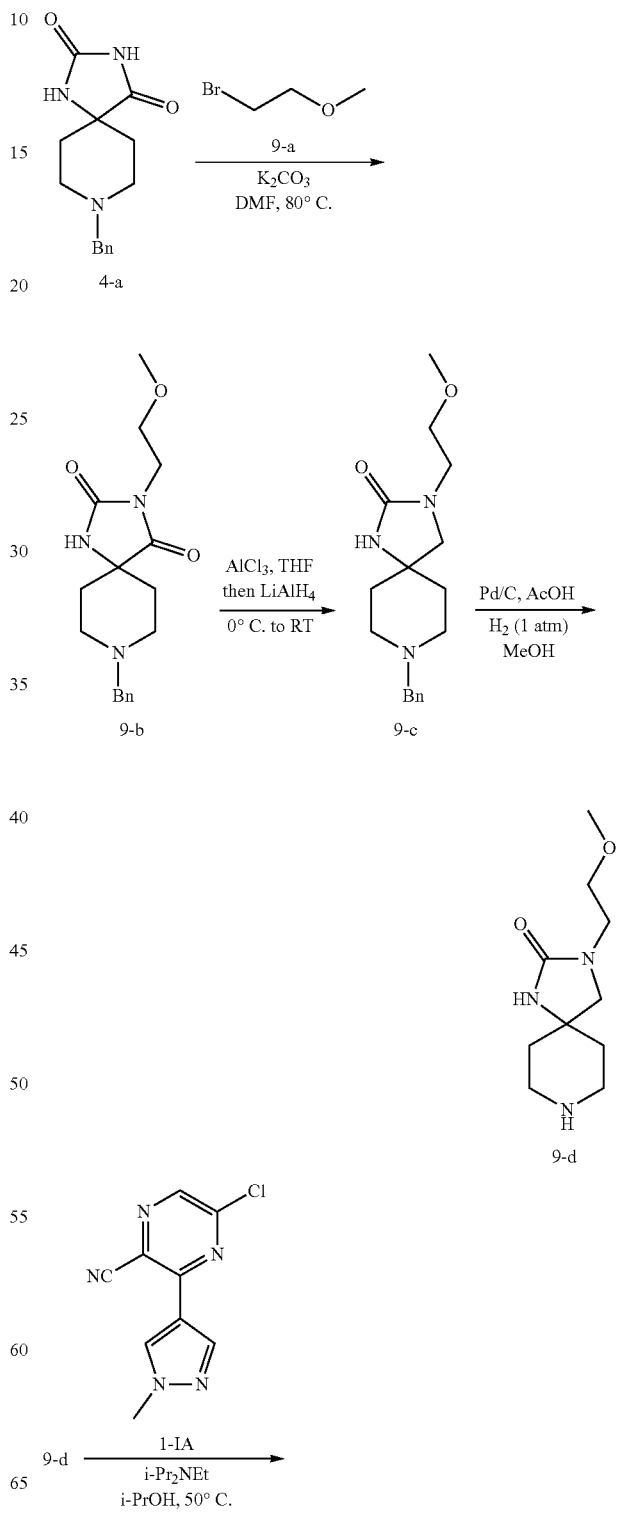

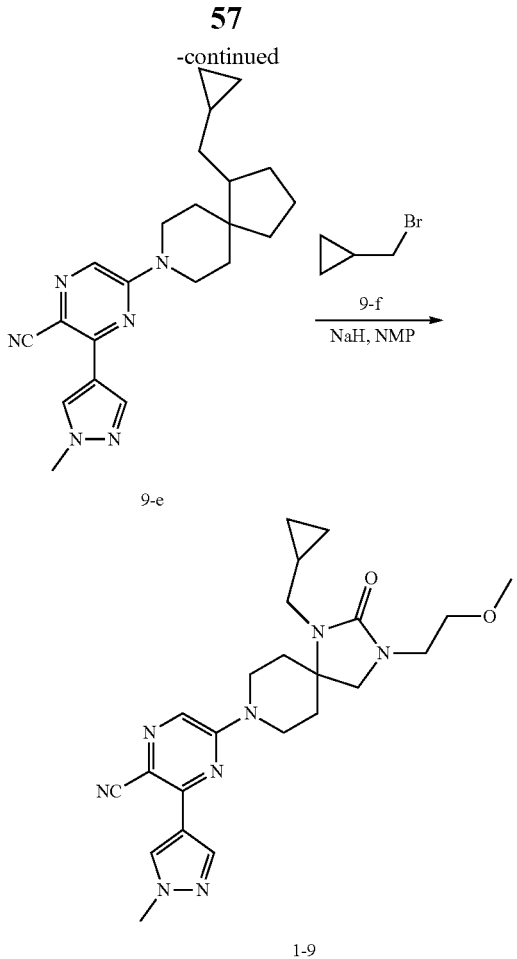

Step 1 8-Benzyl-3-(2-methoxyethyl)-1,3,8-triazaspiro[4.5]decane-2,4-dione (9-b)

Potassium carbonate ($K_2CO_3$) (1.07 g, 7.71 mmol) and 1-bromo-2-methoxyethane (9-a) (0.54 g, 3.86 mmol) were added to a solution of 8-benzyl-1,3,8-triazaspiro[4.5]decane-2,4-dione (4-a) (1.00 g, 3.86 mmol) (prepared according to the same procedure disclosed in *Journal of Medicinal Chemistry* 2002, 45, 3972) in N,N-dimethylformamide (DMF)(15 mL). The resulting mixture was heated to 80° C. for 2 h. After cooling to RT, the reaction mixture was diluted with water (10 mL) then extracted with ethyl acetate (3×20 mL). The combined organic layers were washed with brine (30 mL), dried over anhydrous sodium sulfate and filtered. The filtrate was concentrated under reduced pressure. The residue was purified by flash column chromatography (silica gel) eluting with a gradient of 0% to 10% ethyl acetate in petroleum ether to afford 8-benzyl-3-(2-methoxyethyl)-1,3, 8-triazaspiro[4.5]decane-2,4-dione (9-b). MS (ESI) Calc'd for ($C_{17}H_{24}N_3O_3$) [M+H]$^+$, 318; found, 318.

Step 2 8-Benzyl-3-(2-methoxyethyl)-1,3,8-triazaspiro[4.5]decan-2-one (9-c)

Aluminum trichloride ($AlCl_3$) (0.520 g, 3.91 mmol) was added to a 0° C. solution of 8-benzyl-3-(2-methoxyethyl)-1,3,8-triazaspiro[4.5]decane-2,4-dione (9-b) (0.31 g, 0.98 mmol) in tetrahydrofuran (10 mL). The resulting mixture was stirred for 10 min at ° C., then lithium aluminium hydride ($LiAlH_4$) (111 mg, 2.93 mmol) was added. The resulting mixture was stirred for 18 h at RT, and then quenched with water (2 mL). The mixture was filtered through Celite™ and the filter cake was washed with ethyl acetate (3×20 mL). The filtrate was concentrated under reduced pressure and the residue was purified by flash column chromatography (silica gel) eluting with a gradient of 0% to 10% MeOH in DCM to afford 8-benzyl-3-(2-methoxyethyl)-1,3,8-triazaspiro [4.5]decan-2-one (9-c). MS (ESI) Calc'd for ($C_{17}H_{26}N_3O_2$) [M+H]$^+$, 304; found, 304.

Step 3 3-(2-Methoxyethyl)-1,3,8-triazaspiro[4.5]decan-2-one (9-d)

Acetic acid (AcOH) (4.0 µL, 0.07 mmol) and Pd/C (193 mg, 0.360 mmol, 10% w/w) were added to a solution of 8-benzyl-3-(2-methoxyethyl)-1,3,8-triazaspiro[4.5]decan-2-one (9-c) (0.22 g, 0.73 mmol) in methanol (5 mL). The resulting mixture was placed under an atmosphere of hydrogen (balloon) and stirred for 1 h at RT. The resulting mixture was filtered through Celite™ and the filter cake was washed with methanol (MeOH) (10 mL). The filtrate was concentrated under reduced pressure to afford 3-(2-methoxyethyl)-1,3,8-triazaspiro[4.5]decan-2-one (9-d) which was used directly without further purification. MS (ESI) Calc'd for ($C_{10}H_{20}N_3O_2$) [M+H]$^+$, 214; found, 214.

Step 4 5-(3-(2-Methoxyethyl)-2-oxo-1,3,8-triazaspiro[4.5]decan-8-yl)-3-(1-methyl-1H-pyrazol-4-yl)pyrazine-2-carbonitrile (9-e)

Compound 1-IA (148 mg, 0.680 mmol) and N,N-diisopropylethylamine (0.740 mL, 4.22 mmol) were added to a RT solution of 3-(2-methoxyethyl)-1,3,8-triazaspiro[4.5]decan-2-one (9-d) (180 mg, 0.84 mmol) in 2-propanol (5 mL). The resulting solution was heated to 50° C. for 2 h. After cooling to RT, the reaction mixture was concentrated under reduced pressure and the residue was purified by flash column chromatography (silica gel, eluting with a gradient of 0% to 10% MeOH in DCM) to afford 5-(3-(2-methoxyethyl)-2-oxo-1,3,8-triazaspiro[4.5]decan-8-yl)-3-(1-methyl-1H-pyrazol-4-yl)pyrazine-2-carbonitrile (9-e). MS (ESI) Calc'd for ($C_{19}H_{25}N_8O_2$) [M+H]$^+$, 397; found, 397.

Step 5 5-[1-(cyclopropylmethyl)-3-(2-methoxyethyl)-2-oxo-1,3,8-triazaspiro[4.5]dec-8-yl]-3-(1-methyl-1H-pyrazol-4-yl)pyrazine-2-carbonitrile (1-9)

Sodium hydride (NaH) (7.0 mg, 0.17 mmol, 60% w/w in mineral oil) was added to a 0° C. solution of 5-(3-(2-methoxyethyl)-2-oxo-1,3,8-triazaspiro[4.5]decan-8-yl)-3-(1-methyl-1H-pyrazol-4-yl)pyrazine-2-carbonitrile (9-e) (60 mg, 0.15 mmol) in 1-methyl-2-pyrrolidinone (NMP) (1 mL). The resulting mixture was stirred for 10 min at 0° C., then (bromomethyl)cyclopropane (9-f) (24.5 mg, 0.18 mmol) was added and the mixture was stirred for 2 h at RT. The reaction mixture was quenched with water (1 mL) and the mixture was extracted with ethyl acetate (3×5 mL). The combined organic layers were dried over anhydrous sodium sulfate and filtered. The filtrate was concentrated under reduced pressure and the residue was purified by Prep-HPLC(Column: XBridge™ BEH130 Prep C18 OBD Column 19×150 mm 5 µm 13 nm (Waters Corporation, Milford, Mass., USA); Mobile Phase A: water (10 mmol/L NH$_4$HCO$_3$), Mobile Phase B: ACN; Flow rate: 20 mL/min; Gradient: 30% B to 50% B in 6 min) to afford compound 1-9.

$^1$H NMR (400 MHz, DMSO-d$_6$): δ 8.45 (s, 1H), 8.31 (s, 1H), 8.13 (s, 1H), 4.70-4.60 (m, 2H), 3.93 (s, 3H), 3.45-3.40 (m, 4H), 3.31-3.26 (m, 5H), 3.10-3.06 (m, 2H), 2.85-2.83 (m, 2H), 1.88-1.87 (m, 2H), 1.59-1.55 (m, 2H), 0.91-0.82 (m, 1H), 0.36-0.33 (m, 2H), 0.15-0.13 (m, 2H). MS (ES) Calc'd for (C$_{23}$H$_3$N$_8$O$_2$) [M+H]$^+$, 451.2; found, 451.0.

Example 10

5-[1-(2-methylpropyl)-3-oxo-2-oxa-4,9-diazaspiro [5.5]undec-9-yl]-3-(1-methyl-1H-pyrazol-4-yl)pyrazine-2-carbonitrile (1-10)

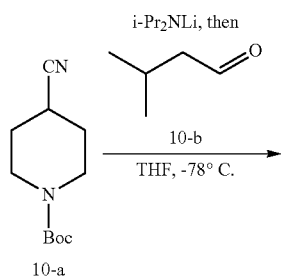

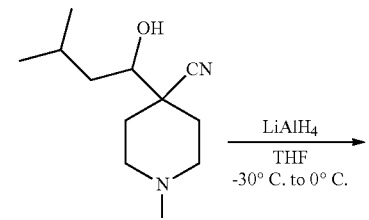

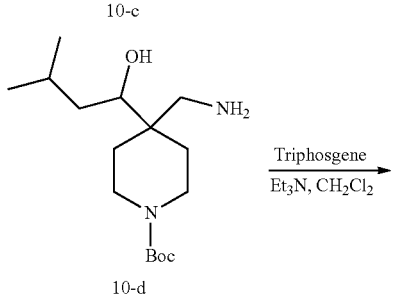

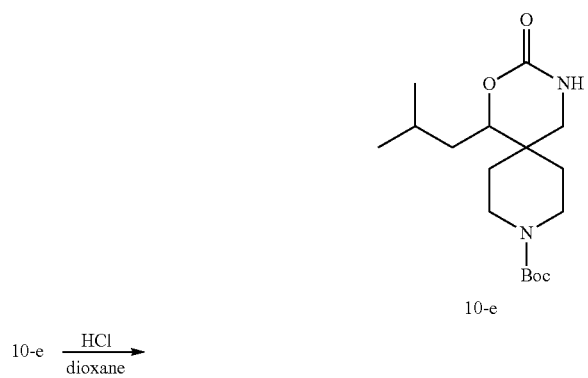

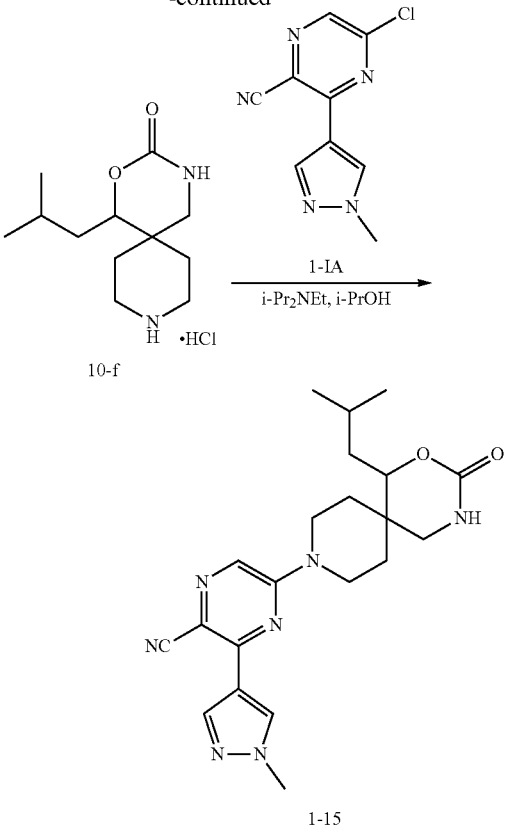

Step 1 tert-Butyl-4-cyano-4-(1-hydroxy-3-methylbutyl)piperidine-1-carboxylate (10-c)

n-Butyllithium (6.28 mL, 15.7 mmol, 2.5M in hexanes) was added dropwise to a −78° C. solution of diisopropylamine (1.59 g, 15.7 mmol) in tetrahydrofuran (100 mL) and the solution was stirred for 1 h at −78° C. Then tert-butyl 4-cyanopiperidine-1-carboxylate (commercially available from, Pharmatech Co., Ltd, P. R. China) (10-a) (3.00 g, 14.3 mmol) was added and after stirring for another 1 h at −78° C., 3-methylbutanal (1.60 g, 18.6 mmol) was added to the reaction mixture. The reaction was stirred for 2 h at −78° C. and then the reaction mixture was quenched with water (100 mL). The mixture was extracted with ethyl acetate (3×100 mL), the combined organic layers was washed with brine (50 mL), dried over anhydrous sodium sulfate and filtered. The filtrate was concentrated under reduced pressure. The residue was purified by flash column chromatography (silica gel, eluting with a gradient of 0% to 20% ethyl acetate in hexane) to afford tert-butyl-4-cyano-4-(1-hydroxy-3-methylbutyl) piperidine-1-carboxylate (10-c). MS (ESI) Calc'd for (C$_{16}$H$_{29}$N$_2$O$_3$) [M+H]$^+$, 297; found, 297.

Step 2 tert-Butyl-4-(aminomethyl)-4-(1-hydroxy-3-methylbutyl)piperidine-1-carboxylate (10-d)

Lithium aluminium hydride (0.510 g, 13.5 mmol) was added portion wise to a −30° C. solution of tert-butyl-4-cyano-4-(1-hydroxy-3-methylbutyl)piperidine-1-carboxylate (10-c) (2.00 g, 6.75 mmol) in tetrahydrofuran (20 mL). The resulting mixture was stirred for 1 h at 0° C., then quenched with sodium sulphate decahydrate (2.00 g) and filtered. The filtrate was concentrated under reduced pressure, and the residue was purified by flash column chromatography (silica gel, eluting with a gradient of 0% to 20% MeOH in DCM) to afford tert-butyl-4-(aminomethyl)-4-(1-hydroxy-3-methylbutyl)piperidine-1-carboxylate (10-d). MS (ESI) Calc'd for ($C_{16}H_{33}N_2O_3$) [M+H]$^+$, 301.2; found, 301.2.

Step 3 tert-Butyl-1-isobutyl-3-oxo-2-oxa-4,9-diazaspiro[5.5]undecane-9-carboxylate (10-e)

Triphosgene (198 mg, 0.670 mmol) and triethylamine (1.16 mL, 8.32 mmol) were added to a 0° C. solution of tert-butyl-4-(aminomethyl)-4-(I-hydroxy-3-methylbutyl)piperidine-1-carboxylate (10-d) (0.50 g, 1.67 mmol) in dichloromethane (5 mL). The reaction mixture was stirred for 1 h at RT, then quenched via the addition of water (10 mL). The resulting mixture was extracted with dichloromethane (3×20 mL) then the combined organic layers were washed with brine (20 mL), dried over anhydrous sodium sulfate and filtered. The filtrate was concentrated under reduced pressure to afford tert-butyl-1-isobutyl-3-oxo-2-oxa-4,9-diazaspiro[5.5]undecane-9-carboxylate (10-e) which was used directly without further purification. MS (ESI) Calc'd for ($C_{17}H_{31}N_2O_4$) [M+H]$^+$, 327; found, 327.

Step 4 1-Isobutyl-2-oxa-4,9-diazaspiro[5.5]undecan-3-one hydrochloride (10-f)

tert-butyl-1-isobutyl-3-oxo-2-oxa-4,9-diazaspiro[5.5]undecane-9-carboxylate (10-e) (0.35 g, 1.07 mmol) was added to a solution of HCl in 1,4-dioxane (10 mL, 4M (molar)). After 4 h. the reaction mixture was concentrated under reduced pressure to afford 1-isobutyl-2-oxa-4,9-diazaspiro[5.5]undecan-3-one hydrochloride (10-), which was used directly without further purification. MS (ESI) Calc'd for ($C_{12}H_{24}N_2O_2$) [M+H]$^+$, 227; found, 227.

Step 5 5-[1-(2-methylpropyl)-3-oxo-2-oxa-4,9-diazaspiro[5.5]undec-9-yl]-3-(1-methyl-1H-pyrazol-4-yl)pyrazine-2-carbonitrile (1-10)

Triethylamine (0.48 mL, 3.41 mmol) and compound 1-IA (150 mg, 0.68 mmol) were added to a solution of 1-isobutyl-2-oxa-4,9-diazaspiro[5.5]undecan-3-one hydrochloride (10-f) (179 mg, 0.680 mmol) in isopropanol (i-PrOH) (5 mL). The resulting solution was stirred for 12 h at RT. The reaction mixture was diluted with water (10 mL) and the mixture was extracted with ethyl acetate (3×10 mL). The combined organic layers were washed with brine (20 mL), dried over anhydrous sodium sulfate and filtered. The filtrate was concentrated under reduced pressure. The residue was purified by flash column chromatography (silica gel, eluting with a gradient of 0% to 10% MeOH in DCM) to afford racemic 5-(1-isobutyl-3-oxo-2-oxa-4,9-diazaspiro[5.5]undecan-9-yl)-3-(1-methyl-1H-pyrazol-4-yl)pyrazine-2-carbonitrile. The racemate was separated by Prep-Chiral HPLC Column: Chiralpak® IA 2*25 cm, 5 μm (Chiral Technologies Inc, Daicel Group. West Chester, Pa. USA); Mobile Phase A: MTBE-HPLC, Mobile Phase B: EtOH-HPLC; Flow rate: 14 mL/min; Gradient: 50% B isocratic) to afford compound, 1-10, (faster-eluting enantiomer, retention time=16 min). $^1$H NMR (300 MHz, DMSO-d$_6$) δ: 8.44 (s, 1H), 8.26 (s, 1H), 8.13 (s, 1H), 7.23 (s, 1H), 4.25-4.10 (m, 2H), 4.10-4.06 (m, 1H), 3.94 (s, 3H), 3.46-3.32 (m, 2H), 3.29-3.26 (m, 2H), 1.75-1.72 (m, 1H), 1.69-1.44 (m, 5H), 1.38-1.33 (m, 1H), 0.95-0.85 (m, 6H). MS (ESI) Calc'd for ($C_{21}H_{28}N_7O_2$) [M+H]$^+$, 410; found, 410.

Example 11

3-(1-methyl-1H-pyrazol-4-yl)-5-[2-oxo-1-(2,2,2-trifluoroethyl)-1,3,8-triazaspiro[4.5]dec-8-yl]pyrazine-2-carbonitrile (1-11)

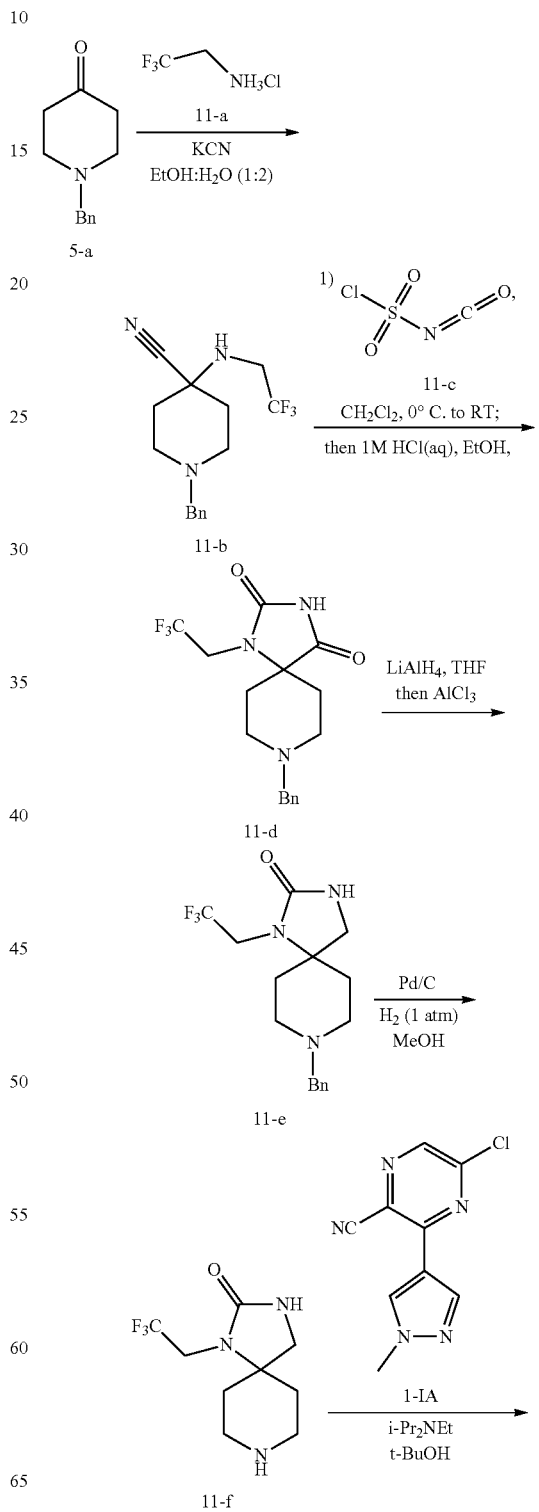

63
-continued

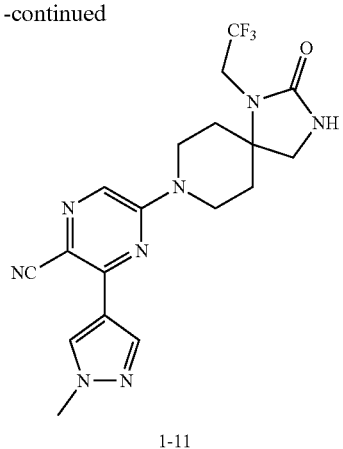

1-11

Step 1 1-Benzyl-4-((2,2,2-trifluoroethyl)amino)piperidine-4-carbonitrile (11-b)

Potassium cyanide (KCN) (6.19 g, 95.0 mmol) and 2,2,2-trifluoroethanamine hydrochloride (commercially available from Sigma Aldrich, St. Louis. Mo., USA) (5-a)(6.30 g, 46.5 mmol) were added to a RT solution of 1-benzylpiperidin-4-one (11-b) (8.00 g, 42.3 mmol) in ethanol/water (20/40 mL). The resulting mixture was stirred for 12 h at 30° C. Water (50 mL) was added and the reaction mixture was extracted with ethyl acetate (3×50 mL). The combined layers were washed with brine (50 mL), dried over anhydrous sodium sulfate and filtered. The filtrate was concentrated under reduced pressure. The residue was purified by flash column chromatography (silica gel, eluting with a gradient of 0% to 15% ethyl acetate in petroleum ether) to afford 1-benzyl-4-((2,2,2-trifluoroethyl)amino)piperidine-4-carbonitrile (11-b). $^1$H NMR (300 MHz, DMSO-$d_6$): δ 7.38-7.21 (m, 5H), 3.71 (t, J=8.1 Hz, 1H), 3.49 (s, 2H), 3.37-3.28 (m, 2H), 2.76-2.70 (m, 2H), 2.24-2.10 (m, 2H), 2.10-1.95 (m, 2H), 1.69-1.53 (m, 2H).

Step 2 8-Benzyl-1-(2,2,2-trifluoroethyl)-1,3,8-triazaspiro[4.5]decane-2,4-dione (11-d)

Chlorosulfonyl isocyanate (commercially available from Matrix Scientific, P O Box 25067, Columbia, S.C., 29224-5067, US) (11-c) (0.520 g, 3.70 mmol) was added to a 0° C. solution of 1-benzyl-4-((2,2,2-trifluoroethyl)amino)piperidine-4-carbonitrile (11-b) (1.00 g, 3.36 mmol) in dichloromethane (10 mL). The resulting solution was stirred for 1 h at RT. Then ethanol (10 mL) and aqueous HCl (1M, 3.36 mL, 3.36 mmol) were added and the resulting mixture was stirred for 14 h at 60° C. Saturated aqueous of sodium carbonate (30 mL) was added to the reaction mixture. The mixture then was extracted with ethyl acetate (3×50 mL). The combined organic layers were washed with brine (50 mL), dried over anhydrous sodium sulfate and filtered. The filtrate was concentrated under reduced pressure. The residue was purified by flash column chromatography (silica gel) eluting with a gradient of 0% to 50% ethyl acetate in petroleum ether to afford 8-benzyl-1-(2,2,2-trifluoroethyl)-1,3,8-triazaspiro[4.5]decane-2,4-dione (11-d). $^1$H NMR (300 MHz, DMSO-$d_6$): δ 11.08 (s, 1H), 7.69-7.63 (m, 2H), 7.49-7.44 (m, 3H), 4.38 (d, J=4.8 Hz, 2H), 4.05-3.96 (m, 2H), 3.50-3.34 (m, 4H), 2.66-2.56 (m, 2H), 2.03-1.99 (m, 2H).

64

Step 3 8-Benzyl-1-(2,2,2-trifluoroethyl)-1,3,8-triazaspiro[4.5]decan-2-one (11-e)

Lithium aluminum hydride (LiALH$_4$) (0.400 g, 10.6 mmol) was added to a 0° C. solution of 8-benzyl-1-(2,2,2-trifluoroethyl)-1,3,8-triazaspiro[4.5]decane-2,4-dione (11-d) (1.20 g, 3.52 mmol) in tetrahydrofuran (30 mL). The resulting mixture was stirred for 0.5 h at 0° C., then aluminum chloride (AlCl$_3$) (1.88 g, 14.1 mmol) was added and the reaction was allowed to stir for another 2 h at RT. The reaction was quenched with water (50 mL) and filtered through Celite™. The filtrate was extracted with ethyl acetate (3×50 mL). The combined organic layers were washed with brine (50 mL), dried over anhydrous sodium sulfate and filtered. The filtrate was concentrated under reduced pressure. The residue was purified by flash column chromatography (silica gel, eluting with a gradient of 50% to 90% ethyl acetate in petroleum ether) to afford 8-benzyl-1-(2,2,2-trifluoroethyl)-1,3,8-triazaspiro[4.5]decan-2-one (11-d). $^1$H NMR (300 MHz, CD$_3$OD): δ 7.36-7.17 (m, 5H), 3.79-3.70 (m, 2H), 3.61-3.48 (m, 2H), 3.31 (s, 2H), 2.93-2.81 (m, 2H), 2.13-2.04 (m, 2H), 1.93-1.83 (m, 2H), 1.65-1.51 (m, 2H).

Step 4 1-(2,2,2-Trifluoroethyl)-1,3,8-triazaspiro[4.5]decan-2-one (11-f)

Palladium on carbon (Pd/C) (0.98 g, 0.92 mmol, 10% wt/wt) was added to a solution of 8-benzyl-1-(2,2,2-trifluoroethyl)-1,3,8-triazaspiro[4.5]decan-2-one (11-e) (0.30 g, 0.92 mmol) in methanol (5 mL). The resulting mixture was placed under an atmosphere of hydrogen and stirred for 2 h at RT. The resulting mixture was filtered through Celite™ and the filter cake was washed with methanol (5 mL). The filtrate was concentrated under reduced pressure to afford 1-(2,2,2-trifluoroethyl)-1,3,8-triazaspiro[4.5]decan-2-one (11-f), which was used directly without further purification. MS (ESI) Calc'd for (C$_9$H$_{15}$F$_3$N$_3$O) [M+H]$^+$, 238; found, 238.

Step 5 3-(1-methyl-1H-pyrazol-4-yl)-5-[2-oxo-1-(2,2,2-trifluoroethyl)-1,3,8-triazaspiro[4.5]dec-8-yl]pyrazine-2-carbonitrile (1-11)

Compound 1-IA (0.20 g, 0.93 mmol) and N,N-diisopropylethylamine (i-PrNEt) (0.540 g, 4.22 mmol) were added to a solution of 1-(2,2,2-trifluoroethyl)-1,3,8-triazaspiro[4.5]decan-2-one (11-f) (0.20 g, 0.84 mmol) in tert-butanol (t-BuOH) (10 mL). The resulting solution was heated to 80° C. for 12 h. After cooling to RT, water (10 mL) was added and the resulting mixture was extracted with ethyl acetate (3×30 mL). The combined organic layers were washed with brine (30 mL), dried over anhydrous sodium sulfate and filtered. The filtrate was concentrated under reduced pressure. The residue was purified by flash column chromatography (silica gel) eluting with a gradient of 50% to 90% ethyl acetate in petroleum ether to afford compound 1-11. $^1$H NMR (300 MHz, DMSO-$d_6$): δ 8.46 (s, 1H), 8.32 (s, 1H), 8.15 (s, 1H), 6.95 (s, 1H), 4.66-4.65 (m, 2H), 3.94 (s, 3H), 3.88-3.78 (m, 2H), 3.39 (s, 2H), 3.12-3.08 (m, 2H), 1.90-1.83 (m, 2H), 1.62-1.58 (m, 2H). MS (ESI) Calc'd for (C$_{18}$H$_{20}$F$_3$N$_8$O) [M+H]$^+$, 421; found, 421.

Example 12

5-[1-(cyclopropylmethyl)-2-oxo-3-oxa-1,8-diazaspiro[4.5]dec-8-yl]-3-[1-(difluoromethyl)-1H-pyrazol-4-yl]pyrazine-2-carbonitrile (1-12)

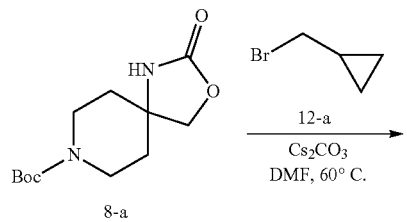

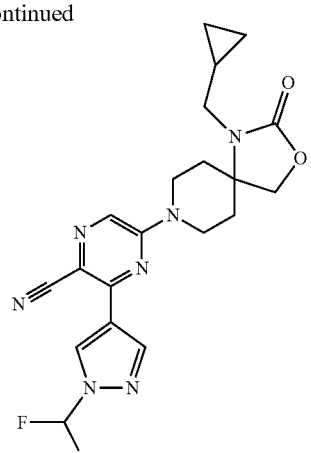

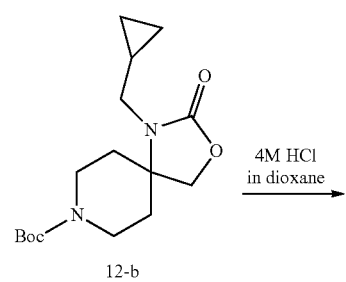

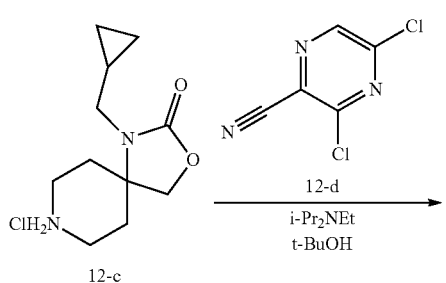

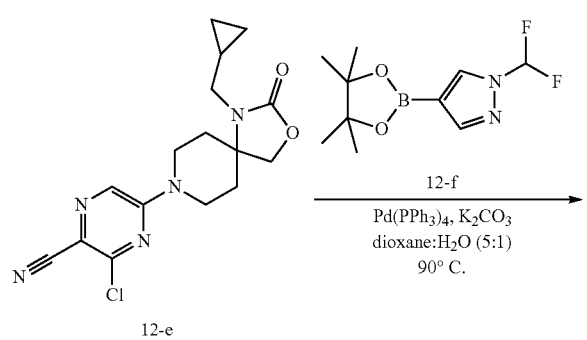

Step 1 tert-Butyl-1-(cyclopropylmethyl)-2-oxo-3-oxa-1,8-diazaspiro[4.5]decane-8-carboxylate (12-b)

To a RT solution of tert-butyl-2-oxo-3-oxa-1,8-diazaspiro[4.5]decane-8-carboxylate (8-a) (0.700 g, 2.73 mmol, (commercially-available from Aurora Building Blocks, Auroro Fine Chemicals, LLC, San Diego, Calif., USA)) in N,N-dimethylformamide (1.5 mL) was added (bromomethyl)cyclopropane (12-a) (0.440 g, 3.28 mmol) and cesium carbonate ($Cs_2CO_3$) (1.78 g, 5.46 mmol). The resulting mixture was stirred for 5 h at 60° C. After cooling to RT, the reaction mixture was quenched with water (5 mL) and the resulting mixture was extracted with ethyl acetate (3×10 mL). The combined organic layers were washed with brine (10 mL), dried over anhydrous sodium sulfate and filtered. The filtrate was concentrated under reduced pressure. The residue was purified by Prep-HPLC [Column: X Bridge® C18 OBD Prep Column, 100 Å, 5 μm, 19 mm×250 mm (Waters Corporation, Milford, Mass., USA); Mobile Phase A: water with 0.03% $NH_4OH$, Mobile Phase B: ACN; Flow rate: 25 mL/min; Gradient: 30% B to 85% B in 8 min] to afford tert-butyl-1-(cyclopropylmethyl)-2-oxo-3-oxa-1,8-diazaspiro[4.5]decane-8-carboxylate (12-b) (0.450 g, 1.40 mmol) as a white solid. MS (ESI) Calc'd for ($C_{16}H_{27}N_2O_4$) $[M+H]^+$, 311.2; found, 311.3.

Step 2 1-(Cyclopropylmethyl)-3-oxa-1,8-diazaspiro[4.5]decan-2-one hydrochloride (12-c)

tert-butyl-1-(cyclopropylmethyl)-2-oxo-3-oxa-1,8-diazaspiro[4.5]decane-8-carboxylate (12-b) (0.450 g, 1.40 mmol) was added to a solution of hydrogen chloride (HCl) in 1,4-dioxane (1.1 mL, 4 M). The reaction solution was stirred for 0.5 h at RT, then concentrated under reduced pressure to afford 1-(cyclopropylmethyl)-3-oxa-1,8-diazaspiro[4.5]decan-2-one hydrochloride (12-c) (0.280 g, 1.14 mmol) and then used directly without further purification. MS (ESI) Calc'd for ($C_{11}H_{19}N_2O_2$) $[M+H]^+$, 211.1; found, 211.1.

Step 3 3-Chloro-5-(1-(cyclopropylmethyl)-2-oxo-3-oxa-1,8-diazaspiro[4.5]decan-8-yl)pyrazine-2-carbonitrile (12-e)

To a RT solution of 1-(cyclopropylmethyl)-3-oxa-1,8-diazaspiro[4.5]decan-2-one hydrochloride (12-c) (0.28 g, 1.14 mmol) in 2-propanol (2.5 mL) was added N,N-diisopropylethylamine (0.73 g, 5.67 mmol) and 3,5-dichloropyrazine-2-carbonitrile (commercially available from Ark Pharm, Inc., Arlington Heights, Ill., USA) (a-1) 197 mg, 1.14 mmol, prepared as in *Org. Lett.* 2013, 2156-2159). The resulting suspension was stirred for 5 h at RT. The mixture was filtered and the solids were dried to afford 3-chloro-5-(1-(cyclopropylmethyl)-2-oxo-3-oxa-1,8-diazaspiro[4.5]decan-8-yl)pyrazine-2-carbonitrile (12-e) (0.30 g, 0.80 mmol) as a solid. MS (ESI) Calc'd for ($C_{16}H_{19}ClN_5O_2$) [M+H]$^+$, 348.1; found, 348.1.

Step 4 5-[1-(cyclopropylmethyl)-2-oxo-3-oxa-1,8-diazaspiro[4.5]dec-8-yl]-3-[1-(difluoromethyl)-1H-pyrazol-4-yl]pyrazine-2-carbonitrile (1-12)

To a solution of 3-chloro-5-(1-(cyclopropylmethyl)-2-oxo-3-oxa-1,8-diazaspiro[4.5]decan-8-yl)pyrazine-2-carbonitrile (12-e) (50 mg, 0.14 mmol) in 1,4-dioxane (2.0 mL)/water (0.4 mL) was added 1-(difluoromethyl)-4-(4,4,5,5-tetramethyl-1,3,2-dioxaborolan-2-yl)-1H-pyrazole (commercially-available from Ark Pharm, Inc., 3860 North Ventura Drive, Arlington Heights, Ill., 60004, US) (12-) (35 mg, 0.14 mmol), Pd(PPh$_3$). (8.31 mg, 7.19 µmol) and potassium carbonate powder (40 mg, 0.29 mmol). The resulting mixture was stirred for 2 h at 90° C. After cooling to RT, the reaction mixture was diluted with water (5 mL). The resulting mixture was extracted with dichloromethane (3×10 mL). The combined organic layers were dried over anhydrous sodium sulfate and filtered. The filtrate was concentrated under reduced pressure. Methanol (0.5 mL) was added to the residue and the resulting solids were collected by filtration, washed with methanol (0.2 mL) and dried to afford 1-12. $^1$H NMR (400 MHz, CDCl$_3$): δ 8.69 (s, 1H), 8.41 (s, 1H), 8.11 (s, 1H), 7.26-7.25 (m, 1H), 4.69-4.66 (m, 2H), 4.30 (s, 2H), 3.07-3.01 (m, 4H), 2.08-2.00 (m, 2H), 1.93-1.89 (m, 2H), 1.03-0.95 (m, 1H), 0.55-0.50 (m, 2H), 0.30-0.25 (m, 2H). MS (ESI) Calc'd for ($C_{20}H_{22}F_2N_7O_2$) [M+H]$^+$, 430; found, 430.

Example 13

3-[(3R)-4-(cyclopropylcarbonyl)-3-methylpiperazin-1-yl]-5-(1-methyl-1H-pyrazol-4-yl)pyrazine-2-carbonitrile (1-13)

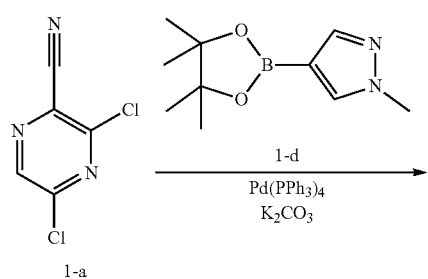

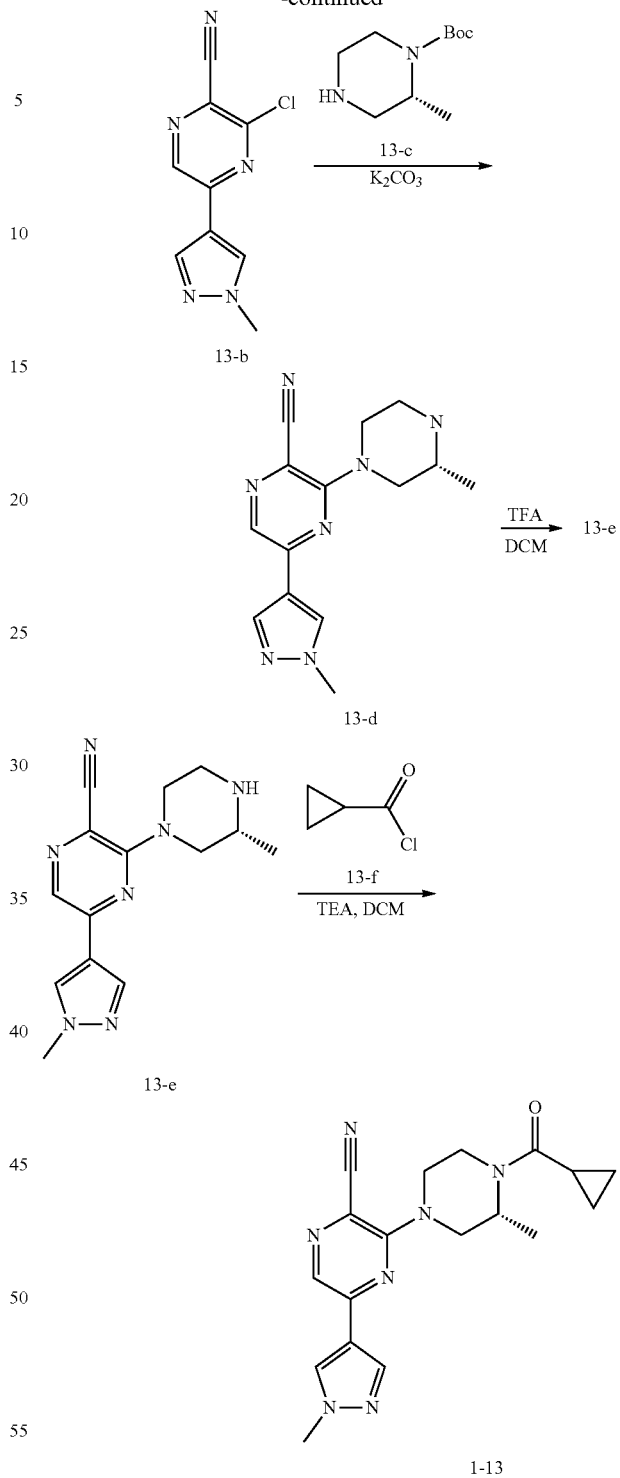

Step 1 3-Chloro-5-(1-methyl-1H-pyrazol-4-yl)pyrazine-2-carbonitrile (13-b)

To a solution of 3,5-dichloropyrazine-2-carbonitrile (1-a) (0.45 g, 2.59 mmol) in 1,4-dioxane/water (8 mL/1.6 mL) were added 1-methyl-4-(4,4,5,5-tetramethyl-1,3,2-dioxaborolan-2-yl)-1H-pyrazole (1-d) (0.65 g, 3.10 mmol), Pd(Ph$_3$P)$_4$ (0.30 g, 0.26 mmol) and potassium carbonate (0.72 g, 5.17 mmol) at RT under nitrogen (1 atm). The resulting mixture was stirred for 2 h at 90° C. after which it was cooled to RT. Water (10 mL) was then added, and the resulting mixture was extracted with ethyl acetate (3×15 mL). The combined organic layers were washed with brine (15 mL), dried over anhydrous sodium sulfate, and filtered. The filtrate was concentrated under reduced pressure and the residue was purified by a column chromatography (silica gel, using gradient of 10%~30% ethyl acetate in pet ether as eluent) to afford 3-chloro-5-(1-methyl-1H-pyrazol-4-yl) pyrazine-2-carbonitrile (13-b). MS (ESI) Calc'd for ($C_9H_7ClN_5$) [M+H]$^+$, 220; found, 220.

Step 2 (R)-tert-Butyl-4-(3-cyano-6-(1-methyl-1H-pyrazol-4-yl)pyrazin-2-yl)-2-methylpiperazine-1-carboxylate (13-d)

To a solution of (R)-tert-butyl-2-methylpiperazine-1-carboxylate (commercially-available from Ark Pharm, Inc., 3860 North Ventura Drive, Arlington Heights, Ill., 60004, US) (13-c) (0.27 g, 1.37 mmol.) in N,N-dimethylformamide (10 mL) were added potassium carbonate (0.38 g, 2.73 mmol) and 3-chloro-5-(1-methyl-1H-pyrazol-4-yl)pyrazine-2-carbonitrile (13-b) (0.30 g, 1.37 mml) at 0° C. The resulting mixture was warmed to RT and was stirred for 16 h. Water (20 mL) was then added to the reaction mixture and the resulting mixture was extracted with ethyl acetate (3×20 mL). The combined organic layers were washed with brine (3×20 mL), dried over anhydrous sodium sulfate, and filtered. The filtrate was concentrated under reduced pressure and the residue was purified by a column chromatography (silica gel, using gradient of 0%~20% ethyl acetate in pet ether as eluent) to afford (R)-tert-butyl-4-(3-cyano-6-(1-methyl-1H-pyrazol-4-yl)pyrazin-2-yl)-2-methylpiperazine-1-carboxylate (13-d). MS (ESI) Calc'd for ($C_{19}H_{26}N_7O_2$) [M+H]$^+$, 384; found, 384.

Step 3 (R)-5-(1-methyl-1H-pyrazol-4-yl)-3-(3-methylpiperazin-1-yl)pyrazine-2-carbonitrile (13-e)

To a solution of (R)-tert-butyl-4-(3-cyano-6-(1-methyl-1H-pyrazol-4-yl)pyrazin-2-yl)-2-methylpiperazine-1-carboxylate (13-d) (0.25 g, 0.65 mmol) in DCM (10 mL) was added TFA (3 mL) at RT. The resulting solution was stirred for 1 h at RT. The reaction solution was then concentrated under reduced pressure, and the residue was diluted with EtOAc (30 mL). The organic layer was washed with saturated aqueous sodium bicarbonate (3×10 mL), dried over anhydrous sodium sulfate, and filtered. The filtrate was concentrated under reduced pressure, and the residue was purified by a column chromatography (silica gel, using gradient of 0%-5% MeOH in DCM as eluent) to afford (R)-5-(1-methyl-1H-pyrazol-4-yl)-3-(3-methylpiperazin-1-yl)pyrazine-2-carbonitrile (13-e). MS (ESI) Calc'd for ($C_{14}H_{18}N_7$) [M+H]$^+$, 284; found, 284.

Step 4 3-[(3R)-4-(cyclopropylcarbonyl)-3-methylpiperazin-1-yl]-5-(I-methyl-1H-pyrazol-4-yl)pyrazine-2-carbonitrile (1-13)

To a mixture of compound 13-e (100 mg, 0.35 mmol) and TEA (0.1 mL, 0.71 mmol) in DCM (5 mL) was added dropwise, cyclopropanecarbonyl chloride (13-) (36.9 mg, 0.35 mmol) at RT. The resulting mixture was stirred for 1 h. The reaction mixture was then quenched with water (10 mL), and the resulting solution was extracted with DCM (2×10 mL). The combined organic layers were washed with brine (10 mL), dried over anhydrous sodium sulfate, and filtered. The filtrate was concentrated under reduced pressure, and the residue was purified by Preparatory HPLC (Column, XBridge™ Prep Shield RP18, 5 μm, 19×150 mm (Waters Corporation, Milford, Mass., USA); Mobile phase A: water (10 mmol/L NH$_4$HCO$_3$), Mobile phase B: ACN; Flow rate: 20 mL/min; Gradient: 30% B to 50%) to afford compound 1-13. $^1$H NMR (400 MHz, CD$_3$OD) δ 8.37 (m, 2H), 8.15 (s, 1H), 4.81-4.75 (m, 1H), 4.51-4.32 (m, 3H), 3.99 (s, 3H), 3.75-3.32 (m, 3H), 2.05-1.97 (m, 11H), 1.45-1.30 (m, 3H), 0.98-0.88 (m, 4H). MS (ESI) Calc'd for ($C_{18}H_{22}N_7O$) [M+H]$^+$, 352, found, 352.

Example 14

5-[(3R)-3-methyl-4-{[(1R,2R)-2-methylcyclopropyl]carbonyl}piperazin-1-yl]-3-(1-methyl-1H-pyrazol-4-yl)pyrazine-2-carbonitrile (1-14)

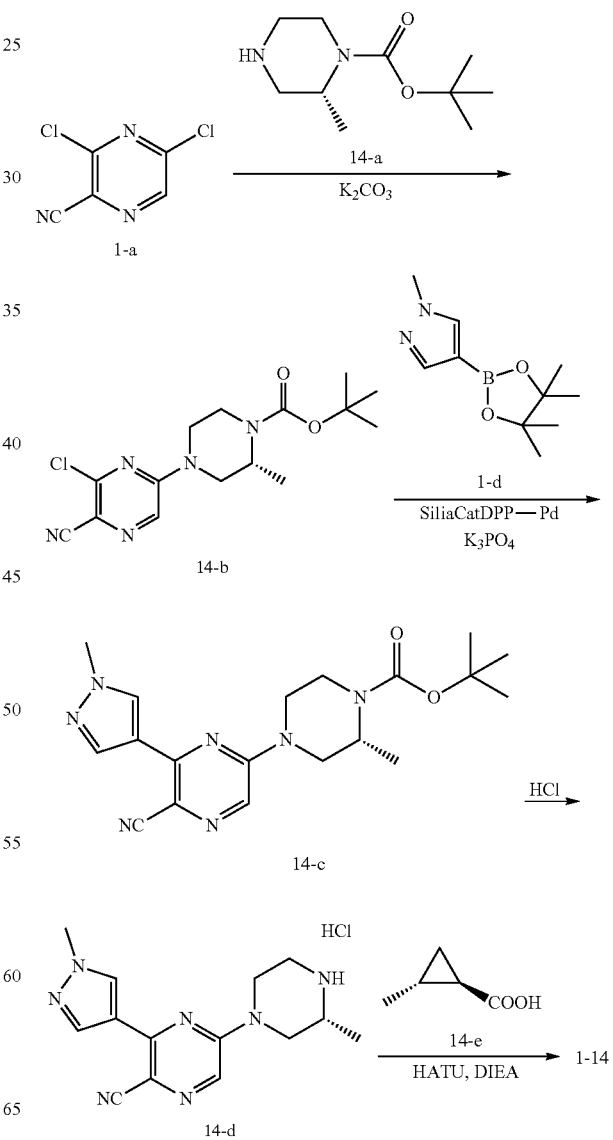

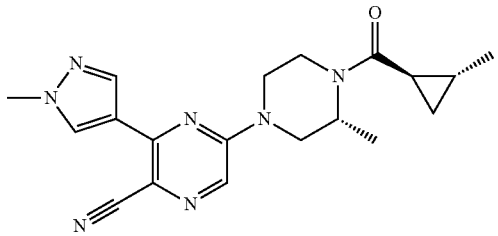

1-14

Step 1 (R)-tert-butyl-4-(6-chloro-5-cyanopyrazin-2-yl)-2-methylpiperazin-1-carboxylate (14-b)

3,5-dichloropyrazine-2-carbonitrile (1-a) (500 mg, 2.9 mmol, prepared as in *Org. Let.* 2013, 2156-2159), (R)-tert-butyl 2-methylpiperazine-1-carboxylate (commercially-available from Ark Pharm, Inc., 3860 North Ventura Drive, Arlington Heights. Ill., 60004, US) (14-a) (460 mg, 2.3 mmol), and $K_2CO_3$ (794 mg, 5.75 mmol) were combined in a 40 mL pressure vial. DMF (28 mL) was added and the reaction mixture was allowed to stir at rt overnight. The reaction mixture was then diluted with 3:1 chloroform/IPA (isopropyl alcohol) and washed with saturated, aqueous $NH_4Cl$. The combined organic layers were washed with brine, dried over magnesium sulfate ($MgSO_4$), and concentrated in vacuo while loading onto silica gel. The residue was purified by column chromatography (silica gel, eluting with a gradient of 0-50% 3:1 EtOAc/EtOH in hexanes to afford (R)-tert-butyl 4-(6-chloro-5-cyanopyrazin-2-yl)-2-methylpiperazine-1-carboxylate (14-b). MS (ESI) Calc'd for ($C_{15}H_{21}ClN_5O_2$) $[M+H]^+$, 338; found, 338.

Step 2 (R)-tert-butyl-4-(5-cyano-6-(1-methyl-1H-pyrazol-4-yl)pyrazin-2-yl)-2-methylpiperazine-1-carboxylate (14-c)

To a stirred solution of (R)-tert-butyl 4-(6-chloro-5-cyanopyrazin-2-yl)-2-methylpiperazine-1-carboxylate (14-b) (180 mg, 0.53 mmol) in 1,4-dioxane (3 mL) were added SiliaCat® DPP-Pd (diphenylphosphine palladium (II) heterogeneous catalyst)(410 mg, 0.11 mmol) (available from Silicycle, Quebec City, Quebec, Canada), $K_3PO_4$ (339 mg, 1.560 mmol) and 1-methyl-4-(4,4,5,5-tetramethyl-1,3,2-dioxaborolan-2-yl)-1H-pyrazole (1-d) (133 mg, 0.639 mmol). The solution mixture was stirred for 4 h at 90° C. under the nitrogen atmosphere. The solution was then cooled to RT and the solution was diluted with water (5 mL) and DCM. The mixture was then poured into a phase separator and the DCM layer was collected. The material was concentrated in vacuo, and the residue was purified by column chromatography (silica gel, eluting with a gradient of 0-100% 3:1 EtOAc/EtOH in hexanes to afford (R)-tert-butyl-4-(5-cyano-6-(1-methyl-1H-pyrazol-4-yl)pyrazin-2-yl)-2-methylpiperazine-1-carboxylate (14-c). MS (ESI) Calc'd for ($C_{19}H_{26}N_7O_2$) $[M+H]^+$, 338; found, 338.

Step 3 (R)-3-(1-methyl-1H-pyrazol-4-yl)-5-(3-methylpiperazin-1-yl)pyrazine-2-carbonitrile hydrochloride (14-d)

Tert-butyl (R)-4-(5-cyano-6-(1-methyl-1H-pyrazol-4-yl)pyrazin-2-yl)-2-methylpiperazine-1-carboxylate (14-c) (8 g, 20.86 mmol) was treated with 4 M HCl in dioxane (20.8 mL, 83 mmol), and the reaction was stirred for 5 h at RT. The solvent was then removed in vacuo to afford (R)-3-(1-methyl-1H-pyrazol-4-yl)-5-(3-methylpiperazin-1-yl)pyrazine-2-carbonitrile hydrochloride (14-d), which was used I the next step without further purification. MS (ESI) Calc'd for ($C_{14}H_{18}N_8$) $[M+H]^+$, 284; found, 284.

Step 4 5-[(3R)-3-methyl-4-{[(1R,2R)-2-methylcyclopropyl]carbonyl}piperazin-1-yl]-3-(1-methyl-1H-pyrazol-4-yl)pyrazine-2-carbonitrile (1-14)

To a mixture of (R)-3-(1-methyl-1H-pyrazol-4-yl)-5-(3-methylpiperazin-1-yl)pyrazine-2-carbonitrile hydrochloride (14-d) (6.7 g, 21 mmol), (1R,2R)-2-methylcyclopropane-1-carboxylic acid (14-e) (3.36 g, 33.5 mmol), and HATU (14.3 g, 37.7 mmol) in DMF (70 mL) was added DIEA (14.6 mL, 84 mmol). The reaction was stirred for 1 h at RT, after water (800 mL) was added with vigorous stirring. The mixture was stirred for 2 h, after which the mixture was filtered and the solid was further washed with water (200 mL). The resulting cake was dried under vacuum (nitrogen flow) to afford compound, 1-14. MS (ESI) Calc'd for ($C_{19}H_{24}N_7O$) $[M+H]^+$, 366; found, 366. 1H NMR (600 MHz, DMSO-$d_6$): δ ppm 8.43 (s, 1H), 8.25 (s, 1H), 8.12 (s, 1H), 4.56 (br. s, 1H), 4.34 (br. s, 2H), 4.12 (br. s, 1H), 3.91 (s, 3H), 3.51-3.09 (br. m, 3H), 1.69 (s, 1H), 1.21-0.89 (br. m, 8H), 0.53 (s, 1H).

Example 15

5-[(3R)-4-(cyclopropylcarbonyl)-3-methylpiperazin-1-yl]-3-(1-methyl-1H-pyrazol-4-yl)pyrazine-2-carbonitrile (1-15)

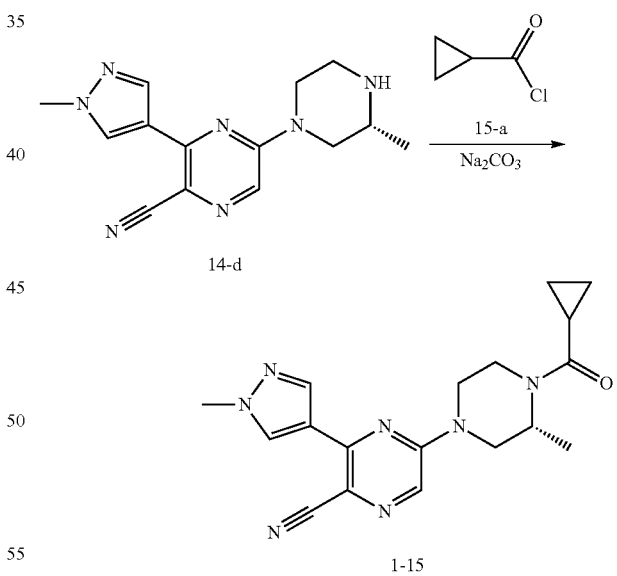

To a solution of the free-base of compound 14-d (41 mg, 0.15 mmol) in DCM (5 mL) and saturated aqueous of sodium bicarbonate ($Na_2CO_3$) (10 mL) was added cyclopropanecarbonyl chloride (15-a) (18.2 mg, 0.17 mmol) at 0° C. The solution was then allowed to stir at RT for 3 h, after which the solution was extracted with dichloromethane (3×5 mL). The combined organic layers was washed with brine (10 mL), dried over anhydrous sodium sulfate, and filtered. The filtrate was concentrated under reduced pressure, and the residue was purified by a column chromatography (silica gel, using a gradient of 50%~100% EtOAc in pet ether as eluent) to afford the crude product. The crude product was further purified by preparatory HPLC (Column: Xbridge™ RP18, 5 um, 19×150 mm (Waters Corporation. Milford, Mass., USA); mobile phase: water (0.05% ammonium bicarbonate+carbon dioxide) and acetonitrile (10% acetonitrile up to 62% in 5 min, hold 95% for 2 min, down to 10% in 2 min)) to afford compound, 1-15. $^1$H-NMR (300 MHz, DMSO-d$_6$): δ: 8.47 (s, 1H), 8.29 (s, 1H), 8.16 (s, 1H), 4.64-4.61 (m, 1H), 4.40-4.37 (m, 2H), 4.21-4.17 (m, 1H), 3.95 (s, 3H), 3.64-3.10 (m, 3H), 2.02-1.97 (m, 1H), 1.20-1.09 (m, 3H), 0.76-0.73 (m, 4H). MS (ESI) Calc'd for (CigH$_{22}$NO) [M+H]$^+$, 352; found, 352.

Example 16

(2R)-4-[5-cyano-6-(1-methyl-1H-pyrazol-4-yl)pyrazin-2-yl]-N-(cyclopropylmethyl)-2-methylpiperazine-1-carboxamide (1-16)

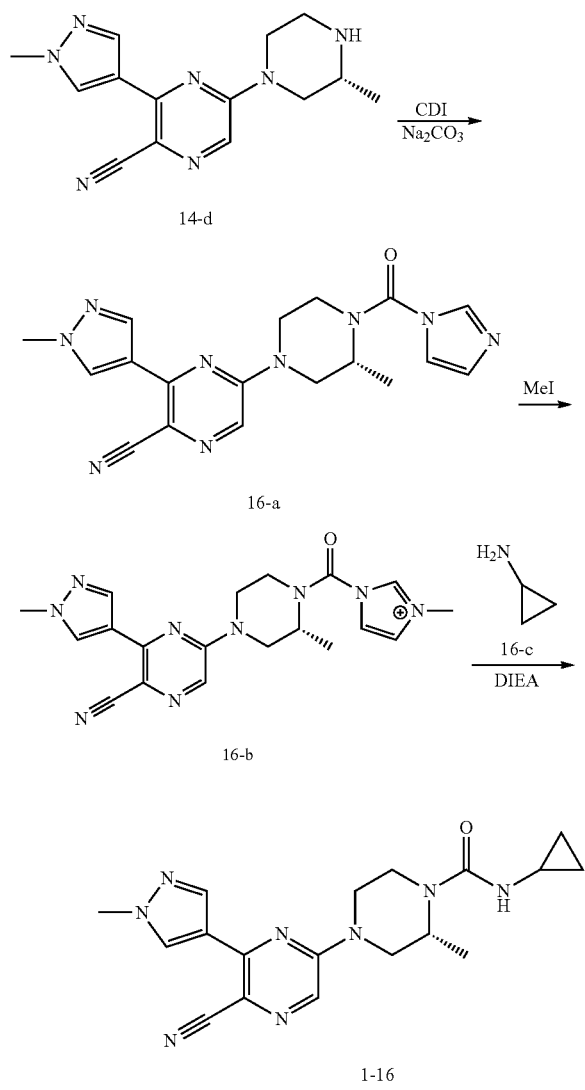

Step 1 (R)-5-(4-(1H-imidazole-1-carbonyl)-3-methylpiperazin-1-yl)-3-(1-methyl-1H-pyrazol-4-yl)pyrazine-2-carbonitrile (16-a)

(R)-3-(1-methyl-1H-pyrazol-4-yl)-5-(3-methylpiperazin-1-yl)pyrazine-2-carbonitrile (14-d) (780 mg, 2.8 mmol) and carbonyldiimidazole (CDI) (893 mg, 5.51 mmol) were taken up in THF (14 ml) under a nitrogen atmosphere and DIPEA (1.44 ml, 8.26 mmol) was added. The reaction was then heated to 75° C. and was allowed to stir for 2 hours, after which the reaction was cooled to rt and a solution of 3:1 chloroform:IPA (on a volume basis) and saturated aqueous ammonium chloride (NH$_4$Cl) were added. The mixture was extracted with 3:1 chloroform:IPA (on a volume basis), and the combined organic layers were washed with brine, dried over MgSO4, and concentrated in vacuo while loading onto silica gel. The residue was then purified via column chromatography (ISCO Gold Silica 24 g column (Teledyne ISCO, Inc., Lincoln, Nebr., USA), eluting with a gradient of 30-100% 3:1 EtOAc:EtOH (v/v) in Hexanes) to provide (R)-5-(4-(1H-imidazole-1-carbonyl)-3-methylpiperazin-1-yl)-3-(1-methyl-1H-pyrazol-4-yl)pyrazine-2-carbonitrile (16-a). MS (ESI) Calc'd for (C$_{18}$H$_{20}$N$_9$O) [M+H]$^+$, 378; found, 378.

Step 2 (R)-1-(4-(5-cyano-6-(1-methyl-1H-pyrazol-4-yl)pyrazin-2-yl)-2-methylpiperazine-1-carbonyl)-3-methyl-1H-imidazol-3-ium (16-b)

A 20 ml high pressure vial was charged with (R)-5-(4-(1H-imidazole-1-carbonyl)-3-methylpiperazin-1-yl)-3-(1-methyl-1H-pyrazol-4-yl)pyrazine-2-carbonitrile (16-a) (712 mg, 1.89 mmol) and acetonitrile (15 ml) was added, followed by methyl iodide (MeI) (0.47 ml, 7.6 mmol). The reaction mixture was allowed to stir overnight at rt, after which the solvent was removed in vacuo and the residue was triturated in ether. The resulting solid was collected by vacuum filtration to provide (R)-1-(4-(5-cyano-6-(1-methyl-1H-pyrazol-4-yl)pyrazin-2-yl)-2-methylpiperazine-1-carbonyl)-3-methyl-1H-imidazol-3-ium (16-b). MS (ESI) Calc'd for (C$_{19}$H$_{22}$N$_9$O$^+$) [M]$^+$, 392; found, 392.

Step 3 (R)-4-(5-cyano-6-(1-methyl-1H-pyrazol-4-yl)pyrazin-2-yl)-N-cyclopropyl-2-methylpiperazine-1-carboxamide (1-16)

(R)-1-(4-(5-cyano-6-(1-methyl-1H-pyrazol-4-yl)pyrazin-2-yl)-2-methylpiperazine-1-carbonyl)-3-methyl-1H-imidazol-3-ium (16-b) (30 mg, 0.076 mmol) and cyclopropanamine (16-d) (5.30 μl, 0.076 mmol) were dissolved in dimethylacetamide (DMA) (764 μl) and DIEA (26.7 μl, 0.153 mmol) was added. The resulting solution was allowed to stir at 55° C. overnight. The reaction was then taken up in DMSO and was purified via mass-triggered reversed phase HPLC (5:95 to 95:5 acetonitrile:water: 0.1% v/v TFA modifier) to give (R)-4-(5-cyano-6-(1-methyl-1H-pyrazol-4-yl)pyrazin-2-yl)-N-cyclopropyl-2-methylpiperazine-1-carboxamide as the TFA salt (1-16). $^1$H NMR (499 MHz, DMSO-d6) δ 8.46 (s, 1H), 8.29 (s, 1H), 8.15 (s, 1H), 6.65 (s, 1H), 4.51-4.18 (m, 3H), 3.94 (s, 3H), 3.81-3.75 (m, 1H), 3.60-3.37 (m, 1H), 3.33-3.25 (m, 1H), 3.14-2.99 (m, 2H), 1.01 (d, J=6.6 Hz, 3H), 0.57-0.50 (m, 2H), 0.41-0.35 (m, 2H). MS (ESI) Calc'd for (C$_{18}$H$_{23}$N$_8$O) [M+H]$^+$, 367; found, 367.

Example 17

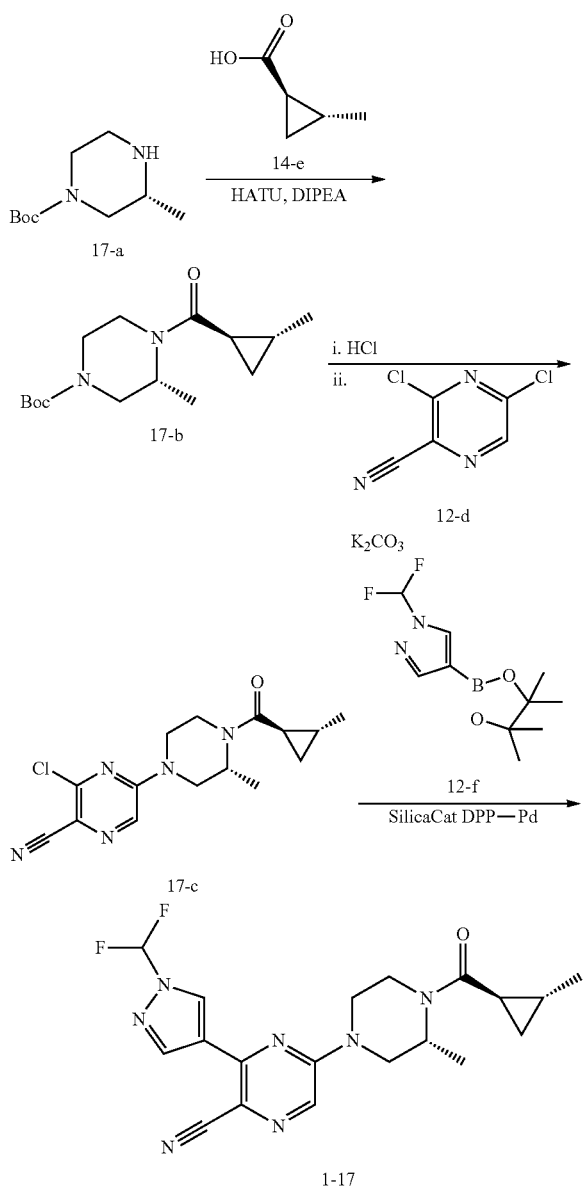

Step 1 (R)-tert-butyl-3-methyl-4-((1R,2R)-2-methyl-cyclopropanecarbonyl)piperazine-1-carboxylate (17-b)

(R)-tert-butyl 3-methylpiperazine-1-carboxylate (17-a) (0.5 g, 2.5 mmol), (1R,2R)-2-methylcyclopropanecarboxylic acid (14-e) (0.3 g, 3.0 mmol), and HATU (1.42 g, 3.74 mmol) were taken up in DMF (12.5 ml). DIPEA (1.74 ml, 10.0 mmol) was then added and the reaction mixture was allowed to stir at RT overnight. A mixture of 3:1 chloroform/IPA (on a volume basis) and saturated NaHCO₃ (aqueous) were added. The products were then exacted into the organic layer (×3). The combined organics were then washed with saturated NH₄Cl (aqueous), washed with brine, dried over MgSO₄, and concentrated in vacuo while loading onto silica gel. The residue was then purified by column chromatography (silica gel, eluting with a gradient of 0-50% 3:1 EtOAc/EtOH in Hexanes to afford (R)-tert-butyl 3-methyl-4-((1R,2R)-2-methylcyclopropanecarbonyl)piperazine-1-carboxylate (17-b). MS (ESI) Calc'd for (C$_{11}$H$_{19}$N$_2$O$_3$)[M+H-tBu]$^+$, 277; found, 277.

Step 2 3-chloro-5-((R)-3-methyl-4-((1R,2R)-2-methylcyclopropanecarbonyl)piperain-1-yl)pyrazine-2-carbonitrile (17-c)

(R)-tert-butyl 3-methyl-4-((1R,2R)-2-methylcyclopropanecarbonyl)piperazine-1-carboxylate (17-b) (350 mg, 1.24 mmol) was taken up in 1,4-dioxane (3 ml) and MeOH (3 ml) after which HCl in dioxane (4.0 M, 0.62 ml, 2.48 mmol) was added. The reaction was allowed to stir at RT for 2 hours. The mixture was concentrated in vacuo to give (((1R,2R)-2-methylcyclopropyl)((R)-2-methylpiperazin-1-yl)methanone hydrochloride which was used in the next step without further purification to produce compound (17-c).

3,5-dichloropyrazine-2-carbonitrile (12-d) (200 mg, 1.15 mmol), ((1R,2R)-2-methylcyclopropyl)((R)-2-methylpiperazin-1-yl)methanone hydrochloride (230 mg, 1.06 mmol) and K$_2$CO$_3$ (318 mg, 2.30 mmol) were taken up in DMF (5 ml). The reaction mixture was allowed to stir at rt overnight. The reaction mixture was then poured into a solution of 3:1 chloroform/IPA and washed with saturated NH$_4$Cl (aqueous). The combined organic layers were washed with brine, dried over MgSO$_4$, and concentrated in vacuo. The residue was purified by flash chromatography (silica gel, eluting with a gradient of 0-50% 3:1 EtoAc:EtOH (v/v) in Hexanes to provide 3-chloro-5-((R)-3-methyl-4-((1R,2R)-2-methylcyclopropanecarbonyl) piperazin-1-yl)pyrazine-2-carbonitrile. (17-c). MS (ESI) Calc'd for (C$_{15}$H$_{19}$ClN$_5$O) [M+H]$^+$, 320; found, 320.

Step 3 3-[1-(difluoromethyl)-1H-pyrazol-4-yl]-5-[(3R)-3-methyl-4-{[(1R,2R)-2-methylcyclopropyl]carbonyl}piperazin-1-yl]pyrazine-2-carbonitrile (1-17)

To a stirred solution of 1-(difluoromethyl)-4-(4,4,5,5-tetramethyl-1,3,2-dioxaborolan-2-yl)-1H-pyrazole (12-f) (63.0 mg, 0.26 mmol) in 1,4-dioxane (0.8 ml) and Water (0.8 ml), were added SilicaCat® DPP-Pd (SiliCycle, Inc., Quebec City, Canada) (180 mg, 0.047 mmol), potassium phosphate tribasic (149 mg, 0.704 mmol) and 3-chloro-5-((R)-3-methyl-4-((1R,2R)-2-methylcyclopropanecarbonyl) piperazin-1-yl)pyrazine-2-carbonitrile (17-c) (75 mg, 0.24 mmol). The solution mixture was stirred for 30 min at 90° C. under microwave irradiation. The solution was then cooled to RT and was diluted with water (5 mL) and DCM (5 mL) and the mixture was partitioned with an Isolute® SPE phase separator cartridge (Biotage™, Charlotte, N.C., USA). The mixture was then concentrated in vacuo and the residue was purified via mass-triggered reversed phase HPLC (5:95 to 95:5 acetonitrile:water: 0.1% v/v TFA modifier). The product-containing fractions were taken up in 3:1 chloroform/IPA and washed with saturated NaHCO$_3$ (aqueous). The combined organic layers were washed with brine, dried over MgSO$_4$, and concentrated in vacuo to give 3-(1-(difluoromethyl)-1H-pyrazol-4-yl)-5-((R)-3-methyl-4-((1R,2R)-2-methylcyclopropanecarbonyl)piperazin-1-yl) pyrazine-2-carbonitrile (1-17). $^1$H NMR (499 MHz, DMSO-d$_6$) δ 8.95 (s, 1H), 8.47 (s, 1H), 8.38 (s, 1H), 7.97 (t, J=58.6 Hz, 1H), 4.60 (s, 1H), 4.52-4.23 (m, 1H), 4.16 (br d, J=12.3 Hz, 1H), 3.81-3.03 (m, 4H), 1.79-1.61 (m, 1H), 1.22 (s, 2H), 1.09 (app s, 3H), 1.03 (d, J=6.1 Hz, 3H), 0.61-0.51 (m, 1H). MS (ESI) Calc'd for ($C_{19}H_{22}F_2N_7O$) [M+H]$^+$, 402; found, 402.

Example 18

(R)-5-(4-(cyclopropanecarbonyl)-3-methylpiperazin-1-yl)-3-(1-(methyl-d3)-1H-pyrazol-4-yl)pyrazine-2-carbonitrile (1-18)

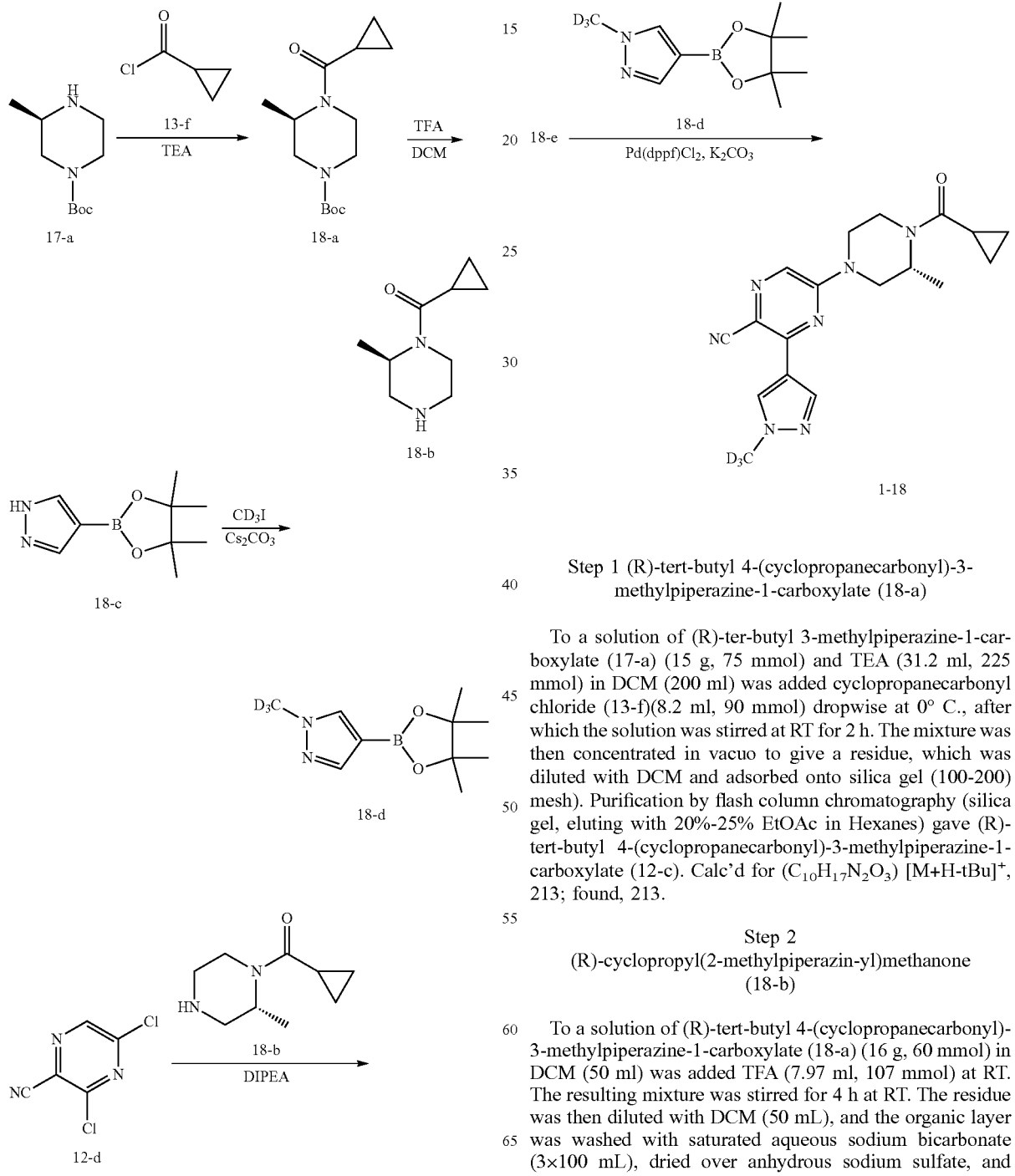

Step 1 (R)-tert-butyl 4-(cyclopropanecarbonyl)-3-methylpiperazine-1-carboxylate (18-a)

To a solution of (R)-ter-butyl 3-methylpiperazine-1-carboxylate (17-a) (15 g, 75 mmol) and TEA (31.2 ml, 225 mmol) in DCM (200 ml) was added cyclopropanecarbonyl chloride (13-f)(8.2 ml, 90 mmol) dropwise at 0° C., after which the solution was stirred at RT for 2 h. The mixture was then concentrated in vacuo to give a residue, which was diluted with DCM and adsorbed onto silica gel (100-200) mesh). Purification by flash column chromatography (silica gel, eluting with 20%-25% EtOAc in Hexanes) gave (R)-tert-butyl 4-(cyclopropanecarbonyl)-3-methylpiperazine-1-carboxylate (12-c). Calc'd for ($C_{10}H_{17}N_2O_3$) [M+H-tBu]$^+$, 213; found, 213.

Step 2 (R)-cyclopropyl(2-methylpiperazin-yl)methanone (18-b)

To a solution of (R)-tert-butyl 4-(cyclopropanecarbonyl)-3-methylpiperazine-1-carboxylate (18-a) (16 g, 60 mmol) in DCM (50 ml) was added TFA (7.97 ml, 107 mmol) at RT. The resulting mixture was stirred for 4 h at RT. The residue was then diluted with DCM (50 mL), and the organic layer was washed with saturated aqueous sodium bicarbonate (3×100 mL), dried over anhydrous sodium sulfate, and filtered. The filtrate was concentrated under reduced pressure, and the residue was purified by column chromatography (silica gel, using a gradient of 85 to 95% EtOAc in Hexanes as eluent) to afford (R)-cyclopropyl(2-methylpiperazin-1-yl)methanone (18-b). Calc'd for ($C_9H_{17}N_2O$) [M+H]+, 169; found, 169.

Step 3 1-(methyl-d3)-4-(4,4,5,5-tetramethyl-1,3,2-dioxaborolan-2-yl)-1H-pyrazole (18-d)

To a solution of 4-(4,4,5,5-tetramethyl-1,3,2-dioxaborolan-2-yl)-1H-pyrazole (18-c) (0.20 g, 1.03 mmol) in DMF (10 mL) were added cesium carbonate (0.50 g, 1.55 mmol) and trideuteriomethyl iodide (0.22 g, 1.55 mmol) at RT. The resulting mixture was stirred for 2 h at RT, after which the reaction was diluted with water (50 mL), extracted with EtOAc (3×30 mL). The combined organic layers were washed with brine (4×20 mL), dried over anhydrous sodium sulfate, and filtered. The filtrate was concentrated under reduced pressure to afford 1-(methyl-d3)-4-(4,4,5,5-tetramethyl-1,3,2-dioxaborolan-2-yl)-1H-pyrazole (18-d), which was used in the next step without further purification. MS (ESI) Calc'd for ($C_{10}H_{15}D_3BN_2O_2$) [M+H]+, 212; found, 212.

Step 4 (R)-3-chloro-5-(4-(cyclopropanecarbonyl)-3-methylpiperazin-1-yl)pyrazine-2-carbonitrile (18-e)

To a solution of 3,5-dichloropyrazine-2-carbonitrile (12-d) (0.50 g, 2.87 mmol) in tert-butanol (30 mL) were added (R)-cyclopropyl(2-methylpiperazin-1-yl)methanone (18-b) (0.48 g, 2.87 mmol) and DIPEA (1.85 g, 14.4 mmol) at RT. The resulting mixture was heated and stirred for 1 h at 50° C. After cooling to room temperature, the reaction mixture was diluted with water (20 mL). The resulting solution was extracted with EtOAc (3×30 mL). The combined organic layers were washed with brine (20 mL), dried over anhydrous sodium sulfate and filtered. The filtrate was concentrated under reduced pressure. The residue was purified by a column chromatography (silica gel, eluting with a gradient of 0%-60% EtOAc in hexanes to afford (R)-3-chloro-5-(4-(cyclopropanecarbonyl)-3-methylpiperazin-1-yl)pyrazine-2-carbonitrile (18-e). MS (ESI) Calc'd for ($C_{14}H_{17}ClN_5O$) [M+H]+, 306; found, 306

Step 5 (R)-5-(4-(cyclopropanecarbonyl)-3-methylpiperazin-1-yl)-3-(1-(methyl-d3)-1H-pyrazol-4-yl)pyrazine-2-carbonitrile (1-18)

To a solution of (R)-3-chloro-5-(4-(cyclopropanecarbonyl)-3-methyl piperazin-1-yl)pyrazine-2-carbonitrile (18-e) (100 mg, 0.33 mmol) in dioxane/water (20/2 mL) were added 1-(methyl-d3)-4-(4,4,5,5-tetramethyl-1,3,2-dioxaborolan-2-yl)-1H-pyrazole (18-d) (104 mg, 0.49 mmol), $PdCl_2$(dppf) (23.9 mg, 0.03 mmol) and potassium carbonate ($K_2CO_3$) (90 mg, 0.65 mmol) at RT under an atmosphere of nitrogen. The resulting mixture was stirred for 12 h at 80° C. After cooling to RT, the reaction mixture was diluted with water (10 mL). The mixture was extracted with EtOAc (3×30 mL). The combined organic layers were washed with brine (30 mL), dried over anhydrous sodium sulfate and filtered. The filtrate was concentrated under reduced pressure. The residue was purified by thin layer chromatography (silica gel, using DCM: methanol (40:1) (v/v) as an eluent to afford (R)-5-(4-(cyclopropanecarbonyl)-3-methylpiperazin-1-yl)-3-(1-(methyl-d3)-1H-pyrazol-4-yl)pyrazine-2-carbonitrile (1-18). 1H NMR (300 MHz. CDCl3): δ: 8.47 (s, 1H), 8.29 (s, 1H), 8.16 (s, 1H), 4.65-4.61 (m, 1H), 4.39-4.36 (m, 2H), 4.21-4.17 (m, 1H), 3.51-3.37 (m, 2H), 3.28-3.16 (m, 1H), 2.03-1.95 (m, 1H), 1.23-1.08 (m, 3H), 0.76-0.73 (m, 4H). MS (ESI) Calc'd for ($C_{18}H_{19}D_3N_7O$) [M+H]+, 355; found, 355.

Example 19

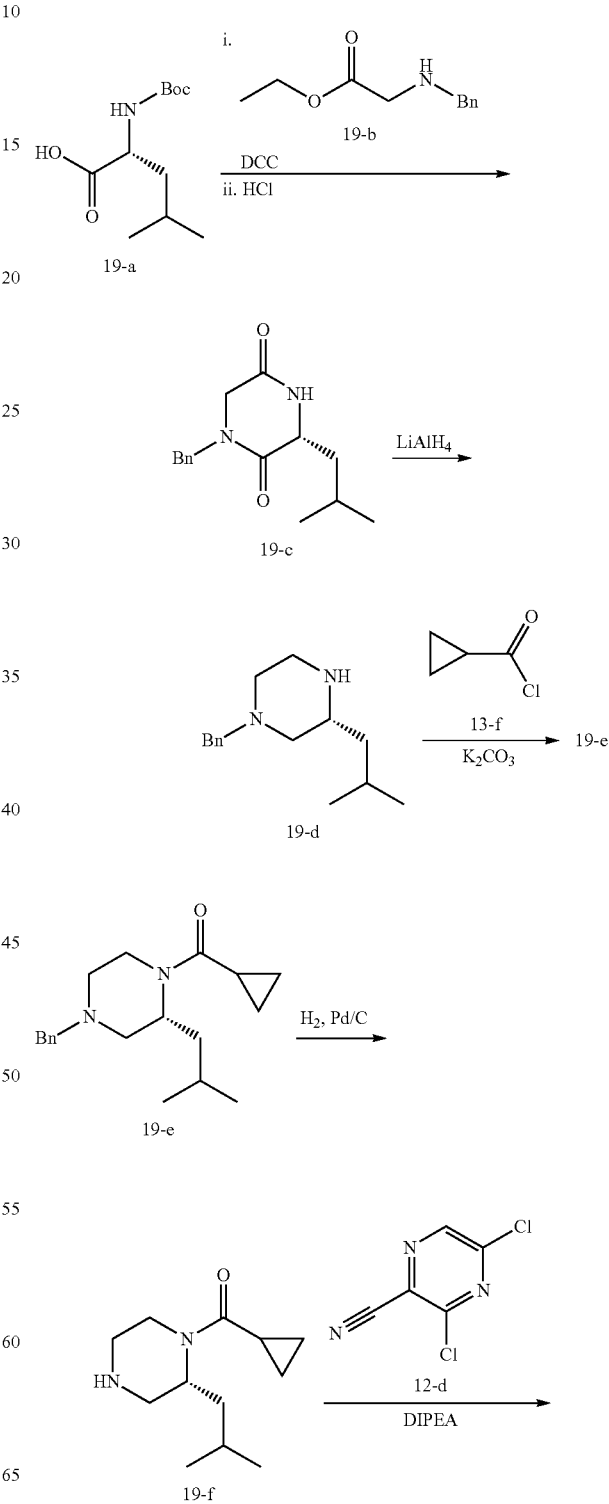

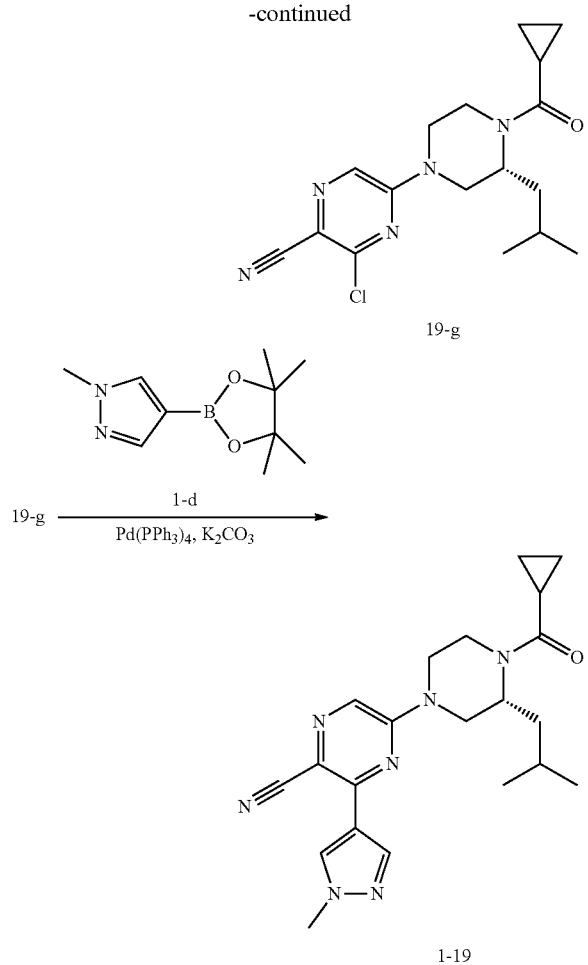

Step 1 (R)-1-Benzyl-3-isobutylpiperazine-2,5-dione (19-e)

To a solution of DCC (8.92 g, 43.2 mmol) in DCM (200 mL) was added (R)-2-((tert-butoxycarbonyl)amino)-4-methylpentanoic acid (commercially available from Shanghai Hanhong Chemical Co., Ltd., Shanghai, P.R. China) (19-a) (10.0 g, 43.2 mmol., at 0° C. To the resulting slurry was added ethyl 2-(benzylamino)acetate (19-b) (commercially available from Nantong Dongchang Chemical Industrial Co., Ltd, Rudong, P. R. China) (8.36 g, 43.2 mmol.) at 0° C. slowly over 15 min. The resulting solution was stirred for 2 h at 0° C., followed by 1 h at RT. The reaction mixture was filtered and concentrated. The intermediate was then re-dissolved in DCM (150 mL), and hydrogen chloride gas was bubbled through the solution for 4 h. The solution was then purged with nitrogen and concentrated under reduced pressure. The residue was neutralized with saturated sodium hydrogen carbonate (aqueous) and the mixture was extracted with EtOAc (3×200 m). The combined organics were washed with water, dried over sodium sulfate, filtered and concentrated to afford (R)-1-benzyl-3-isobutylpiperazine-2,5-dione (19-c) which used to next step directly without further purification. MS (ESI) Calc'd for $(C_{15}H_{21}N_2O_2)$ $[M+H]^+$, 261; found, 261.

Step 2 (R)-1-Benzyl-3-isobutylpiperazine (19-d)

To a mixture of lithium aluminum hydride (LiAlH$_4$) (3.64 g, 96.0 mmol) in THF (20 mL) was added dropwise a solution of (R)-1-benzyl-3-isobutylpiperazine-2,5-dione (19-c) (5.00 g, 19.2 mmol) in THF (20 mL). The resulting mixture was heated at reflux for 3 h. After cooling to RT, the mixture was quenched with saturated magnesium sulfate solution (aqueous), and the resulting solids were removed via filtration. The aqueous layer was then extracted with ether (3×30 mL), and the combined organic layers were washed with brine (20 mL), dried over anhydrous sodium sulfate, and filtered. The filtrate was concentrated under reduced pressure to afford (R)-1-benzyl-3-isobutylpiperazine (19-d) which was used in the next step directly without further purification. MS (ESI) Calc'd for $(C_{15}H_{25}N_2)$ $[M+H]^+$, 233; found, 233.

Step 3 (R)-(4-Benzyl-2-isobutylpiperazin-1-yl)(cyclopropyl)methanone (19-e)

To a solution of (R)-1-benzyl-3-isobutylpiperazine (19-d) (4.00 g, 17.2 mmol) in DCM (50 mL) were added cyclopropanecarbonyl chloride (13-) (2.70 g, 25.8 mmol) and potassium carbonate (4.76 g, 34.4 mmol). The reaction mixture was stirred for 3 h at RT. The reaction was then quenched with water (30 mL) and extracted with EtOAc (3×30 mL). The combined organic layers were washed with brine (20 mL), dried over anhydrous sodium sulfate and filtered. The filtrate was concentrated under reduced pressure, and the residue was purified by a column chromatography (silica gel, eluting with a gradient of 0%-50% EtOAc in hexane to afford (R)-(4-benzyl-2-isobutylpiperazin-1-yl)(cyclopropyl)methanone (19-e). MS (ESI) Calc'd for $(C_{19}H_{29}N_2O)$ $[M+H]^+$, 301; found, 301.

Step 4 (R)-Cyclopropyl(2-isobutylpiperazin-1-yl)methanone (19-f)

To a solution of (R)-(4-benzyl-2-isobutylpiperazin-1-yl)(cyclopropyl)methanone (19-e) (1.50 g, 4.99 mmol) in MeOH (15 mL) was added Pd/C (0.53 g, 0.50 mmol, 10% wet). The resulting mixture was stirred for 3 h at RT under a hydrogen balloon atmosphere. The mixture was then filtered, and the filter cake was washed with DCM (5 mL). The filtrate was then concentrated under reduced pressure to afford (R)-cyclopropyl (2-isobutylpiperazin-1-yl)methanone (19-f) which was used to next step directly without further purification. MS (ESI) Calc'd for $(C_{12}H_{23}N_2O)$ $[M+H]^+$, 211; found, 211.

Step 5 (R)-3-Chloro-5-(4-(cyclopropanecarbonyl)-3-isobutylpiperazin-1-yl)pyrazine-2-carbonitrile (19-&)

To a solution of (R)-cyclopropyl(2-isobutylpiperazin-1-yl)methanone (19-) (0.20 g, 0.95 mmol) and DIPEA (0.25 g, 1.90 mmol) in isopropyl alcohol (IPA) (5 mL) was added 3,5-dichloropyrazine-2-carbonitrile (12-d) (165 mg, 0.95 mmol) at RT. The resulting mixture was heated and stirred for 5 h at 80° C. After cooling to room temperature, the reaction mixture was quenched with water (5 mL). The solution was extracted with EtOAc (3×5 mL). The combined organic layers were dried over anhydrous sodium sulfate and filtered. The filtrate was concentrated under reduced pressure, and the residue was purified by thin layer chromatography, eluting with EtOAc:petroleum ether (1:1) (vol/vol) to afford (R)-3-chloro-5-(4-(cyclopropanecarbonyl)-3-isobutylpiperazin-1-yl)pyrazine-2-carbonitrile (19-g). MS (ESI) Calc'd for $(C_7H_{23}ClN_5O)$ $[M+H]^+$, 348; found, 348.

Step 6 (R)-5-(4-(Cyclopropanecarbonyl)-3-isobutylpiperazin-1-yl)-3-(1-methyl-1H-pyrazol-4-yl)pyrazine-2-carbonitrile (1-19)

To a solution of (R)-3-chloro-5-(4-(cyclopropanecarbonyl)-3-isobutylpiperazin-1-yl)pyrazine-2-carbonitrile (19-g) (100 mg, 0.29 mmol) in 1,4-dioxane (2.5 mL) and water (0.25 ml) were added 1-methyl-4-(4,4,5,5-tetramethyl-1,3,2-dioxaborolan-2-yl)-1H-pyrazole (1-d) (71.8 mg, 0.345 mmol), Pd(PPh$_3$)$_4$ (Tetrakis(triphenylphosphine)palladium (0)) (33.2 mg, 0.029 mmol) and potassium carbonate (79 mg, 0.58 mmol). The reaction mixture was then heated and stirred for 5 h at 80° C. The mixture was quenched with water (3 mL) and extracted with DCM (3×5 mL). The combined organic layers were dried over anhydrous sodium sulfate and filtered, and the filtrate was concentrated under reduced pressure to give a residue which was purified by Prep-HPLC (Column: X Bridge® RP C18, 19*150 mm, 5 um (Waters Corporation, Milford. Mass., USA); Mobile Phase A:Water/10 mM NH4HCO3, Mobile Phase B: ACN; Flow rate: 20 mL/min; Gradient: 20-70% B) to afford (R)-5-(4-(cyclopropanecarbonyl)-3-isobutylpiperazin-1-yl)-3-(1-methyl-1H-pyrazol-4-yl)pyrazine-2-carbonitrile (1-19) $^1$H NMR (300 MHz, CDCl$_3$): δ 8.33 (s, 1H), 8.22 (s, 1H), 7.97 (s, 1H), 4.93-4.16 (m, 4H), 4.01 (s, 3H), 3.70-3.00 (m, 3H), 2.05-1.95 (m, 1H), 1.80-1.70 (m, 1H), 1.63-1.52 (m, 2H), 1.08-1.05 (m, 2H), 0.98-0.92 (m, 6H), 0.86-0.84 (m, 2H). MS (ESI) Calc'd for (C$_{21}$H$_{28}$ClN$_7$O) [M+H]$^+$, 394; found, 394.

Compound 1-20 of Table 1 was prepared in a manner analogous to Example 1, substituting 3-(bromomethyl)-1,1-difluorocyclobutane for (bromomethyl)cyclopropane.

Compound 1-21 found in Table 1 was prepared in a manner analogous to Example 1, substituting 2,2,2-trifluoroethyl trifluoromethanesulfonate for (bromomethyl)cyclopropane.

Compounds 1-22 and 1-23 found in Table 1 were prepared in a manner analogous to Example 2, using the corresponding alkyl bromides.

Compound 1-24 found in Table 1 was prepared using a sequence analogous to that in Example 1, substituting 1,8-diazaspiro[4.5]decan-2-one for 3-oxa-1,8-diazaspiro[4.5]decan-2-one.

Compounds 1-25 and 1-26 found in Table 1 was prepared in a manner analogous to Example 2, Step 1, except that 4-(4-methylpiperidin-4-yl)morpholine, 2HCl and 4'-methyl-1,4'-bipiperidine, 2HCl (commercially available from Ark Pharm, Inc., Arlington Heights, Ill., USA) respectively were used in place of 3-oxa-1,8-diazaspiro[4.5]decan-2-one and potassium carbonate was used in place of DIEA.

Compound 1-27 found in Table 1 was prepared in a manner analogous to Example 14, except that 3-methoxycyclobutanecarboxylic acid (mixture of cis and trans, commercially available from Ark Pharm, Inc., Arlington Heights, Ill., USA) was used in place of cyclopropanamine. The two diastereomers were separated following amide formation via SFC chromatography (Column & dimensions (mm): IB, 21×250; Flow rate (ml/min): 70; Modifier: MeOH w/0.25% DMEA; % modifier in CO2:30). Compound 1-27 was the slower-eluting diastereomer (4.6 min).

Compounds 1-28 through 1-31 were prepared in a manner analogous to Example 14, using the appropriate carboxylic acids (commercially available from Ark Pharm, Inc., Arlington Heights, Ill., USA).

Compounds 1-32 through 1-38 were prepared in a manner analogous to Example 16, using the appropriate commercially-available alcohol and amine nucleophiles.

Compound 1-39 was prepared in a manner analogous to Example 17, except that 4-(4,4,5,5-tetramethyl-1,3,2-dioxaborolan-2-yl)-1H-pyrazole was used in place of 1-(difluoromethyl)-4-(4,4,5,5-tetramethyl-1,3,2-dioxaborolan-2-yl)-1H-pyrazole.

TABLE 1

| Compound | Structure | Name | Exact Mass [M + H]+ |
|---|---|---|---|
| 1-1 | 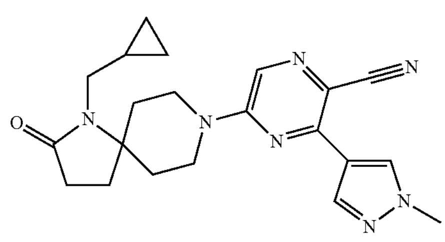 [SMILES: Cn1cc(-c2nc(N3CCC4(CCC(=O)N4CC4CC4)CC3)cnc2C#N)cn1] | 5-[1-(cyclopropylmethyl)-2-oxo-1,8-diazaspiro[4.5]dec-8-yl]-3-(1-methyl-1H-pyrazol-4-yl)pyrazine-2-carbonitrile | Calc+d 392, found 392 |
| 1-2 | 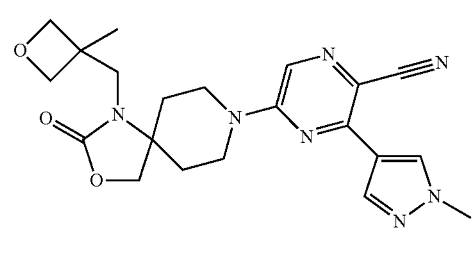 [SMILES: Cn1cc(-c2nc(N3CCC4(CC3)COC(=O)N4CC3(C)COC3)cnc2C#N)cn1] | 5-{1-[(3-methyloxetan-3-yl)methyl]-2-oxo-3-oxa-1,8-diazaspiro[4.5]dec-8-yl}-3-(1-methyl-1H-pyrazol-4-yl)pyrazine-2-carbonitrile | Calc'd 424, found 424 |

TABLE 1-continued

| Compound | Structure | Name | Exact Mass [M + H]+ |
|---|---|---|---|
| 1-3 | 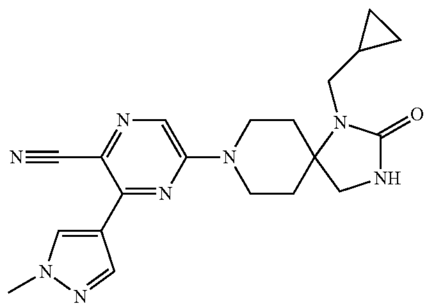 [SMILES: Cn1cc(-c2nc(N3CCC4(CC3)CNC(=O)N4CC3CC3)cnc2C#N)cn1] | 5-[1-(cyclopropylmethyl)-2-oxo-1,3,8-triazaspiro[4.5]dec-8-yl]-3-(1-methyl-1H-pyrazol-4-yl)pyrazine-2-carbonitrile | Calc'd 393, found 393 |
| 1-4 | 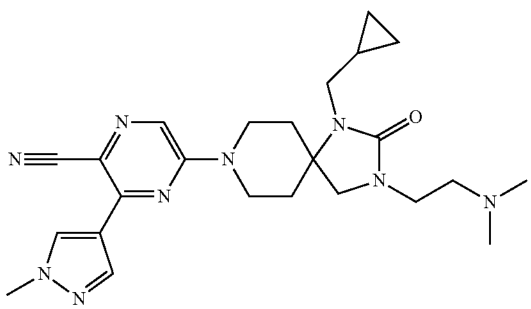 | 5-{1-(cyclopropylmethyl)-3-[2-(dimethylamino)ethyl]-2-oxo-1,3,8-triazaspiro[4.5]dec-8-yl}-3-(1-methyl-1H-pyrazol-4-yl)pyrazine-3-carbonitrile | Calc'd 464, found 464 |
| 1-5 | 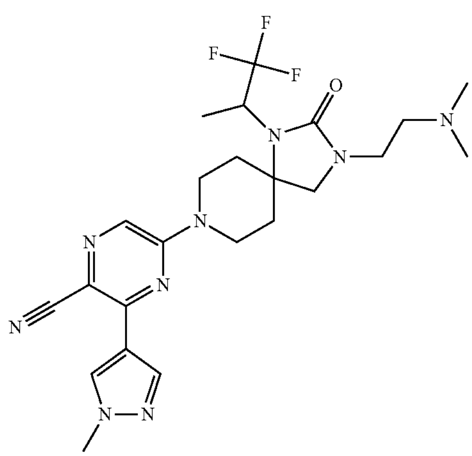 [SMILES: CC(N1C(=O)N(CCN(C)C)CC12CCN(c1cnc(C#N)c(-c3cnn(C)c3)n1)CC2)C(F)(F)F] | 5-{3-[2-(dimethylamino)ethyl]-2-oxo-1-(2,2,2-trifluoro-1-methylethyl)-1,3,8-triazaspiro[4.5]dec-8-yl}-3-(1-methyl-1H-pyrazol-4-yl)pyrazine-2-carbonitrile | Calc'd 506, found 506 |
| 1-6 | 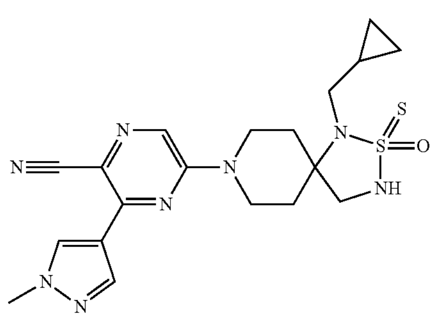 [SMILES: Cn1cc(-c2nc(N3CCC4(CC3)CNS(=O)(=S)N4CC3CC3)cnc2C#N)cn1] | 5-[1-(cyclopropylmethyl)-2,2-dioxido-2-thia-1,3,8-triazaspiro[4.5]dec-8-yl]-3-(1-methyl-1H-pyrazol-4-yl)pyrazine-2-carbonitrile | Calc'd 429, found 429 |

TABLE 1-continued

| Compound | Structure | Name | Exact Mass [M + H]+ |
|---|---|---|---|
| 1-7 | 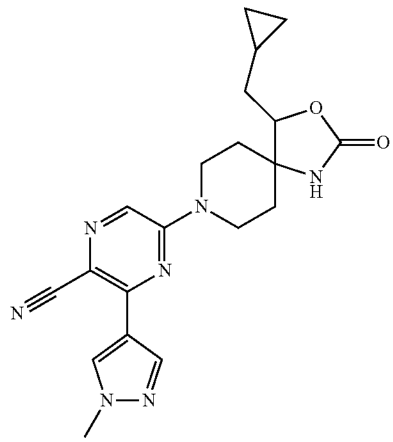 [SMILES: Cn1cc(-c2nc(N3CCC4(CC3)NC(=O)OC4CC3CC3)cnc2C#N)cn1] | 5-[4-(cyclopropylmethyl)-2-oxo-3-oxa-1,8-diazaspiro[4.5]dec-8-yl]-3-(1-methyl-1H-pyrazol-4-yl)pyrazine-2-carbonitrile | Calc'd 394, found 394 |
| 1-8 | 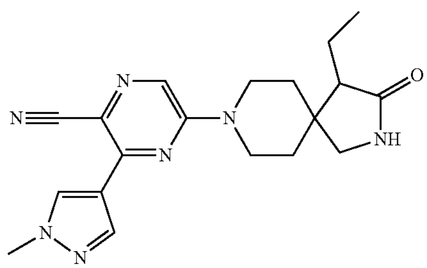 [SMILES: CCC1C(=O)NCC12CCN(c1cnc(C#N)c(-c3cnn(C)c3)n1)CC2] | 5-(4-ethyl-3-oxo-2,8-diazaspiro[4.5]dec-8-yl)-3-(1-methyl-1H-pyrazol-4-yl)pyrazine-2-carbonitrile | Calc'd 366, found 366 |
| 1-9 | 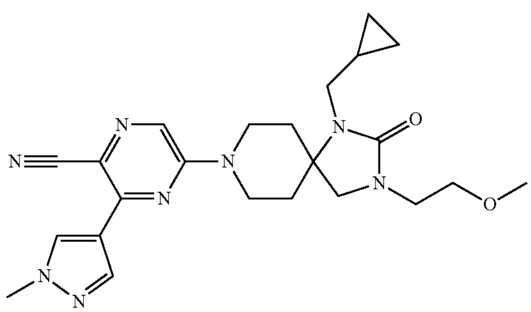 | 5-[1-(cyclopropylmethyl)-3-(2-methoxyethyl)-2-oxo-1,3,8-triazaspiro[4.5]dec-8-yl]-3-(1-methyl-1H-pyrazol-4-yl)pyrazine-2-carbonitrile | Calc'd 451, found 451 |
| 1-10 | 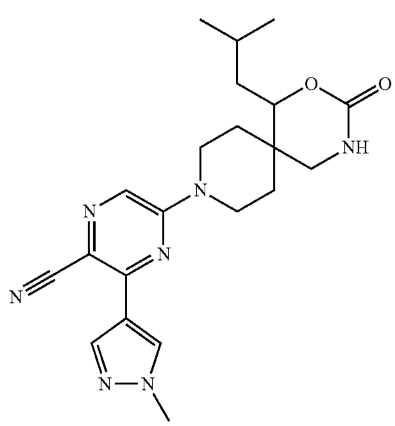 [SMILES: CC(C)CC1OC(=O)NCC12CCN(c1cnc(C#N)c(-c3cnn(C)c3)n1)CC2] | 5-[1-(2-methylpropyl)-3-oxo-2-oxa-4,9-diazaspiro[5.5]undec-9-yl]-3-(1-methyl-1H-pyrazol-4-yl)pyrazine-2-carbonitrile | Calc'd 410, found 410 |

TABLE 1-continued

| Compound | Structure | Name | Exact Mass [M + H]+ |
|---|---|---|---|
| 1-11 | 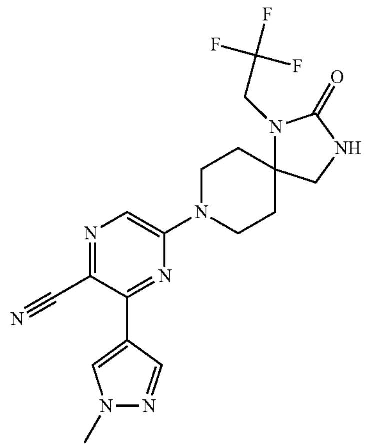 [SMILES: Cn1cc(-c2nc(N3CCC4(CC3)CNC(=O)N4CC(F)(F)F)cnc2C#N)cn1] | 3-(1-methyl-1H-pyrazol-4-yl)-5-[2-oxo-1-(2,2,2-trifluoroethyl)-1,3,8-triazaspiro[4.5]dec-8-yl]pyrazine-2-carbonitrile | Calc'd 421, found 421 |
| 1-12 | 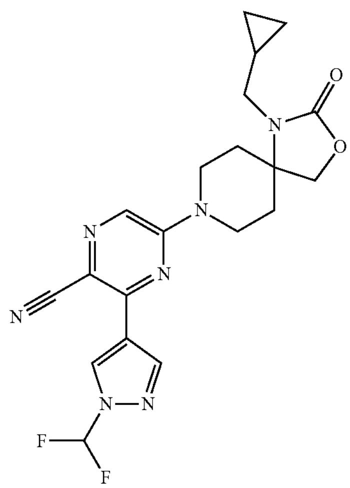 [SMILES: N#Cc1ncc(N2CCC3(CC2)COC(=O)N3CC2CC2)nc1-c1cnn(C(F)F)c1] | 5-[1-(cyclopropylmethyl)-2-oxo-3-oxa-1,8-diazaspiro[4.5]dec-8-yl]-3-[1-(difluoromethyl)-1H-pyrazol-4-yl]pyrazine-2-carbonitrile | Calc'd 430, found 430 |
| 1-13 | 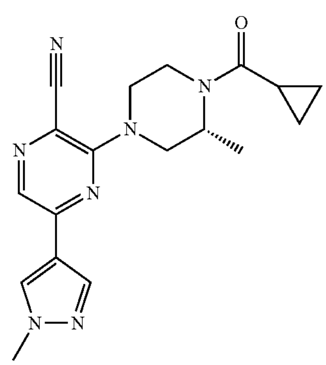 [SMILES: C[C@@H]1CN(c2nc(-c3cnn(C)c3)cnc2C#N)CCN1C(=O)C1CC1] | 3-[(3R)-4-(cyclopropylcarbonyl)-3-methylpiperazin-1-yl]-5-(1-methyl-1H-pyrazol-4-yl)pyrazine-2-carbonitrile | Calc'd 352, found 352 |
| 1-14 | 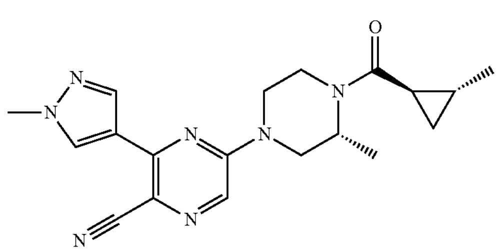 | 5-[(3R)-3-methyl-4-{[(1R,2R)-2-methylcyclopropyl]carbonyl}piperazin-1-yl]-3-(1-methyl-1H-pyrazol-4-yl)pyrazine-2-carbonitrile | Calc'd 366, found 366 |

TABLE 1-continued

| Compound | Structure | Name | Exact Mass [M + H]+ |
|---|---|---|---|
| 1-15 | 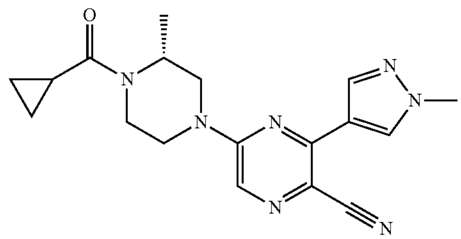 [SMILES: C[C@@H]1CN(c2cnc(C#N)c(-c3cnn(C)c3)n2)CCN1C(=O)C1CC1] | 5-[(3R)-4-(cyclopropylcarbonyl)-3-methylpiperazin-1-yl]-3-(1-methyl-1H-pyrazol-4-yl)pyrazine-2-carbonitrile | Calc'd 352, found 352 |
| 1-16 | 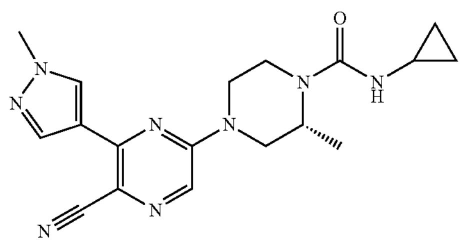 [SMILES: C[C@@H]1CN(c2cnc(C#N)c(-c3cnn(C)c3)n2)CCN1C(=O)NC1CC1] | (2R)-4-[5-cyano-6-(1-methyl-1H-pyrazol-4-yl)pyrazin-2-yl]-N-cyclopropyl-2-methylpiperazine-1-carboxamide | Calc'd 367, found 367 |
| 1-17 | 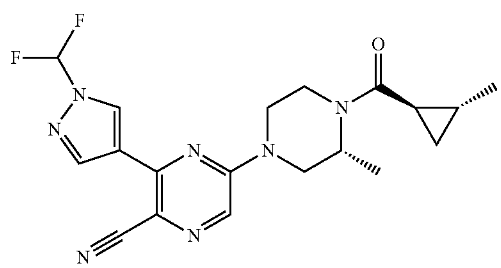 [SMILES: C[C@@H]1C[C@H]1C(=O)N1CCN(c2cnc(C#N)c(-c3cnn(C(F)F)c3)n2)C[C@H]1C] | 3-[1-(difluoromethyl)-1H-pyrazol-4-yl]-5-[(3R)-3-methyl-4-{[(1R,2R)-2-methylcyclopropyl]carbonyl}piperazin-1-yl]pyrazine-2-carbonitrile | Calc'd 402, found 402 |
| 1-18 | 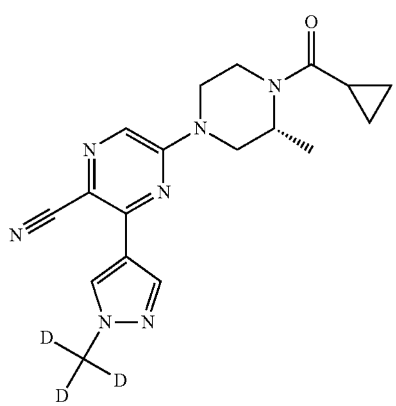 [SMILES: [2H]C([2H])([2H])n1cc(-c2nc(N3CCN(C(=O)C4CC4)[C@H](C)C3)cnc2C#N)cn1] | 5-[(3R)-4-(cyclopropylcarbonyl)-3-methylpiperazin-1-yl]-3-[1-(~2~H_3_)methyl-1H-pyrazol-4-yl]pyrazine-2-carbonitrile | Calc'd 355, found 355 |
| 1-19 | 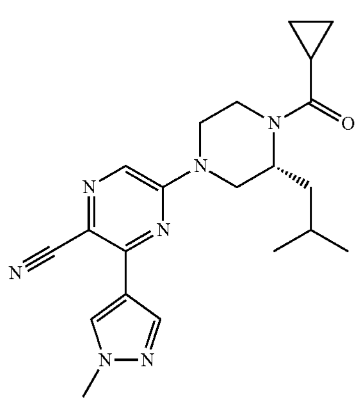 [SMILES: CC(C)C[C@@H]1CN(c2cnc(C#N)c(-c3cnn(C)c3)n2)CCN1C(=O)C1CC1] | 5-[(3R)-4-(cyclopropylcarbonyl)-3-(2-methylpropyl)piperazin-1-yl]-3-(1-methyl-1H-pyrazol-4-yl)pyrazine-2-carbonitrile | Calc'd 394, found 394 |

TABLE 1-continued

| Compound | Structure | Name | Exact Mass [M + H]+ |
|---|---|---|---|
| 1-20 | 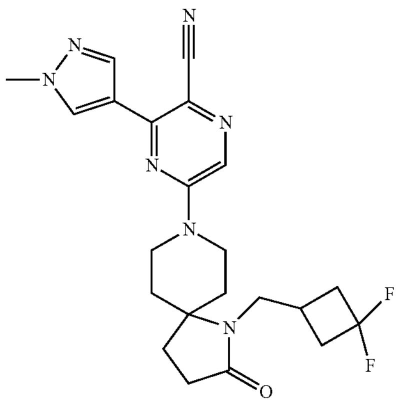 [SMILES: Cn1cc(-c2nc(N3CCC4(CCC(=O)N4CC4CC(F)(F)C4)CC3)cnc2C#N)cn1] | 5-{1-[(3,3-difluorocyclobutyl)methyl]-2-oxo-1,8-diazaspiro[4.5]dec-8-yl}-3-(1-methyl-1H-pyrazol-4-yl)pyrazine-2-carbonitrile | Calc'd 442, found 442 |
| 1-21 | 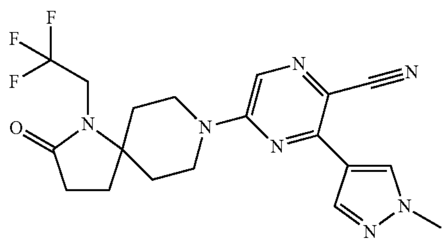 [SMILES: Cn1cc(-c2nc(N3CCC4(CCC(=O)N4CC(F)(F)F)CC3)cnc2C#N)cn1] | 3-(1-methyl-1H-pyrazol-4-yl)-5-[2-oxo-1-(2,2,2-trifluoroethyl)-1,8-diazaspiro[4.5]dec-8-yl]pyrazine-2-carbonitrile | Calc'd 420, found 420 |
| 1-22 | 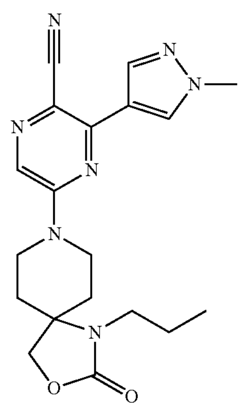 [SMILES: CCCN1C(=O)OCC12CCN(c1cnc(C#N)c(-c3cnn(C)c3)n1)CC2] | 3-(1-methyl-1H-pyrazol-4-yl)-5-(2-oxo-1-propyl-3-oxa-1,8-diazaspiro[4.5]dec-8-yl)pyrazine-2-carbonitrile | Calc'd 382, found 382 |
| 1-23 | 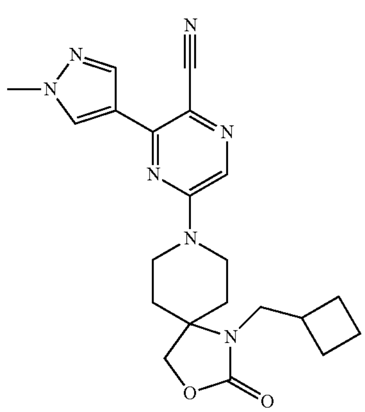 [SMILES: Cn1cc(-c2nc(N3CCC4(CC3)COC(=O)N4CC3CCC3)cnc2C#N)cn1] | 5-[1-(cyclobutylmethyl)-2-oxo-3-oxa-1,8-diazaspiro[4.5]dec-8-yl]-3-(1-methyl-1H-pyrazol-4-yl)pyrazine-2-carbonitrile | Calc'd 408, found 408 |

TABLE 1-continued

| Compound | Structure | Name | Exact Mass [M + H]+ |
|---|---|---|---|
| 1-24 | 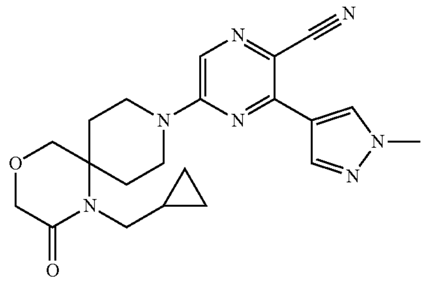 [SMILES: Cn1cc(-c2nc(N3CCC4(CC3)COCC(=O)N4CC3CC3)cnc2C#N)cn1] | 5-[1-(cylcopropylmethyl)-2-oxo-4-oxa-1,8-diazaspiro[5.5]undec-9-yl]-3-(1-methyl-1H-pyrazol-4-yl)pyrazine-2-carbonitrile | Calc'd 408, found 408 |
| 1-25 | 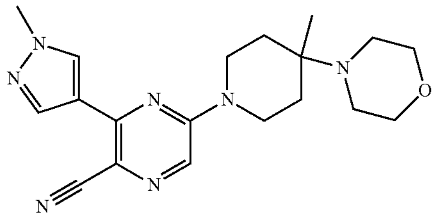 [SMILES: Cn1cc(-c2nc(N3CCC(C)(N4CCOCC4)CC3)cnc2C#N)cn1] | 5-(4-methyl-4-morpholin-4-ylpiperidin-1-yl)-3-(1-methyl-1H-pyrazol-4-yl)pyrazine-2-carbonitrile | Calc'd 368, found 368 |
| 1-26 | 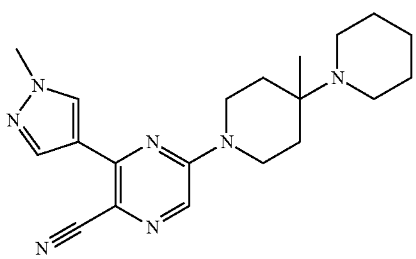 [SMILES: Cn1cc(-c2nc(N3CCC(C)(N4CCCCC4)CC3)cnc2C#N)cn1] | 5-(4'-methyl-1,4'-bipiperidin-1'-yl)-3-(1-methyl-1H-pyrazol-4-yl)pyrazine-2-carbonitrile | Calc'd 366, found 366 |
| 1-27 | 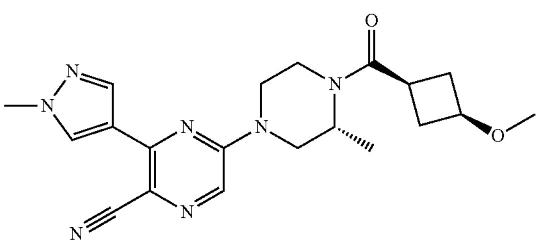 | 5-{(3R)-4-[(cis-3-methoxycyclobutyl)carbonyl]-3-methylpiperazin-1-yl}-3-(1-methyl-1H-pyrazol-4-yl)pyrazine-2-carbonitrile | Calc'd 396, found 396 |
| 1-28 | 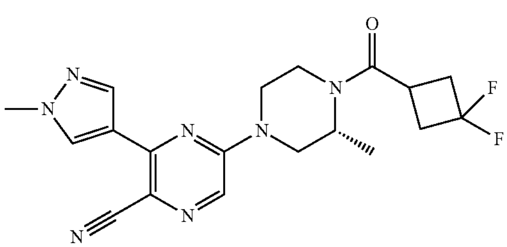 [SMILES: C[C@@H]1CN(c2cnc(C#N)c(-c3cnn(C)c3)n2)CCN1C(=O)C1CC(F)(F)C1] | 5-{(3R)-4-[(3,3-difluorocyclobutyl)carbonyl]-3-methylpiperazin-1-yl}-3-(1-methyl-1H-pyrazol-4-yl)pyrazine-2-carbonitrile | Calc'd 402, found 402 |
| 1-29 | 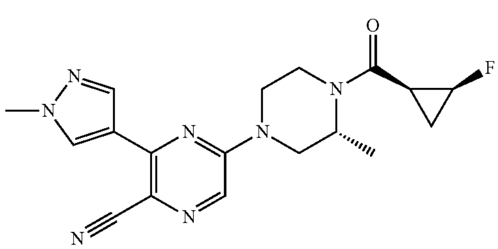 [SMILES: C[C@@H]1CN(c2cnc(C#N)c(-c3cnn(C)c3)n2)CCN1C(=O)[C@@H]1C[C@@H]1F] | 5-[(3R)-4-{[(1S,2S)-2-fluorocyclopropyl]carbonyl}-3-methylpiperazin-1-yl]-3-(1-methyl-1H-pyrazol-4-yl)pyrazine-2-carbonitrile | Calc'd 370, found 370 |

TABLE 1-continued

| Compound | Structure | Name | Exact Mass [M + H]+ |
|---|---|---|---|
| 1-30 | 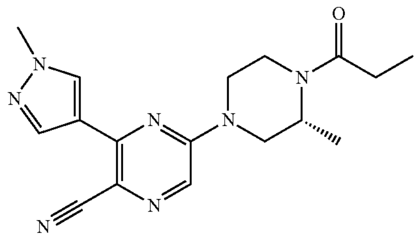 [SMILES: CCC(=O)N1CCN(c2cnc(C#N)c(-c3cnn(C)c3)n2)C[C@H]1C] | 5-[(3R)-3-methyl-4-propanoylpiperazin-1-yl]-3-(1-methyl-1H-pyrazol-4-yl)pyrazine-2-carbonitrile | Calc'd 340, found 340 |
| 1-31 | 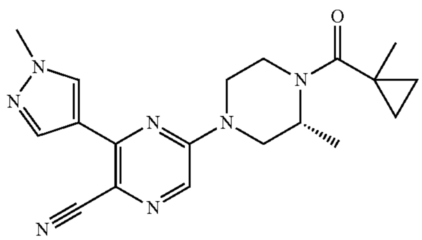 [SMILES: C[C@@H]1CN(c2cnc(C#N)c(-c3cnn(C)c3)n2)CCN1C(=O)C1(C)CC1] | 5-{(3R)-3-methyl-4-[(1-methylcyclopropyl)carbonyl]piperazin-1-yl}-3-(1-methyl-1H-pyrazol-4-yl)pyrazine-2-carbonitrile | Calc'd 366, found 366 |
| 1-32 | 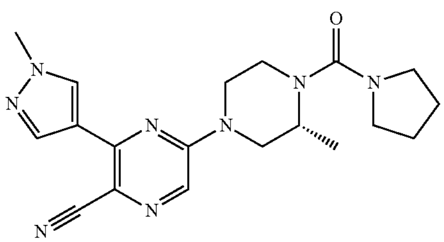 [SMILES: C[C@@H]1CN(c2cnc(C#N)c(-c3cnn(C)c3)n2)CCN1C(=O)N1CCCC1] | 3-(1-methyl-1H-pyrazol-4-yl)-5-[(3R)-3-methyl-4-(pyrrolidin-1-ylcarbonyl)piperazin-1-yl]pyrazine-2-carbonitrile | Calc'd 381, found 381 |
| 1-33 | 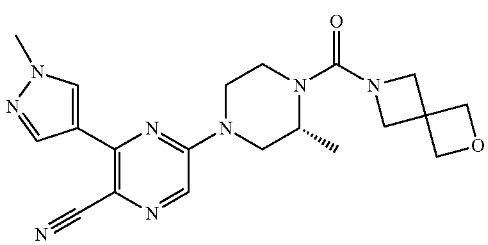 [SMILES: C[C@@H]1CN(c2cnc(C#N)c(-c3cnn(C)c3)n2)CCN1C(=O)N1CC2(COC2)C1] | 5-[(3R)-3-methyl-4-(2-oxa-6-azaspiro[3.3]hept-6-ylcarbonyl)piperazin-1-yl]-3-(1-methyl-1H-pyrazol-4-yl)pyrazine-2-carbonitrile | Calc'd 409, found 409 |
| 1-34 | 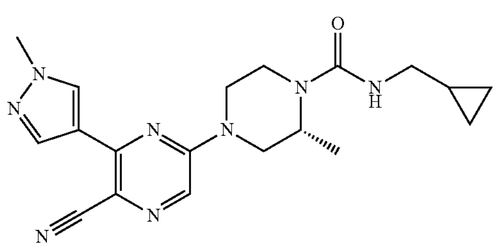 [SMILES: C[C@@H]1CN(c2cnc(C#N)c(-c3cnn(C)c3)n2)CCN1C(=O)NCC1CC1] | (2R)-4-[5-cyano-6-(1-methyl-1H-pyrazol-4-yl)pyrazin-2-yl]-N-(cyclopropylmethyl)-2-methylpiperazine-1-carboxamide | Calc'd 381, found 381 |
| 1-35 | 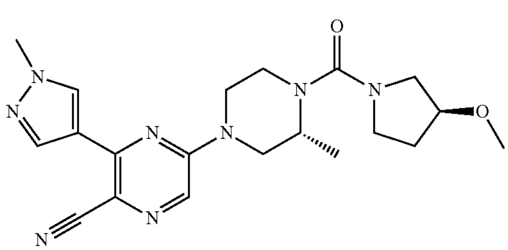 [SMILES: CO[C@H]1CCN(C(=O)N2CCN(c3cnc(C#N)c(-c4cnn(C)c4)n3)C[C@H]2C)C1] | 5-[(3R)-4-{[(3S)-3-methoxypyrrolidin-1-yl]carbonyl}-3-methylpiperazin-1-yl]-3-(1-methyl-1H-pyrazol-4-yl)pyrazine-2-carbonitrile | Calc'd 411, found 411 |

TABLE 1-continued

| Compound | Structure | Name | Exact Mass [M + H]+ |
|---|---|---|---|
| 1-36 | 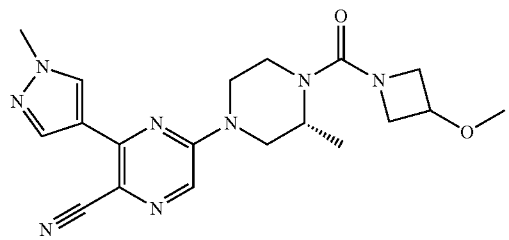 [SMILES: COC1CN(C(=O)N2CCN(c3cnc(C#N)c(-c4cnn(C)c4)n3)C[C@H]2C)C1] | 5-{(3R)-4-[(3-methoxyazetidin-1-yl)carbonyl]-3-methylpiperazin-1-yl}-3-(1-methyl-1H-pyrazol-4-yl)pyrazine-2-carbonitrile | Calc'd 397, found 397 |
| 1-37 | 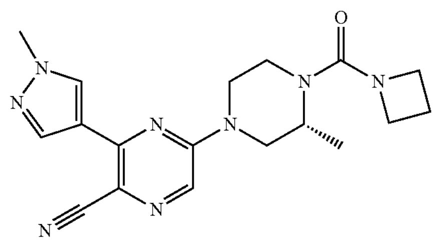 [SMILES: C[C@@H]1CN(c2cnc(C#N)c(-c3cnn(C)c3)n2)CCN1C(=O)N1CCC1] | 5-[(3R)-4-(azetidin-1-ylcarbonyl)-3-methylpiperazin-1-yl]-3-(1-methyl-1H-pyrazol-4-yl)pyrazine-2-carbonitrile | Calc'd 367, found 367 |
| 1-38 | 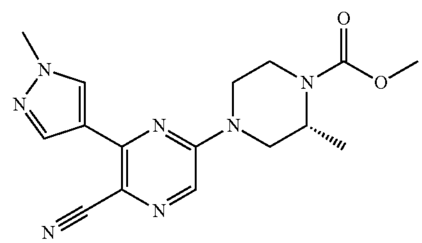 [SMILES: COC(=O)N1CCN(c2cnc(C#N)c(-c3cnn(C)c3)n2)C[C@H]1C] | methyl (2R)-4-[5-cyano-6-(1-methyl-1H-pyrazol-4-yl)pyrazin-2-yl]-2-methylpiperazine-1-carboxylate | Calc'd 342, found 342 |
| 1-39 | 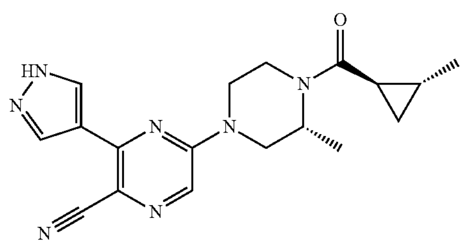 [SMILES: C[C@@H]1C[C@H]1C(=O)N1CCN(c2cnc(C#N)c(-c3cn[nH]c3)n2)C[C@H]1C] | 5-[(3R)-3-methyl-4-{[(1R,2R)-2-methylcyclopropyl]carbonyl}piperazin-1-yl]-3-(1H-pyrazol-4-yl)pyrazine-2-carbonitrile | Calc'd 352, found 352 |

HTRF PI3K Biochemical Assay to Measure Intrinsic Potency of Compound Inhibitors

The PI3-Kinase biochemical assays were developed to measure the intrinsic potency and compound dependent inhibition of the alpha, beta, delta, and gamma PI3K isoform enzymes. This assay was developed and further optimized from a kit produced by Upstate (Millipore catalog #33-047) (Millipore Sigma. Billerica Mass., USA) and has been configured for high throughput screening (HTS) and structure-activity relationship (SAR) screening. Briefly, this procedure exploits the exquisite specificity and high affinity binding of enzyme reaction substrate phosphatidyl(3,4,5)triphosphate (PIP3) to the GRP1 pleckstrin homology (PH) domain to generate the signal. In the absence of PIP3, an HTRF (Homogeneous Time-Resolved Fluorescence energy transfer) complex is formed consisting of europium (Eu)-labeled anti-GST, GSTtagged GRP1-PH domain, biotin-PIP3 (biotinylated-PIP3) and streptavidin conjugated APC (Allophycocyanin). The native PIP3 produced by PI3-Kinase activity disrupts in a competitive manner the biotin-PIP3 from the pleckstrin homology (PH) domain, resulting in the loss of energy transfer (HTRF complex) and a decrease in the signal. The format of this assay is the same for all 4 isoforms of PI3K; the differences lie in the concentration of enzyme used to achieve robust assay window. The alpha, beta, and delta assays are run at 0.5, 1, and 0.3 nM enzymes and the gamma assay is run at 5 nM enzyme. The ATP concentration is 100 uM in the alpha, beta, and delta assays and 50 uM adenosine triphosphate (ATP) in the gamma assay. All reactions are run at 5 uM PIP2.

Assay Protocol

Compounds are serially diluted (3-fold in 100% DMSO) across a 384-well polypropylene source plated from column 3 to column 12 and column 13 to column 22, to yield 10 concentration dose response for each test compound. Columns 1, 2, 23 and 24 contain either only DMSO or pharmacological known control inhibitor. Once titrations are made, 2.5 nL of the compounds on 384 well plates are reformatted and transferred by acoustic dispense in quadruplicates to a 1536 assay plate (Greiner) to assay across all four PI3K isoform enzymes.

The PI3-Kinase biochemical assay was optimized using the HTRF kit provided by Upstate (Millipore). The assay kit contains six reagents: 1) 4×Reaction Buffer; 2) native PIP2

(substrate); 3) Stop (EDTA); 4) Detection Mix A (Streptavidin-APC); 5) Detection Mix B (Eu-labeled Anti-GST plus GST-tagged PH-domain): 6) Detection Mix C. In addition, the following items were obtained or purchased; PI3Kinase (catalog #'s alpha 14-602, beta 14-603, gamma 14-558 and delta 14-604 from Upstate Biotechnology now EMD Millipore, Mahopac, N.Y., USA), dithiothreitol (Sigma-Aldrich Corp. (St. Louis, Mo., USA) Catalog #D-5545), Adenosine-5' triphosphate (InVitrogen (Waltham, Mass., USA), Cat#AS001 Å), native PIP3 (PI(3,4,5)P3, diC8, H$^+$, CELLSIGNALS, INC., (Columbus, Ohio, USA) Cat #907) DMSO ((Sigma-Aldrich Corp. (St. Louis. Mo., USA) Catalog #472301).

PI3Kinase Reaction Buffer is prepared by dilution the stock 1:4 with de-ionized water. DTT (DL-Dithiothreitol), phosphatidylinositol 4,5-bisphosphate (PIP2) and Biotin-PIP3 were added to 1536 assay plate at a final concentration of 5 mM, 5 mM and 25 nM on the day of use. Enzyme addition and compound pre-incubation are initiated by the addition of 1.25 ul of PI3K (at twice its final concentration) in the 1× reaction buffer to all wells using a BioRaptor™. Plates are incubated at room temperature for 15 minutes. Reactions are initiated by addition of 1.25 ul of 2× substrate solution (PIP2 and ATP in 1× reaction buffer) using BioRaptor™. Plates are incubated in humidified chamber at room temperature for one hour. Reactions are quenched by addition of 0.625 uL of stop solution to all wells using the BioRaptor™. The quenched reactions are then processed to detect product formation by adding 0.625 uL of Detection Solution to all wells using the BioRaptor™ (Detection mix C, Detection Mix A and Detection Mix B combined together in an 18:1:1 ratio prepared 2 hours prior to use). Following a one hour incubation in the dark, the HTRF signal is measured on the Envision plate reader set for 330 nm excitation and dual emission detection at 620 nM (Eu) and 665 nM (APC).

Data Analysis

The loss of the HTRF signal is due to the displacement of biotinylated-PIP3 from the PH domain by the PI3K-dependent conversion of PIP2 to PIP3. This loss of signal is nonlinear with respect to both increasing product and time. This non-linear detection will impact accuracy of $IC_{50}$ calculations; therefore, there is a need for a correction factor to obtain more accurate ICw values. This correction is derived from a PIP3 standard curve run in a separate assay plate. All data were calculated using the ratio of acceptor (APC) to donor (Europium) fluorescence in each well of the assay plate. The percent inhibition for each compound concentration was calculated as follows: % inhibition=100× (fluorescence ratio−CtrlB)/(CtrlA−CtrlB) where CtrlA=PI3Kinase reaction+known reference inhibitor and CtrlB=PI3K+DMSO. An $IC_{50}$ was then calculated fitting the % inhibition data to the equation: % (percent) inhibition=min+(Max−min)/1+([inhibitor]/C50)^n) where min is the % inhibition with inhibitor, max is the signal in DMSO control, and n is the Hill slope.

Biological Data

The following table tabulates the biological data disclosed for the instant invention. The biological data was collected using the methodology described above. For each compound, PI3Kdelta $IC_{50}$ values are listed along with the relative selectivity versus PI3Kalpha, as well as the physical form of the compound dosed in this assay.

The determination of relative selectivity for a given compound is defined as the relative ratio of the (PI3K-alpha$IC_{50}$ value/PI3K-delta $IC_{50}$ value).

| Compound Number | Form Screened | PI3Kdelta IC50 (nM) | Selectivity versus PI3Kalpha |
|---|---|---|---|
| 1-1 | TFA salt | 5.4 | >10 |
| 1-2 | Neutral | 45 | >10 |
| 1-3 | Neutral | 9.7 | >10 |
| 1-4 | Neutral | 10 | >10 |
| 1-5 | Neutral | 7.2 | >10 |
| 1-6 | Neutral | 12 | >10 |
| 1-7 | Neutral | 55 | >10 |
| 1-8 | Neutral | 60 | >10 |
| 1-9 | Neutral | 18 | >10 |
| 1-10 | Neutral | 30 | >10 |
| 1-11 | Neutral | 32 | >10 |
| 1-12 | Neutral | 54 | >10 |
| 1-13 | Neutral | 190 | >10 |
| 1-14 | Neutral | 8.9 | >10 |
| 1-15 | Neutral | 33 | >10 |
| 1-16 | TFA salt | 280 | >10 |
| 1-17 | Neutral | 73 | >10 |
| 1-18 | Neutral | 16 | >10 |
| 1-19 | Neutral | 39 | >10 |
| 1-20 | Neutral | 18 | >10 |
| 1-21 | TFA salt | 37 | >10 |
| 1-22 | Neutral | 30 | >10 |
| 1-23 | Neutral | 18 | >10 |
| 1-24 | Neutral | 10 | >10 |
| 1-25 | Neutral | 52 | >10 |
| 1-26 | TFA salt | 70 | >10 |
| 1-27 | Neutral | 100 | >10 |
| 1-28 | Neutral | 100 | >10 |
| 1-29 | TFA salt | 29 | >10 |
| 1-30 | Neutral | 150 | >10 |
| 1-31 | Neutral | 280 | >10 |
| 1-32 | TFA salt | 180 | >10 |
| 1-33 | TFA salt | 300 | >10 |
| 1-34 | TFA salt | 210 | >10 |
| 1-35 | TFA salt | 110 | >10 |
| 1-36 | Neutral | 160 | >10 |
| 1-37 | Neutral | 53 | >10 |
| 1-38 | TFA salt | 210 | >10 |
| 1-39 | Neutral | 50 | >10 |

What is claimed is:

1. A compound of Formula (I):

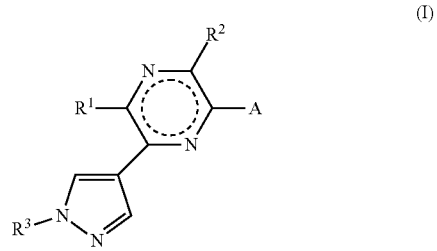

or a pharmaceutically acceptable salt thereof, wherein A is selected from:

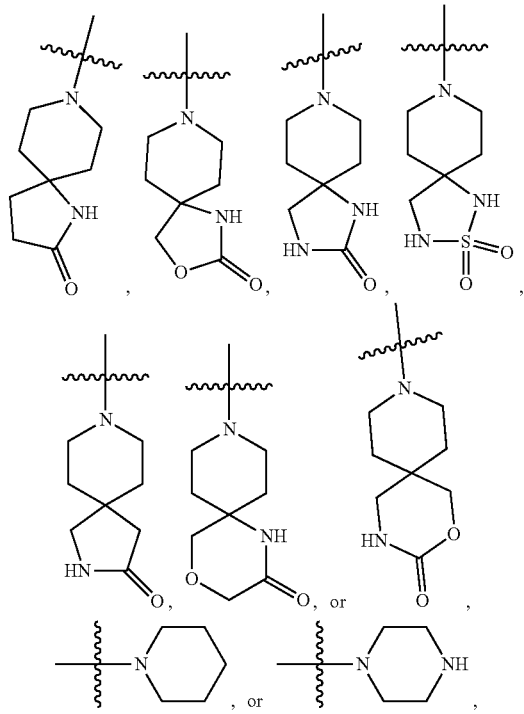

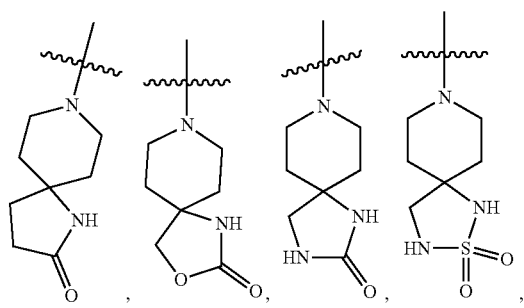

wherein A is substituted with 0, 1, 2, or 3 $R^4$, each
  $R^4$ is independently selected from $C_1$-$C_{10}$ alkyl, $C_{1-10}$ haloalkyl, $C_{3-12}$
  heterocycloalkyl$C_{0-6}$ alkyl, $C_{3-12}$ cycloalkyl($C_{0-6}$ alkyl), amino,
  $C_{3-12}$ cycloalkyl($C_{0-6}$ alkyl)aminocarbonyl, $C_{1-6}$ alkylamino($C_{0-6}$ alkyl),
  $C_{3-12}$ heterocycloalkylcarbonyl($C_{0-6}$ alkyl), $C_{1-10}$ alkylcarbonyl($C_{0-6}$ alkyl),
  $C_{3-12}$ cycloalkylcarbonyl($C_{0-6}$ alkyl), $C_{1-10}$ alkylcarboxy, or
  $C_{1-10}$ alkyloxy($C_{0-6}$ alkyl), wherein each $R^4$ is independently substituted by 0, 1, 2, or
  3 $R^5$ independently selected from halogen, hydroxy, $C_{1-6}$ alkyl, $C_{1-4}$ alkoxy, or
  $C_{1-6}$ haloalkyl;
each $R^1$ and $R^2$ is independently selected from: hydrogen, or cyano provided that only one of
  $R^1$ or $R^2$ is cyano and the other is hydrogen; and
$R^3$ is hydrogen, $C_{1-6}$ haloalkyl, or $C_{1-6}$ alkyl.

2. The compound of claim 1, wherein A is selected from

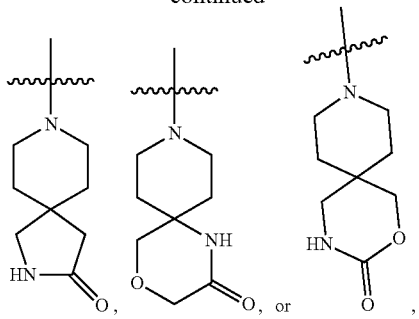

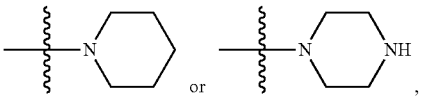

and wherein A is substituted with 0, 1, 2, or 3 $R^4$.

3. The compound of claim 2, wherein A is selected from and wherein A is substituted with 0, 1, 2, or 3 $R^4$.

4. The compound of claim 1, wherein each $R^4$ is independently selected from $C_{1-C10}$ alkyl, $C_{1-10}$ haloalkyl, $C_{3-12}$ heterocycloalkyl$C_{0-6}$ alkyl having 1, 2 or 3 heteroatoms selected from nitrogen or oxygen, $C_{3-12}$ cycloalkyl($C_{0-6}$ alkyl), amino, $C_{3-12}$ cycloalkyl($C_{0-6}$ alkyl)aminocarbonyl, $C_{1-6}$ alkylamino($C_{0-6}$ alkyl), $C_{3-12}$ heterocycloalkylcarbonyl ($C_{0-6}$ alkyl) having 1, 2 or 3 heteroatoms selected from nitrogen or oxygen, $C_{1-10}$ alkylcarbonyl($C_{0-6}$ alkyl), $C_{3-12}$ cycloalkylcarbonyl($C_{0-6}$ alkyl), $C_{1-10}$ alkylcarboxy, or $C_{1-10}$ alkyloxy($C_{0-6}$ alkyl), wherein each $R^4$ is independently substituted by 0, 1, 2, or 3 $R^5$.

5. The compound of claim 4, wherein each $R^4$ is independently selected from cyclopropylmethyl, cyclobutylmethyl, 2,2,2-trifluoroethyl, propyl, oxetanylmethyl, 2,2,2-trifluoro-1-methylethyl, methylaminoethyl, methoxyethyl, cyclopropylaminocarbonyl, ethylcarbonyl, ethyl, isobutyl, methyl, morpholinyl, cyclopropylcarbonyl, cyclobutylcarbonyl, piperidinyl, pyrrolidinylcarbonyl, 2-oxa-6-azaspiro [3,3]heptylcarbonyl, (cyclopropylmethyl)aminocarbonyl, azetidinylcarbonyl, and methylcarboxy, wherein each $R^4$ is independently substituted by 0, 1, 2, or 3 $R^5$.

6. The compound of claim 1, wherein each $R^5$ is independently selected from halogen, $C_{1-6}$ alkyl, or $C_{1-4}$ alkoxy.

7. The compound of claim 1, wherein each $R^5$ is independently selected from fluoro, $C_{1-3}$ alkyl, or $C_{1-4}$ alkoxy.

8. The compound claim 1, wherein $R^3$ is selected from methyl, ethyl, propyl, butyl, pentyl, difluoromethyl, trifluoromethyl, trifluoroethyl or hydrogen.

9. The compound claim 1, wherein $R^3$ is selected from methyl, difluoromethyl, or hydrogen.

10. The compound according to claim 1, or a pharmaceutically acceptable salt thereof, wherein the compound is selected from:
  5-[1-(cyclopropylmethyl)-2-oxo-1,8-diazaspiro[4.5]dec-8-yl]-3-(1-methyl-1H-pyrazol-4-yl)pyrazine-2-carbonitrile;
  5-{1-[(3-methyloxetan-3-yl)methyl]-2-oxo-3-oxa-1,8-diazaspiro[4.5]dec-8-yl}-3-(1-methyl-1H-pyrazol-4-yl)pyrazine-2-carbonitrile;
  5-[1-(cyclopropylmethyl)-2-oxo-1,3,8-triazaspiro[4.5]dec-8-yl]-3-(1-methyl-1H-pyrazol-4-yl)pyrazine-2-carbonitrile;

5-{1-(cyclopropylmethyl)-3-[2-(dimethylamino)ethyl]-2-oxo-1,3,8-triazaspiro[4.5]dec-8-yl}-3-(1-methyl-1H-pyrazol-4-yl)pyrazine-2-carbonitrile;

5-{3-[2-(dimethylamino)ethyl]-2-oxo-1-(2,2,2-trifluoro-1-methylethyl)-1,3,8-triazaspiro [4.5]dec-8-yl}-3 -(1 -methyl-1H-pyrazol-4-yl)pyrazine-2-carbonitrile;

5-[1-(cyclopropylmethyl)-2,2-dioxido-2-thia-1,3,8-triazaspiro [4.5]dec-8-yl]-3-(1-methyl-1H-pyrazol-4-yl)pyrazine-2-carbonitrile;

5-[4-(cyclopropylmethyl)-2-oxo-3-oxa-1,8-diazaspiro[4.5]dec-8-yl]-3-(1-methyl-1H-pyrazol-4-yl)pyrazine-2-carbonitrile;

5-(4-ethyl-3-oxo-2,8-diazaspiro[4.5]dec-8-yl)-3-(1-methyl-1H-pyrazol-4-yl)pyrazine-2-carbonitrile;

5-[1-(cyclopropylmethyl)-3-(2-methoxyethyl)-2-oxo-1,3,8-triazaspiro[4.5]dec-8-yl]-3-(1-methyl-1H-pyrazol-4-yl)pyrazine-2-carbonitrile;

5-[1-(2-methylpropyl)-3-oxo-2-oxa-4,9-diazaspiro[5.5]undec-9-yl]-3-(1-methyl-1H-pyrazol-4-yl)pyrazine-2-carbonitrile;

3-(1-methyl-1H-pyrazol-4-yl)-5-[2-oxo-1-(2,2,2-trifluoroethyl)-1,3,8-triazaspiro[4.5]dec-8-yl]pyrazine-2-carbonitrile;

5[1-(cyclopropylmethyl)-2-oxo-3-oxa-1,8-diazaspiro[4.5]dec-8-yl]-3-[1-(difluoromethyl)-1H-pyrazol-4-yl]pyrazine-2-carbonitrile;

3-[(3R)-4-(cyclopropylcarbonyl)-3-methylpiperazin-1-yl]-5-(1-methyl-1H-pyrazol-4-yl)pyrazine-2-carbonitrile;

5-[(3R)-3-methyl-4-{[(1R,2R)-2-methylcyclopropyl]carbonyl}piperazin-1-yl]-3-(1-methyl-1H-pyrazol-4-yl)pyrazine-2-carbonitrile;

5-[(3R)-4-(cyclopropylcarbonyl)-3-methylpiperazin-1-yl]-3-(1-methyl-1H-pyrazol-4-yl)pyrazine-2-carbonitrile;

(2R)-4-[5-cyano-6-(1-methyl-1H-pyrazol-4-yl)pyrazin-2-yl]-N-cyclopropyl-2-methylpiperazine-1-carboxamide;

3-[1-(difluoromethyl)-1H-pyrazol-4-yl]-5-[(3R)-3-methyl-4-{[(1R,2R)-2-methylcyclopropyl]carbonyl}piperazin-1-yl]pyrazine-2-carbonitrile;

5-[(3R)-4-(cyclopropylcarbonyl)-3-methylpiperazin-1-yl]-3-[1-(~2~H_3_)methyl-1H-pyrazol-4-yl]pyrazine-2-carbonitrile;

5-[(3R)-4-(cyclopropylcarbonyl)-3-(2-methylpropyl)piperazin-1-yl]-3-(1-methyl-1H-pyrazol-4-yl)pyrazine-2-carbonitrile;

5-{1-[(3,3-difluorocyclobutyl)methyl]-2-oxo-1,8-diazaspiro[4.5]dec-8-yl}-3-(1-methyl-1H-pyrazol-4-yl)pyrazine-2-carbonitrile;

3-(1-methyl-1H-pyrazol-4-yl)-5-[2oxo-1-(2,2,2-trifluoroethyl)-1,8-diazaspiro[4.5]dec-8-yl]pyrazine-2-carbonitrile;

3-(1-methyl-1H-pyrazol-4-yl)-5-(2-oxo-1-propyl-3-oxa-1,8-diazaspiro[4.5]dec-8-yl)pyrazine-2-carbonitrile;

5[1-(cyclobutylmethyl)-2-oxo-3-oxa-1,8-diazaspiro[4.5]dec-8-yl]-3-(1-methyl-1H-pyrazol-4-yl)pyrazine-2-carbonitrile;

5-[1-(cyclopropylmethyl)-2-oxo-4-oxa-1,9-diazaspiro[5.5]undec-9-yl]-3-(1-methyl-1H-pyrazol-4-yl)pyrazine-2-carbonitrile;

5-(4-methyl-4-morpholin-4-ylpiperidin-1-yl)-3-(1-methy1-1H-pyrazol-4-yl)pyrazine-2-carbonitrile;

5-(4'-methyl-1,4'-bipiperidin-1'-yl)-3-(1-methy1-1H-pyrazol-4-yl)pyrazine-2-carbonitrile;

5-{(3R)-4-[(cis-3-methoxycyclobutyl)carbonyl]-3-methylpiperazin-1-yl}-3-(1-methyl-1H-pyrazol-4-yl)pyrazine-2-carbonitrile;

5-{(3R)-4-[(3,3-difluorocyclobutyl)carbonyl]-3-methylpiperazin-1-yl}-3-(1-methy1-1H-pyrazol-4-yl)pyrazine-2-carbonitrile;

5-[(3R)-4-{[(1S,2S)-2-fluorocyclopropyl]carbonyl}-3-methylpiperazin-1-yl]-3-(1-methyl-1H-pyrazol-4-yl)pyrazine-2-carbonitrile;

5-[(3R)-3-methyl-4-propanoylpiperazin-1-yl]-3-(1-methyl-1H-pyrazol-4-yl)pyrazine-2-carbonitrile;

5-{(3R)-3-methyl-4-[(1-methylcyclopropyl)carbonyl]piperazin-1-yl}-3-(1-methyl-1H-pyrazol-4-yl)pyrazine-2-carbonitrile;

3-(1-methyl-1H-pyrazol-4-yl)-5-[(3R)-3-methyl-4-(pyrrolidin-1-ylcarbonyl)piperazin-1-yl]pyrazine-2-carbonitrile;

5-[(3R)-3-methyl-4-(2-oxa-6-azaspiro[3.3]hept-6-ylcarbonyl)piperazin-1-yl]-3-(1-methyl-1H-pyrazol-4-yl)pyrazine-2-carbonitrile;

(2R)-4-[5-cyano-6-(1-methyl-1H-pyrazol-4-yl)pyrazin-2-yl]-N-(cyclopropylmethyl)-2-methylpiperazine- 1-carboxamide;

5-[(3R)-4-{[(3S)-3-methoxypyrrolidin-1-yl]carbonyl}-3-methylpiperazin-1-yl]-3-(1-methyl-1H-pyrazol-4-yl)pyrazine-2-carbonitrile;

5-{(3R)-4-[(3-methoxyazetidin-1-yl)carbonyl]-3-methylpiperazin-1-yl}3-(1-methyl-1H-pyrazol-4-yl)pyrazine-2-carbonitrile;

5-[(3R)-4-(azetidin-1-ylcarbonyl)-3-methylpiperazin-1-yl]-3-(1-methyl-1H-pyrazol-4-yl)pyrazine-2-carbonitrile;

methyl (2R)-4-[5-cyano-6-(1-methyl-1H-pyrazol-4-yl)pyrazin-2-yl]-2-methylpiperazine-1-carboxylate; or 5-[(3R)-3-methyl-4-{[(1R,2R)-2-methylcyclopropyl]carbonyl}piperazin-1-yl]-3-(1H-pyrazol-4-yl) pyrazine-2-carbonitrile.

11. A pharmaceutical composition comprising an effective amount of a compound according to claim 1, or a pharmaceutically acceptable salt thereof, and a pharmaceutically acceptable carrier.

12. The pharmaceutical composition according to claim 11, further comprising one or more other therapeutic agents.

13. A method for the inhibition of PI3K-delta comprising administering to a patient an amount of a compound of claim 1 or a pharmaceutically acceptable salt or a stereoisomer thereof effective to inhibit PI3K-delta.

* * * * *